(12) United States Patent
Rao et al.

(10) Patent No.: US 9,975,924 B2
(45) Date of Patent: May 22, 2018

(54) APPROACH TO PRODUCE HIV-1 GP140 ENVELOPE PROTEIN TRIMERS

(71) Applicant: THE CATHOLIC UNIVERSITY OF AMERICA, Washington, DC (US)

(72) Inventors: Venigalla B. Rao, Silver Spring, MD (US); Wadad Alsalmi, Washington, DC (US)

(73) Assignee: The Catholic University of America, Washington, DC (US)

( * ) Notice: Subject to any disclaimer, the term of this patent is extended or adjusted under 35 U.S.C. 154(b) by 133 days.

(21) Appl. No.: 14/806,742

(22) Filed: Jul. 23, 2015

(65) Prior Publication Data
US 2016/0272686 A1 Sep. 22, 2016

Related U.S. Application Data

(60) Provisional application No. 62/133,578, filed on Mar. 16, 2015, provisional application No. 62/166,271, filed on May 26, 2015.

(51) Int. Cl.
| | | |
|---|---|---|
| *C07K 14/005* | (2006.01) | |
| *C12N 7/00* | (2006.01) | |
| *A61K 9/70* | (2006.01) | |
| *A61K 39/21* | (2006.01) | |
| *C07K 1/22* | (2006.01) | |
| *C07K 1/36* | (2006.01) | |
| *A61K 39/12* | (2006.01) | |
| *C07K 14/16* | (2006.01) | |
| *A61K 39/00* | (2006.01) | |

(52) U.S. Cl.
CPC .......... *C07K 14/005* (2013.01); *A61K 9/7023* (2013.01); *A61K 39/12* (2013.01); *A61K 39/21* (2013.01); *C07K 1/22* (2013.01); *C07K 1/36* (2013.01); *C12N 7/00* (2013.01); *A61K 39/00* (2013.01); *A61K 2039/54* (2013.01); *A61K 2039/627* (2013.01); *C07K 14/162* (2013.01); *C07K 2319/00* (2013.01); *C07K 2319/20* (2013.01); *C07K 2319/21* (2013.01); *C07K 2319/22* (2013.01); *C07K 2319/40* (2013.01); *C07K 2319/50* (2013.01); *C12N 2740/16022* (2013.01); *C12N 2740/16043* (2013.01); *C12N 2740/16051* (2013.01); *C12N 2740/16111* (2013.01); *C12N 2740/16122* (2013.01); *C12N 2740/16134* (2013.01); *C12N 2740/16234* (2013.01)

(58) Field of Classification Search
None
See application file for complete search history.

(56) References Cited

U.S. PATENT DOCUMENTS

| | | | |
|---|---|---|---|
| 6,303,337 B1 | 10/2001 | Rothschild et al. | |
| 7,939,083 B2 | 5/2011 | Dey et al. | |
| 8,546,337 B2 | 10/2013 | Burkhard | |
| 8,586,056 B2 | 11/2013 | Phogat et al. | |
| 8,981,057 B2 | 3/2015 | Sanders | |
| 2004/0049150 A1 | 3/2004 | Dalton et al. | |
| 2005/0106177 A1 | 5/2005 | Sodroski et al. | |
| 2010/0204120 A1 | 8/2010 | Jiang et al. | |
| 2012/0100150 A1 | 4/2012 | Jiang et al. | |
| 2012/0269840 A1* | 10/2012 | Barnett ............... | C07K 14/005 424/188.1 |
| 2013/0266611 A1 | 10/2013 | Rabinovich et al. | |

FOREIGN PATENT DOCUMENTS

| | | |
|---|---|---|
| EP | 2873423 A2 | 5/2015 |
| WO | 2008/095927 A1 | 8/2008 |

OTHER PUBLICATIONS

Chakrabarti et al., J. Virol., 2013, 87: 13239-13251.*
Beddows et al., . Virol., 2005, 79: 8812-8827.*
Khayat et al., J. Virol., 2013, 87: 9865-9872.*
Kwong, P. D., and Mascola, J. R. (2012) Human antibodies that neutralize HIV-1: identification, structures, and B cell ontogenies. Immunity 37, 412-425.
Mascola, J. R., and Nabel, G. J. (2001) Vaccines for the prevention of HIV-1 disease. Curr Opin Immunol 13, 489-495.
Wyatt, R., and Sodroski, J. (1998) The HIV-1 envelope glycoproteins: fusogens, antigens, and immunogens. Science 280, 1884-1888.
Ward, A. B., and Wilson, I. A. (2015) Insights into the trimeric HIV-1 envelope glycoprotein structure. Trends Biochem Sci.
Wilen, C. B., Tilton, J. C., and Doms, R. W. (2012) Molecular mechanisms of HIV entry. Adv Exp Med Biol 726, 223-242.
Arthos, J., Cicala, C., Martinelli, E., Macleod, K., Van Ryk, D., Wei, D., Xiao, Z., Veenstra, T. D., Conrad, T. P., Lempicki, R. A., McLaughlin, S., Pascuccio, M., Gopaul, R., McNally, J., Cruz, C. C., Censoplano, N., Chung, E., Reitano, K. N., Kottilil, S., Goode, D. J., and Fauci, A. S. (2008) HIV-1 envelope protein binds to and signals through integrin alpha4beta7, the gut mucosal homing receptor for peripheral T cells. Nat Immunol 9, 301-309.
Cicala, C., Arthos, J., and Fauci, A. S. (2011) HIV-1 envelope, integrins and co-receptor use in mucosal transmission of HIV. J Transl Med 9 Suppl 1, S2.

(Continued)

*Primary Examiner* — Ileana Popa
(74) *Attorney, Agent, or Firm* — Ajay A. Jagtiani; Miles & Stockbridge P.C.

(57) ABSTRACT

An approach of producing recombinant trimers that mimic native HIV-1 envelope trimers is developed. A recombinant protein forming the recombinant trimers encompasses a recombinant HIV-1 gp140 fused to a tag through a linker at C-terminus of the recombinant HIV-1 gp140. The linker is sufficiently long so that the tag is accessible for binding by a binding molecule bound on a solid matrix. After expressed in a cell, the recombinant protein is secreted into the culture medium and assembles into recombinant trimers therein. The recombinant trimers may be directly purified from the culture medium. Cleaved and uncleaved trimers from different clade viruses are produced.

46 Claims, 32 Drawing Sheets

(56) References Cited

OTHER PUBLICATIONS

Dalgleish, A. G., Beverley, P. C., Clapham, P. R., Crawford, D. H., Greaves, M. F., and Weiss, R. A. (1984) The CD4 (T4) antigen is an essential component of the receptor for the AIDS retrovirus. Nature 312, 763-767.

McDougal, J. S., Nicholson, J. K., Cross, G. D., Cort, S. P., Kennedy, M. S., and Mawle, A. C. (1986) Binding of the human retrovirus HTLV-III/LAV/ARV/HIV to the CD4 (T4) molecule: conformation dependence, epitope mapping, antibody inhibition, and potential for idiotypic mimicry. J Immunol 137, 2937-2944.

Klatzmann, D., Champagne, E., Chamaret, S., Gruest, J., Guetard, D., Hercend, T., Gluckman, J. C., and Montagnier, L. (1984) T-lymphocyte T4 molecule behaves as the receptor for human retrovirus LAV. Nature 312, 767-768.

Alkhatib, G., Combadiere, C., Broder, C. C., Feng, Y., Kennedy, P. E., Murphy, P. M., and Berger, E. A. (1996) CC CKR5: a Rantes, MIP-1alpha, MIP-1beta receptor as a fusion cofactor for macrophage-tropic HIV-1. Science 272, 1955-1958.

Feng, Y., Broder, C. C., Kennedy, P. E., and Berger, E. A. (1996) HIV-1 entry cofactor: functional cDNA cloning of a seven-transmembrane, G protein-coupled receptor. Science 272, 872-877.

Lederman, M. M., Penn-Nicholson, A., Cho, M., and Mosier, D. (2006) Biology of CCR5 and its role in HIV infection and treatment. JAMA 296, 815-826.

Furuta, R. A., Wild, C. T., Weng, Y., and Weiss, C. D. (1998) Capture of an early fusion-active conformation of HIV-1 gp41. Nat Struct Biol 5, 276-279.

Gallo, S. A., Finnegan, C. M., Viard, M., Raviv, Y., Dimitrov, A., Rawat, S. S., Puri, A., Durell, S., and Blumenthal, R. (2003) The HIV Env-mediated fusion reaction. Biochim Biophys Acta 1614, 36-50.

Roben, P., Moore, J. P., Thali, M., Sodroski, J., Barbas, C. F., 3rd, and Burton, D. R. (1994) Recognition properties of a panel of human recombinant Fab fragments to the CD4 binding site of gp120 that show differing abilities to neutralize human immunodeficiency virus type 1. J Virol 68, 4821-4828.

Wu, X., Yang, Z. Y., Li, Y., Hogerkorp, C. M., Schief, W. R., Seaman, M. S., Zhou, T., Schmidt, S. D., Wu, L., Xu, L., Longo, N. S., McKee, K., O'Dell, S., Louder, M. K., Wycuff, D. L., Feng, Y., Nason, M., Doria-Rose, N., Connors, M., Kwong, P. D., Roederer, M., Wyatt, R. T., Nabel, G. J., and Mascola, J. R. (2010) Rational design of envelope identifies broadly neutralizing human monoclonal antibodies to HIV-1. Science 329, 856-861.

Zwick, M. B., Jensen, R., Church, S., Wang, M., Stiegler, G., Kunert, R., Katinger, H., and Burton, D. R. (2005) Anti-human immunodeficiency virus type 1 (HIV-1) antibodies 2F5 and 4E10 require surprisingly few crucial residues in the membrane-proximal external region of glycoprotein gp41 to neutralize HIV-1. J Virol 79, 1252-1261.

Walker, L. M., Phogat, S. K., Chan-Hui, P. Y., Wagner, D., Phung, P., Goss, J. L., Wrin, T., Simek, M. D., Fling, S., Mitcham, J. L., Lehrman, J. K., Priddy, F. H., Olsen, O. A., Frey, S. M., Hammond, P. W., Protocol, G. P. I., Kaminsky, S., Zamb, T., Moyle, M., Koff, W. C., Poignard, P., and Burton, D. R. (2009) Broad and potent neutralizing antibodies from an African donor reveal a new HIV-1 vaccine target. Science 326, 285-289.

Benjelloun, F., Lawrence, P., Verrier, B., Genin, C., and Paul, S. (2012) Role of human immunodeficiency virus type 1 envelope structure in the induction of broadly neutralizing antibodies. J Virol 86, 13152-13163.

Yu, L., and Guan, Y. (2014) Immunologic Basis for Long HCDR3s in Broadly Neutralizing Antibodies Against HIV-1. Front Immunol 5, 250.

Esparza, J. (2013) A brief history of the global effort to develop a preventive HIV vaccine. Vaccine 31, 3502-3518.

Chakrabarti, B. K., Feng, Y., Sharma, S. K., McKee, K., Karlsson Hedestam, G. B., Labranche, C. C., Montefiori, D. C., Mascola, J. R., and Wyatt, R. T. (2013) Robust neutralizing antibodies elicited by HIV-1 JRFL envelope glycoprotein trimers in nonhuman primates. J Virol 87, 13239-13251.

Kovacs, J. M., Nkolola, J. P., Peng, H., Cheung, A., Perry, J., Miller, C. A., Seaman, M. S., Barouch, D. H., and Chen, B. (2012) HIV-1 envelope trimer elicits more potent neutralizing antibody responses than monomeric gp120. Proc Natl Acad Sci U S A 109, 12111-12116.

Nkolola, J. P., Cheung, A., Perry, J. R., Carter, D., Reed, S., Schuitemaker, H., Pau, M. G., Seaman, M. S., Chen, B., and Barouch, D. H. (2014) Comparison of multiple adjuvants on the stability and immunogenicity of a clade C HIV-1 gp140 timer. Vaccine 32, 2109-2116.

Ringe, R. P., Sanders, R. W., Yasmeen, A., Kim, H. J., Lee, J. H., Cupo, A., Korzun, J., Derking, R., van Montfort, T., Julien, J. P., Wilson, I. A., Klasse, P. J., Ward, A. B., and Moore, J. P. (2013) Cleavage strongly influences whether soluble HIV-1 envelope glycoprotein trimers adopt a native-like conformation. Proc Natl Acad Sci U S A 110, 18256-18261.

Liao, H. X., Lynch, R., Zhou, T., Gao, F., Alam, S. M., Boyd, S. D., Fire, A. Z., Roskin, K. M., Schramm, C. A., Zhang, Z., Zhu, J., Shapiro, L., Program, N. C. S., Mullikin, J. C., Gnanakaran, S., Hraber, P., Wiehe, K., Kelsoe, G., Yang, G., Xia, S. M., Montefiori, D. C., Parks, R., Lloyd, K. E., Scearce, R. M., Soderberg, K. A., Cohen, M., Kamanga, G., Louder, M. K., Tran, L. M., Chen, Y., Cai, F., Chen, S., Moquin, S., Du, X., Joyce, M. G., Srivatsan, S., Zhang, B., Zheng, A., Shaw, G. M., Hahn, B. H., Kepler, T. B., Korber, B. T., Kwong, P. D., Mascola, J. R., and Haynes, B. F. Sanders, R. W., Derking, R., Cupo, A., Julien, J. P., Yasmeen, A., de Val, N., Kim, H. J., Blattner, C., de la Pena, A. T., Korzun, J., Golabek, M., de Los Reyes, K., Ketas, T. J., van Gils, M. J., King, C. R., Wilson, I. A., Ward, A. B., Klasse, P. J., and Moore, J. P. (2013) A nextgeneration cleaved, soluble HIV-1 Env Trimer, BG505 SOSIP.664 gp140, expresses multiple epitopes for broadly neutralizing but not non-neutralizing antibodies. PLoS Pathog 9, e1003618.

Julien, J. P., Cupo, A., Sok, D., Stanfield, R. L., Lyumkis, D., Deller, M. C., Klasse, P. J., Burton, D. R., Sanders, R. W., Moore, J. P., Ward, A. B., and Wilson, I. A. (2013) Crystal structure of a soluble cleaved HIV-1 envelope trimer. Science 342, 1477-1483.

Lyumkis, D., Julien, J. P., de Val, N., Cupo, A., Potter, C. S., Klasse, P. J., Burton, D. R., Sanders, R. W., Moore, J. P., Carragher, B., Wilson, I. A., and Ward, A. B. (2013) Cryo-EM structure of a fully glycosylated soluble cleaved HIV-1 envelope trimer. Science 342, 1484-1490.

Guenaga, J., de Val, N., Tran, K., Feng, Y., Satchwell, K., Ward, A. B., and Wyatt, R. T. (2015) Well-Ordered Trimeric HIV-1 Subtype B and C Soluble Spike Mimetics Generated by Negative Selection Display Native-like Properties. PLoS Pathog 11, e1004570.

Gao, G., Wieczorek, L., Peachman, K. K., Polonis, V. R., Alving, C. R., Rao, M., and Rao, V. B. (2013) Designing a soluble near full-length HIV-1 gp41 trimer. J Biol Chem 288, 234-246.

Tao, P., Mahalingam, M., Marasa, B. S., Zhang, Z., Chopra, A. K., and Rao, V. B. (2013) In vitro and in vivo delivery of genes and proteins using the bacteriophage T4 DNA packaging machine. Proc Natl Acad Sci U S A 110, 5846-5851.

Sathaliyawala, T., Rao, M., Maclean, D. M., Birx, D. L., Alving, C. R., and Rao, V. B. (2006) Assembly of human immunodeficiency virus (HIV) antigens on bacteriophage T4: a novel in vitro approach to construct multicomponent HIV vaccines. J Virol 80, 7688-7698.

Liu, J., Bartesaghi, A., Borgnia, M. J., Sapiro, G., and Subramaniam, S. (2008) Molecular architecture of native HIV-1 gp120 trimers. Nature 455, 109-113.

Buchacher, A., Predl, R., Strutzenberger, K., Steinfellner, W., Trkola, A., Purtscher, M., Gruber, G., Tauer, C., Steindl, F., Jungbauer, A., and et al. (1994) Generation of human monoclonal antibodies against HIV-1 proteins; electrofusion and Epstein-Barr virus transformation for peripheral blood lymphocyte immortalization. AIDS Res Hum Retroviruses 10, 359-369.

Trkola, A., Purtscher, M., Muster, T., Ballaun, C., Buchacher, A., Sullivan, N., Srinivasan, K., Sodroski, J., Moore, J. P., and Katinger, H. (1996) Human monoclonal antibody 2G12 defines a distinctive neutralization epitope on the gp120 glycoprotein of human immunodeficiency virus type 1. J Virol 70, 1100-1108.

(56) References Cited

OTHER PUBLICATIONS

Mascola, J. R., Lewis, M. G., Stiegler, G., Harris, D., VanCott, T. C., Hayes, D., Louder, M. K., Brown, C. R., Sapan, C. V., Frankel, S. S., Lu, Y., Robb, M. L., Katinger, H., and Birx, D. L. (1999) Protection of Macaques against pathogenic simian/human immunodeficiency virus 89.6PD by passive transfer of neutralizing antibodies. J Virol 73, 4009-4018.

Etemad-Moghadam, B., Sun, Y., Nicholson, E. K., Karlsson, G. B., Schenten, D., and Sodroski, J. (1999) Determinants of neutralization resistance in the envelope glycoproteins of a simianhuman immunodeficiency virus passaged in vivo. J Virol 73, 8873-8879.

Crawford, J. M., Earl, P. L., Moss, B., Reimann, K. A., Wyand, M. S., Manson, K. H., Bilska, M., Zhou, J. T., Pauza, C. D., Parren, P. W., Burton, D. R., Sodroski, J. G., Letvin, N. L., and Montefiori, D. C. (1999) Characterization of primary isolate-like variants of simian-human immunodeficiency virus. J Virol 73, 10199-10207.

Walker, L. M., Huber, M., Doores, K. J., Falkowska, E., Pejchal, R., Julien, J. P., Wang, S. K., Ramos, A., Chan-Hui, P. Y., Moyle, M., Mitcham, J. L., Hammond, P. W., Olsen, O. A., Phung, P., Fling, S., Wong, C. H., Phogat, S., Wrin, T., Simek, M. D., Protocol, G. P. I., Koff, W. C., Wilson, I. A., Burton, D. R., and Poignard, P. (2011) Broad neutralization coverage of HIV by multiple highly potent antibodies. Nature 477, 466-470.

Cavacini, L. A., Emes, C. L., Wisnewski, A. V., Power, J., Lewis, G., Montefiori, D., and Posner, M. R. (1998) Functional and molecular characterization of human monoclonal antibody reactive with the immunodominant region of HIV type 1 glycoprotein 41. AIDS Res Hum Retroviruses 14, 1271-1280.

Posner, M. R., Elboim, H., and Santos, D. (1987) The construction and use of a human-mouse myeloma analogue suitable for the routine production of hybridomas secreting human monoclonal antibodies. Hybridoma 6, 611-625.

Posner, M. R., Hideshima, T., Cannon, T., Mukherjee, M., Mayer, K. H., and Byrn, R. A. (1991) An IgG human monoclonal antibody that reacts with HIV-1/GP120, inhibits virus binding to cells, and neutralizes infection. J Immunol 146, 4325-4332.

Posner, M. R., Cavacini, L. A., Emes, C. L., Power, J., and Byrn, R. (1993) Neutralization of HIV-1 by F105, a human monoclonal antibody to the CD4 binding site of gp120. J Acquir Immune Defic Syndr 6, 7-14.

Cavacini, L. A., Emes, C. L., Power, J., Underdahl, J., Goldstein, R., Mayer, K., and Posner, M. R. (1993) Loss of serum antibodies to a conformational epitope of HIV-1/gp120 identified by a human monoclonal antibody is associated with disease progression. J Acquir Immune Defic Syndr 6, 1093-1102.

Falkowska, E., Le, K. M., Ramos, A., Doores, K. J., Lee, J. H., Blattner, C., Ramirez, A., Derking, R., van Gils, M. J., Liang, C. H., McBride, R., von Bredow, B., Shivatare, S. S., Wu, C. Y., Chan-Hui, P. Y., Liu, Y., Feizi, T., Zwick, M. B., Koff, W. C., Seaman, M. S., Swiderek, K., Moore, J. P., Evans, D., Paulson, J. C., Wong, C. H., Ward, A. B., Wilson, I. A., Sanders, R. W., Poignard, P., and Burton, D. R. (2014) Broadly neutralizing HIV antibodies define a glycandependent epitope on the prelusion conformation of gp41 on cleaved envelope trimers. Immunity 40, 657-668.

Yang, X., Lee, J., Mahony, E. M., Kwong, P. D., Wyatt, R., and Sodroski, J. (2002) Highly stable trimers formed by human immunodeficiency virus type 1 envelope glycoproteins fused with the trimeric motif of T4 bacteriophage fibritin. J Virol 76, 4634-4642.

Binley, J. M., Sanders, R. W., Clas, B., Schuelke, N., Master, A., Guo, Y., Kajumo, F., Anselma, D. J., Maddon, P. J., Olson, W. C., and Moore, J. P. (2000) a recombinant human immunodeficiency virus type 1 envelope glycoprotein complex stabilized by an intermolecular disulfide bond between the gp120 and gp41 subunits is an antigenic mimic of the trimeric virionassociated structure. J Virol 74, 627-643.

Sanders, R. W., Vesanen, M., Schuelke, N., Master, A., Schiffner, L., Kalyanaraman, R., Paluch, M., Berkhout, B., Maddon, P. J., Olson, W. C., Lu, M., and Moore, J. P. (2002) Stabilization of the soluble, cleaved, trimeric form of the envelope glycoprotein complex of human immunodeficiency virus type 1. J Virol 76, 8875-8889.

Dey, A. K., David, K. B., Klasse, P. J., and Moore, J. P. (2007) Specific amino acids in the Nterminus of the gp41 ectodomain contribute to the stabilization of a soluble, cleaved gp140 envelope glycoprotein from human immunodeficiency virus type 1. Virology 360, 199-208.

Binley, J. M., Sanders, R. W., Master, A., Cayanan, C. S., Wiley, C. L., Schiffner, L., Travis, B., Kuhmann, S., Burton, D. R., Hu, S. L., Olson, W. C., and Moore, J. P. (2002) Enhancing the proteolytic maturation of human immunodeficiency virus type 1 envelope glycoproteins. J Virol 76, 2606-2616.

Hoffenberg, S., Powell, R., Carpov, A., Wagner, D., Wilson, A., Kosakovsky Pond, S., Lindsay, R., Arendt, H., Destefano, J., Phogat, S., Poignard, P., Fling, S. P., Simek, M., Labranche, C., Montefiori, D., Wrin, T., Phung, P., Burton, D., Koff, W., King, C. R., Parks, C. L., and Caulfield, M. J. (2013) Identification of an HIV-1 clade A envelope that exhibits broad antigenicity and neutralization sensitivity and elicits antibodies targeting three distinct epitopes. J Virol 87, 5372-5383.

Kong, L., Lee, J. H., Doores, K. J., Murin, C. D., Julien, J. P., McBride, R., Liu, Y., Marozsan, A., Cupo, A., Klasse, P. J., Hoffenberg, S., Caulfield, M., King, C. R., Hua, Y., Le, K. M., Khayat, R., Deller, M. C., Clayton, T., Tien, H., Feizi, T., Sanders, R. W., Paulson, J. C., Moore, J. P., Stanfield, R. L., Burton, D. R., Ward, A. B., and Wilson, I. A. (2013) Supersite of immune vulnerability on the glycosylated face of HIV-1 envelope glycoprotein gp120. Nat Struct Mol Biol 20, 796-803.

Higuchi, R., Krummel, B., and Saiki, R. K. (1988) A general method of in vitro preparation and specific mutagenesis of DNA fragments: study of protein and DNA interactions. Nucleic Acids Res 16, 7351-7367.

Stemmer, W. P., Crameri, A., Ha, K. D., Brennan, T. M., and Heyneker, H. L. (1995) Single-step assembly of a gene and entire plasmid from large numbers of oligodeoxyribonucleotides. Gene 164, 49-53.

Reeves, P. J., Kim, J. M., and Khorana, H. G. (2002) Structure and function in rhodopsin: a tetracycline-inducible system in stable mammalian cell lines for high-level expression of opsin mutants. Proc Natl Acad Sci U S A 99, 13413-13418.

Tang, G. Peng, L., Baldwin, P. R., Mann, D. S., Jiang, W., Rees, I., and Ludtke, S. J. (2007) EMAN2: an extensible image processing suite for electron microscopy. J Struct Biol 157, 38-46.

Tran, K., Poulsen, C., Guenaga, J., de Val, N., Wilson, R., Sundling, C., Li, Y., Stanfield, R. L., Wilson, I. A., Ward, A. B., Karlsson Hedestam, G. B., and Wyatt, R. T. (2014) Vaccine-elicited primate antibodies use a distinct approach to the HIV-1 primary receptor binding site informing vaccine redesign. Proc Natl Acad Sci U S A 111, E738-747.

Georgiev, I. S., Joyce, M. G., Yang, Y., Sastry, M., Zhang, B., Baxa, U., Chen, R. E., Druz, A., Lees, C. R., Narpala, S., Schon, A., Van Galen, J., Chuang, G. Y., Gorman, J., Hamed, A., Pancera, M., Stewart-Jones, G. B., Cheng, C., Freire, E., McDermott, A. B., Mascola, J. R., and Kwong, P. D. (2015) Single-chain soluble BG505.SOSIP gp140 trimers as structural and antigenic mimics of mature closed HIV-1 Env. J Virol.

Julien, J. P., Sok, D., Khayat, R., Lee, J. H., Doores, K. J., Walker, L. M., Ramos, A., Diwanji, D. C., Pejchal, R., Cupo, A., Katpally, U., Depetris, R. S., Stanfield, R. L., McBride, R., Marozsan, A. J., Paulson, J. C., Sanders, R. W., Moore, J. P., Burton, D. R., Poignard, P., Ward, A. B., and Wilson, I. A. (2013) Broadly neutralizing antibody PGT121 allosterically modulates CD4 binding via recognition of the HIV-1 gp120 V3 base and multiple surrounding glycans. PLoS Pathog 9, e1003342.

Depetris, R. S., Julien, J. P., Khayat, R., Lee, J. H., Pejchal, R., Katpally, U., Cocco, N., Kachare, M., Massi, E., David, K. B., Cupo, A., Marozsan, A. J., Olson, W. C., Ward, A. B., Wilson, I. A., Sanders, R. W., and Moore, J. P. (2012) Partial enzymatic deglycosylation preserves the structure of cleaved recombinant HIV-1 envelope glycoprotein trimers. J Biol Chem 287, 24239-24254.

Guttman, M., Garcia, N. K., Cupo, A., Matsui, T., Julien, J. P., Sanders, R. W., Wilson, I. A., Moore, J. P., and Lee, K. K. (2014) CD4-induced activation in a soluble HIV-1 Env trimer. Structure 22, 974-984.

(56) References Cited

OTHER PUBLICATIONS

Sanders, R. W., Venturi, M., Schiffner, L., Kalyanaraman, R., Katinger, H., Lloyd, K. O., Kwong, P. D., and Moore, J. P. (2002) The mannose-dependent epitope for neutralizing antibody 2G12 on human immunodeficiency virus type 1 glycoprotein gp120. J Virol 76, 7293-7305.

Murin, C. D., Julien, J. P., Sok, D., Stanfield, R. L., Khayat, R., Cupo, A., Moore, J. P., Burton, D. R., Wilson, I. A., and Ward, A. B. (2014) Structure of 2G12 Fab2 in complex with soluble and fully glycosylated HIV-1 Env by negative-stain single-particle electron microscopy. J Virol 88, 10177-10188.

Yasmeen, A., Ringe, R., Derking, R., Cupo, A., Julien, J. P., Burton, D. R., Ward, A. B., Wilson, I. A., Sanders, R. W., Moore, J. P., and Klasse, P. J. (2014) Differential binding of neutralizing and non-neutralizing antibodies to native-like soluble HIV-1 Env trimers, uncleaved Env proteins, and monomeric subunits. Retrovirology 11, 41.

Pancera, M., and Wyatt, R. (2005) Selective recognition of oligomeric HIV-1 primary isolate envelope glycoproteins by potently neutralizing ligands requires efficient precursor cleavage. Virology 332, 145-156.

Blattner, C., Lee, J. H., Sliepen, K., Derking, R., Falkowska, E., de la Pena, A. T., Cupo, A., Julien, J. P., van Gils, M., Lee, P. S., Peng, W., Paulson, J. C., Poignard, P., Burton, D. R., Moore, J. P., Sanders, R. W., Wilson, I. A., and Ward, A. B. (2014) Structural delineation of a quaternary, cleavage-dependent epitope at the gp41-gp120 interface on intact HIV-1 Env trimers. Immunity 40, 669-680.

Pancera, M., Zhou, T., Druz, A., Georgiev, I. S., Soto, C., Gorman, J., Huang, J., Acharya, P., Chuang, G. Y., Ofek, G., Stewart-Jones, G. B., Stuckey, J., Bailer, R. T., Joyce, M. G., Louder, M. K., Tumba, N., Yang, Y., Zhang, B., Cohen, M. S., Haynes, B. F., Mascola, J. R., Morris, L., Munro, J. B., Blanchard, S. C., Mothes, W., Connors, M., and Kwong, P. D. (2014) Structure and immune recognition of trimeric pre-fusion HIV-1 Env. Nature 514, 455-461.

McLellan, J. S., Pancera, M., Carrico, C., Gorman, J., Julien, J. P., Khayat, R., Louder, R., Pejchal, R., Sastry, M., Dai, K., O'Dell, S., Patel, N., Shahzad-ul-Hussan, S., Yang, Y., Zhang, B., Zhou, T., Zhu, J., Boyington, J. C., Chuang, G. Y., Diwanji, D., Georgiev, I., Kwon, Y. D., Lee, D., Louder, M. K., Moquin, S., Schmidt, S. D., Yang, Z. Y., Bonsignori, M., Crump, J. A., Kapiga, S. H., Sam, N. E., Haynes, B. F., Burton, D. R., Koff, W. C., Walker, L. M., Phogat, S., Wyatt, R., Orwenyo, J., Wang, L. X., Arthos, J., Bewley, C. A., Mascola, J. R., Nabel, G. J., Schief, W. R., Ward, A. B., Julien, J. P., Lee, J. H., Cupo, A., Murin, C. D., Derking, R., Hoffenberg, S., Caulfield, M. J., King, C. R., Marozsan, A. J., Klasse, P. J., Sanders, R. W., Moore, J. P., Wilson, I. A., and Ward, A. B. (2013) Asymmetric recognition of the HIV-1 trimer by broadly neutralizing antibody PG9. Proc Natl Acad Sci U S A 110, 4351-4356.

Thali, M., Furman, C., Ho, D. D., Robinson, J., Tilley, S., Pinter, A., and Sodroski, J. (1992) Discontinuous, conserved neutralization epitopes overlapping the CD4-binding region of human immunodeficiency virus type 1 gp120 envelope glycoprotein. J Virol 66, 5635-5641.

Chen, L., Kwon, Y. D., Zhou, T., Wu, X., O'Dell, S., Cavacini, L., Hessell, A. J., Pancera, M., Tang, M., Xu, L., Yang, Z. Y., Zhang, M. Y., Arthos, J., Burton, D. R., Dimitrov, D. S., Nabel, G. J., Posner, M. R., Sodroski, J., Wyatt, R., Mascola, J. R., and Kwong, P. D. (2009) Structural basis of immune evasion at the site of CD4 attachment on HIV-1 gp120. Science 326, 1123-1127.

Cavacini, L. A., Duval, M., Robinson, J., and Posner, M. R. (2002) Interactions of human antibodies, epitope exposure, antibody binding and neutralization of primary isolate HIV-1 virions. AIDS 16, 2409-2417.

Pugach, P., Ozorowski, G., Cupo, A., Ringe, R., Yasmeen, A., de Val, N., Derking, R., Kim, H. J., Korzun, J., Golabek, M., de Los Reyes, K., Ketas, T. J., Julien, J. P., Burton, D. R., Wilson, I. A., Sanders, R. W., Klasse, P. J., Ward, A. B., and Moore, J. P. (2015) A native-like SOSIP.664 trimer based on a HIV-1 subtype B env gene. J Virol.

Checkley, M. A., Luttge, B. G., and Freed, E. O. (2011) HIV-1 envelope glycoprotein biosynthesis, trafficking, and incorporation. J Mol Biol 410, 582-608.

Sun, Z. Y., Oh, K. J., Kim, M., Yu, J., Brusic, V., Song, L., Qiao, Z., Wang, J. H., Wagner, G., and Reinherz, E. L. (2008) HIV-1 broadly neutralizing antibody extracts its epitope from a kinked gp41 ectodomain region on the viral membrane. Immunity 28, 52-63.

Bartesaghi, A., Merk, A., Borgnia, M. J., Milne, J. L., and Subramaniam, S. (2013) Prefusion structure of trimeric HIV-1 envelope glycoprotein determined by cryo-electron microscopy. Nat Struct Mol Biol 20, 1352-1357.

Harris, A., Borgnia, M. J., Shi, D., Bartesaghi, A., He, H., Pejchal, R., Kang, Y. K., Depetris, R., Marozsan, A. J., Sanders, R. W., Klasse, P. J., Milne, J. L., Wilson, I. A., Olson, W. C., Moore, J. P., and Subramaniam, S. (2011) Trimeric HIV-1 glycoprotein gp140 immunogens and native HIV-1 envelope glycoproteins display the same closed and open quaternary molecular architectures. Proc Natl Acad Sci U S A 108, 11440-11445.

Frey et al., "A fusion-intermediate state of HIV-1 gp41 targeted by broadly neutralizing antibodies", PNAS, vol. 105, No. 10. pp. 3739-3744 (2008).

He et al., "WSSV ie I promoter is more efficient than CMV promoter to express H5 hemagglutinin from influenza virus in baculovirus as a chicken vaccine", BMC Microbiology, 8:23, pp. 1-10 (2008).

Invitrogen, pFastBacTM/HBM-TOPO expression vector datasheet, retrieved 2016.

Kovacs et al., "Stable, uncleaved HIV-1 envelope glycoprotein gp140 forms a tightly folded trimer with a native-like structure", PNAS, vol. 111, No. 52, pp. 18542-18547 (2014).

Office Action received in U.S. Appl. No. 14/806,739 dated Aug. 15, 2016.

Office Action received in U.S. Appl. No. 14/806,751 dated Oct. 7, 2016.

International Search Report received in PCT Application No. PCT/IB2016/054176 dated Oct. 10, 2016.

International Search Report received in PCT Application No. PCT/IB2016/054207 dated Oct. 10, 2016.

International Search Report received in PCT Application No. PCT/IB2016/054250 dated Oct. 10, 2016.

Barouch, "Challenges in the development of an HIV-1 vaccine", Nature, vol. 455, pp. 613-619 (2008).

Kwong et al., "Rational Design of Vaccines to Elicit Broadly Neutralizing Antibodies to HIV-1", Cold Spring Perspect Med., 1:a007278, pp. 1-16 (2011).

Lewis et al., "Antibody persistence and T-cell balance: Two key factors confronting HIV vaccine development", PNAS, vol. 111, No. 44, pp. 15614-15621 (2004).

Walker et al., "Toward an AIDS Vaccine", Science, vol. 320, pp. 760-764 (2008).

West et al., "Structural Insights on the Role of Antibodies in HIV-1 Vaccine and Therapy", Cell, vol. 156, pp. 633-648 (2014).

Zolla-Pazner, "A critical question for HIV vaccine development: Which antibodies to induce?", Science, vol. 345, Issue 6193, pp. 167-169 (2014).

Alsalmi et al., "A new approach to produce HIV-1 envelope trimers,both cleavage and proper glycosylation are essential to generate authentic trimers", The Journal of Biological Chemistry, vol. 290, No. 32, pp. 19780-19795, (2015).

NCBI GenBank Accession No. AAB05604 (Aug. 2, 1996).

NCBI GenBank Accession No. ABA61516 (Jan. 3, 2006).

NCBI GenBank Accession No. AGI21277 (Sep. 5, 2013).

Sanders et al., "A next-generation cleaved, soluble HIV-1 env trimer, BG505 SOSIP.664 gp140, expresses multiple epitopes for broadly neutralizing but not non-neutralizing antibodies", PLOS Pathogens, vol. 9, Issue 9, Article e1003618, internal pp. 1-20 (2013).

Search Report and Written Opinion received in PCT Application No. PCT/IB2016/054260 dated Oct. 21, 2016.

Search Report and Written Opinion received in PCT Application No. PCT/IB2016/054292 dated Oct. 24, 2016.

NCBI, GenBank Accession No. AEL01134.1 (Aug. 3, 2011).

(56) References Cited

OTHER PUBLICATIONS

Sharma et al., "Cleavage-independent HIV-1 Env trimers engineered as soluble native spike mimetics for vaccine design", Cell Reports, vol. 11, No. 4, pp. 539-550 (2015).
Frey et al., "A fusion-intermediate state of HIV-1 gp41 targeted by broadly neutralizing antibodies", PNAS; vol. 105; No. 10; pp. 3739-3744.
Sanders et al., "A Next-Generation Cleaved, Soluble HIV-1 Env Trimer, BG505 SOSIP.664 gp140, Expresses Multiple Epitopes for Broadly Neutralizing but Not Non-Neutralizing Antibodies", PLOS Pathogens; vol. 9; Issue 9; e1003618 (pp. 1-20) (2013).
Office Action received in U.S. Appl. No. 14/806,727 dated Feb. 13, 2017.
Office Action received in U.S. Appl. No. 14/806,751 dated Feb. 28, 2017.
Chen et al., "Fusion protein linkers: Property, design and functionality", Advanced Drug Delivery Reviews, 65, pp. 1357-1369 (2013).
Frey et al., "A fusion-intermediate state of HIV-1 gp41 targeted by broadly neutralizing antibodies", PNAS, vol. 105, No. 10, pp. 3739-3744 (2008).
Sanders et al., "A Next-Generation Cleaved, Soluble HIV-1 Env Trimer, BG505 SOSIP.664 gp140, Express Multiple Epitopes for Broadly Neutralizing but Not Non-Neutralizing Antibodies", PLOS Pathogens, vol. 9, Issue 9, e1003618 pp. 1-20, (2013).
Schmidt et al., "Development of the Twin-Strep-tag and its application for purification of recombinant proteins from cell culture supernatants", Proteins and Purification, 92, pp. 54-61 (2013).
Office Action received in U.S. Appl. No. 14/806,735 dated Feb. 27, 2017.
Office Action received in U.S. Appl. No. 14/806,727 dated Aug. 22, 2017.
Office Action received in U.S. Appl. No. 14/806,735 dated Aug. 23, 2017.
AlSalmi et al., "A New Approach to Produce HIV-1 Envelope Trimers", The Journal of Biological Chemistry, vol. 290, No. 32, pp. 19780-19795 (2015).
Office Action received in U.S. Appl. No. 15/817,761 dated Dec. 28, 2017.
Office Action received in U.S. Appl. No. 14/806,751 dated Sep. 19, 2017.

\* cited by examiner

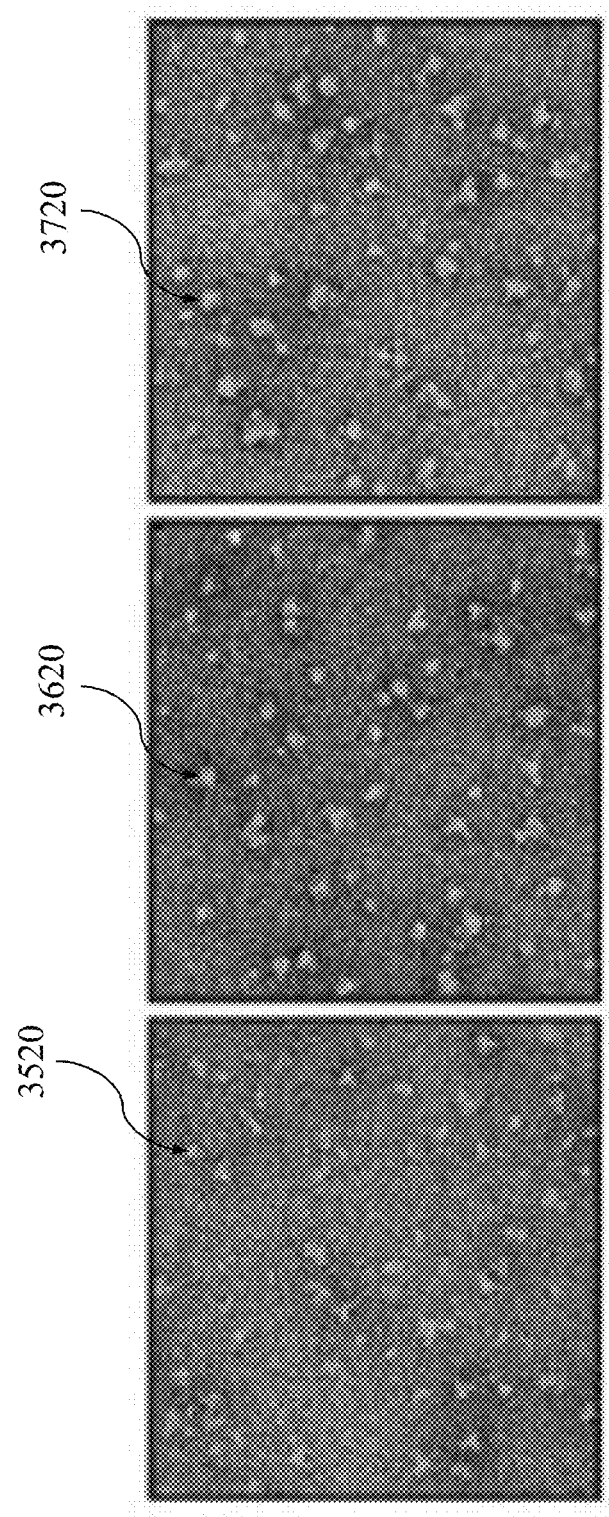

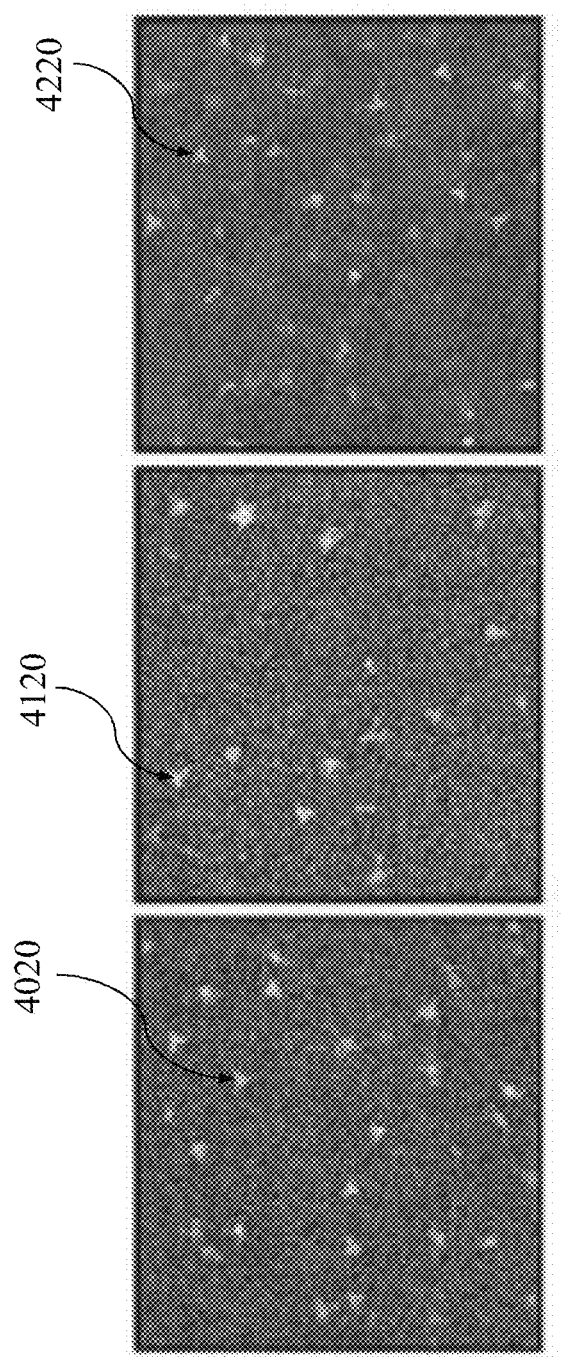

SEQUENCE LISTING

<160> NUMBER OF SEQ ID NOS: 13

<210> SEQ ID NO 1
<211> LENGTH: 27
<212> TYPE: PRT
<213> ORGANISM: Artificial Sequence
<220> FEATURE:
<223> OTHER INFORMATION: Artificial foldon protein sequence derived from bacteriophage T4.

```
<400> SEQUENCE: 1

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 2
<211> LENGTH: 8
<212> TYPE: PRT
<213> ORGANISM: Artificial Sequence
<220> FEATURE:
<223> OTHER INFORMATION: Artifical Strep-Tag II protein sequence

<400> SEQUENCE: 2

Trp Ser His Pro Gln Phe Glu Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Artificial octa-histidine tag protein sequence

<400> SEQUENCE: 3

His His His His His His His His
1               5

<210> SEQ ID NO 4
<211> LENGTH: 6
<212> TYPE: PRT
<213> ORGANISM: Artificial Sequence
<220> FEATURE:
<223> OTHER INFORMATION: Artificial hexa-histidine tag protein sequence

<400> SEQUENCE: 4

His His His His His His
1               5

<210> SEQ ID NO 5
<211> LENGTH: 23
<212> TYPE: PRT
<213> ORGANISM: Artificial Sequence
<220> FEATURE:
<223> OTHER INFORMATION: Artificial peptide linker protein sequence

<400> SEQUENCE: 5

Ala Ala Ala Trp Ser His Pro Gln Phe Glu Lys Gly Gly Gly Ser Gly
1               5                   10                  15

Gly Gly Ser Gly Gly Ser Ala
            20

<210> SEQ ID NO 6
<211> LENGTH: 31
<212> TYPE: PRT
<213> ORGANISM: Artificial Sequence
<220> FEATURE:
<223> OTHER INFORMATION: Artificial peptide linker protein sequence

<400> SEQUENCE: 6

Ala Ala Ala Leu Glu Val Leu Phe Gln Gly Pro Trp Ser His Pro Gln
1               5                   10                  15

Phe Glu Lys Gly Gly Gly Ser Gly Gly Gly Ser Gly Gly Ser Ala
            20                  25                  30
```

-continued

```
<210> SEQ ID NO 7
<211> LENGTH: 35
<212> TYPE: PRT
<213> ORGANISM: Artificial Sequence
<220> FEATURE:
<223> OTHER INFORMATION: Artificial peptide linker protein sequence

<400> SEQUENCE: 7

Ala Ala Ala Gly Gly Gly Ser Gly Gly Gly Ser Gly Gly Ser Ala Trp
 1               5                  10                  15

Ser His Pro Gln Phe Glu Lys Gly Gly Gly Ser Gly Gly Gly Ser Gly
            20                  25                  30

Gly Ser Ala
        35

<210> SEQ ID NO 8
<211> LENGTH: 43
<212> TYPE: PRT
<213> ORGANISM: Artificial Sequence
<220> FEATURE:
<223> OTHER INFORMATION: Artificial peptide linker protein sequence

<400> SEQUENCE: 8

Ala Ala Ala Leu Glu Val Leu Phe Gln Gly Pro Gly Gly Gly Ser Gly
 1               5                  10                  15

Gly Gly Ser Gly Gly Ser Ala Trp Ser His Pro Gln Phe Glu Lys Gly
            20                  25                  30

Gly Gly Ser Gly Gly Gly Ser Gly Gly Ser Ala
        35                  40

<210> SEQ ID NO 9
<211> LENGTH: 27
<212> TYPE: PRT
<213> ORGANISM: Artificial Sequence
<220> FEATURE:
<223> OTHER INFORMATION: Artificial peptide linker protein sequence

<400> SEQUENCE: 9

Ala Ala Ala Leu Glu Val Leu Phe Gln Gly Pro Ala Pro Ala Pro Ala
 1               5                  10                  15

Pro Ala Pro Ala Pro Ala Pro Ala Pro Ala Pro
            20                  25

<210> SEQ ID NO 10
<211> LENGTH: 659
<212> TYPE: PRT
<213> ORGANISM: Artificial Sequence
<220> FEATURE:
<223> OTHER INFORMATION: Artificial protein sequence of Strep-Tagged
      JRFL SOSIP(1-5).R6.664 gp140 comprising an engineered HIV-1 clade
      B JRFL gp140, a peptide linker, and a Strep-Tag.

<400> SEQUENCE: 10

Val Glu Lys Leu Trp Val Thr Val Tyr Tyr Gly Val Pro Val Trp Lys
 1               5                  10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu His Phe Asn
    50                  55                  60

Met Trp Lys Asn Asn Met Val Glu Gln Met Gln Glu Asp Ile Ile Ser
```

-continued

```
            65                  70                  75                  80
Leu Trp Asp Gln Ser Leu Lys Pro Cys Val Lys Leu Thr Pro Leu Cys
                    85                  90                  95
Val Thr Leu Asn Cys Lys Asp Val Asn Ala Thr Asn Thr Thr Asn Asp
                    100                 105                 110
Ser Glu Gly Thr Met Glu Arg Gly Glu Ile Lys Asn Cys Ser Phe Asn
                    115                 120                 125
Ile Thr Thr Ser Ile Arg Asp Glu Val Gln Lys Glu Tyr Ala Leu Phe
                    130                 135                 140
Tyr Lys Leu Asp Val Val Pro Ile Asp Asn Asn Asn Thr Ser Tyr Arg
145                 150                 155                 160
Leu Ile Ser Cys Asp Thr Ser Val Ile Thr Gln Ala Cys Pro Lys Ile
                    165                 170                 175
Ser Phe Glu Pro Ile Pro Ile His Tyr Cys Ala Pro Ala Gly Phe Ala
                    180                 185                 190
Ile Leu Lys Cys Asn Asp Lys Thr Phe Asn Gly Lys Gly Pro Cys Lys
                    195                 200                 205
Asn Val Ser Thr Val Gln Cys Thr His Gly Ile Arg Pro Val Val Ser
                    210                 215                 220
Thr Gln Leu Leu Leu Asn Gly Ser Leu Ala Glu Glu Val Val Ile
225                 230                 235                 240
Arg Ser Asp Asn Phe Thr Asn Asn Ala Lys Thr Ile Ile Val Gln Leu
                    245                 250                 255
Lys Glu Ser Val Glu Ile Asn Cys Thr Arg Pro Asn Asn Asn Thr Arg
                    260                 265                 270
Lys Ser Ile His Ile Gly Pro Gly Arg Ala Phe Tyr Thr Thr Gly Glu
                    275                 280                 285
Ile Ile Gly Asp Ile Arg Gln Ala His Cys Asn Ile Ser Arg Ala Lys
                    290                 295                 300
Trp Asn Asp Thr Leu Lys Gln Ile Val Ile Lys Leu Arg Glu Gln Phe
305                 310                 315                 320
Glu Asn Lys Thr Ile Val Phe Asn His Ser Ser Gly Gly Asp Pro Glu
                    325                 330                 335
Ile Val Met His Ser Phe Asn Cys Gly Gly Glu Phe Phe Tyr Cys Asn
                    340                 345                 350
Ser Thr Gln Leu Phe Asn Ser Thr Trp Asn Asn Asn Thr Glu Gly Ser
                    355                 360                 365
Asn Asn Thr Glu Gly Asn Thr Ile Thr Leu Pro Cys Arg Ile Lys Gln
                    370                 375                 380
Ile Ile Asn Met Trp Gln Glu Val Gly Lys Ala Met Tyr Ala Pro Pro
385                 390                 395                 400
Ile Arg Gly Gln Ile Arg Cys Ser Ser Asn Ile Thr Gly Leu Leu Leu
                    405                 410                 415
Thr Arg Asp Gly Gly Ile Asn Glu Asn Gly Thr Glu Ile Phe Arg Pro
                    420                 425                 430
Gly Gly Gly Asp Met Arg Asp Asn Trp Arg Ser Glu Leu Tyr Lys Tyr
                    435                 440                 445
Lys Val Val Lys Ile Glu Pro Leu Gly Val Ala Pro Thr Lys Cys Lys
                    450                 455                 460
Arg Arg Val Val Gln Arg Arg Arg Arg Ala Val Gly Ile Gly
465                 470                 475                 480
Ala Val Phe Leu Gly Phe Leu Gly Ala Ala Gly Ser Thr Met Gly Ala
                    485                 490                 495
```

```
Ala Ser Ile Thr Leu Thr Val Gln Ala Arg Gln Leu Leu Ser Gly Ile
            500                 505                 510

Val Gln Gln Gln Ser Asn Leu Leu Arg Ala Pro Glu Ala Gln Gln Arg
        515                 520                 525

Met Leu Lys Leu Thr Val Trp Gly Ile Lys Gln Leu Gln Ala Arg Val
    530                 535                 540

Leu Ala Val Glu Arg Tyr Leu Arg Asp Gln Gln Leu Leu Gly Ile Trp
545                 550                 555                 560

Gly Cys Ser Gly Lys Leu Ile Cys Cys Thr Ala Val Pro Trp Asn Ala
                565                 570                 575

Ser Trp Ser Asn Lys Ser Leu Asp Arg Ile Trp Asn Asn Met Thr Trp
            580                 585                 590

Met Glu Trp Glu Arg Glu Ile Asp Asn Tyr Thr Ser Glu Ile Tyr Thr
        595                 600                 605

Leu Ile Glu Glu Ser Gln Asn Gln Gln Glu Lys Asn Glu Gln Glu Leu
    610                 615                 620

Leu Glu Leu Asp Ala Ala Ala Trp Ser His Pro Gln Phe Glu Lys Gly
625                 630                 635                 640

Gly Gly Ser Gly Gly Gly Ser Gly Gly Ser Ala Trp Ser His Pro Gln
                645                 650                 655

Phe Glu Lys

<210> SEQ ID NO 11
<211> LENGTH: 665
<212> TYPE: PRT
<213> ORGANISM: Artificial Sequence
<220> FEATURE:
<223> OTHER INFORMATION: Artificial protein sequence of Strep-Tagged
      BG505 SOSIP(1-5).R6.664 gp140 comprising an engineered HIV-1 clade
      A BG505 gp140, a peptide linker, and a Strep-Tag.

<400> SEQUENCE: 11

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
```

```
            180             185             190
Phe Ala Ile Leu Lys Cys Lys Asp Lys Lys Phe Asn Gly Thr Gly Pro
            195             200             205
Cys Pro Ser Val Ser Thr Val Gln Cys Thr His Gly Ile Lys Pro Val
            210             215             220
Val Ser Thr Gln Leu Leu Leu Asn Gly Ser Leu Ala Glu Glu Glu Val
225             230             235             240
Met Ile Arg Ser Glu Asn Ile Thr Asn Asn Ala Lys Asn Ile Leu Val
            245             250             255
Gln Phe Asn Thr Pro Val Gln Ile Asn Cys Thr Arg Pro Asn Asn Asn
            260             265             270
Thr Arg Lys Ser Ile Arg Ile Gly Pro Gly Gln Ala Phe Tyr Ala Thr
            275             280             285
Gly Asp Ile Ile Gly Asp Ile Arg Gln Ala His Cys Asn Val Ser Lys
            290             295             300
Ala Thr Trp Asn Glu Thr Leu Gly Lys Val Val Lys Gln Leu Arg Lys
305             310             315             320
His Phe Gly Asn Asn Thr Ile Ile Arg Phe Ala Asn Ser Ser Gly Gly
            325             330             335
Asp Leu Glu Val Thr Thr His Ser Phe Asn Cys Gly Gly Glu Phe Phe
            340             345             350
Tyr Cys Asn Thr Ser Gly Leu Phe Asn Ser Thr Trp Ile Ser Asn Thr
            355             360             365
Ser Val Gln Gly Ser Asn Ser Thr Gly Ser Asn Asp Ser Ile Thr Leu
            370             375             380
Pro Cys Arg Ile Lys Gln Ile Ile Asn Met Trp Gln Arg Ile Gly Gln
385             390             395             400
Ala Met Tyr Ala Pro Pro Ile Gln Gly Val Ile Arg Cys Val Ser Asn
            405             410             415
Ile Thr Gly Leu Ile Leu Thr Arg Asp Gly Gly Ser Thr Asn Ser Thr
            420             425             430
Thr Glu Thr Phe Arg Pro Gly Gly Gly Asp Met Arg Asp Asn Trp Arg
            435             440             445
Ser Glu Leu Tyr Lys Tyr Lys Val Val Lys Ile Glu Pro Leu Gly Val
            450             455             460
Ala Pro Thr Arg Cys Lys Arg Arg Val Val Gly Arg Arg Arg Arg Arg
465             470             475             480
Arg Ala Val Gly Ile Gly Ala Val Phe Leu Gly Phe Leu Gly Ala Ala
            485             490             495
Gly Ser Thr Met Gly Ala Ala Ser Met Thr Leu Thr Val Gln Ala Arg
            500             505             510
Asn Leu Leu Ser Gly Ile Val Gln Gln Gln Ser Asn Leu Leu Arg Ala
            515             520             525
Pro Glu Ala Gln Gln His Leu Leu Lys Leu Thr Val Trp Gly Ile Lys
            530             535             540
Gln Leu Gln Ala Arg Val Leu Ala Val Glu Arg Tyr Leu Arg Asp Gln
545             550             555             560
Gln Leu Leu Gly Ile Trp Gly Cys Ser Gly Lys Leu Ile Cys Cys Thr
            565             570             575
Asn Val Pro Trp Asn Ser Ser Trp Ser Asn Arg Asn Leu Ser Glu Ile
            580             585             590
Trp Asp Asn Met Thr Trp Leu Gln Trp Asp Lys Glu Ile Ser Asn Tyr
            595             600             605
```

```
Thr Gln Ile Ile Tyr Gly Leu Leu Glu Glu Ser Gln Asn Gln Gln Glu
        610                 615                 620

Lys Asn Glu Gln Asp Leu Leu Ala Leu Asp Ala Ala Ala Trp Ser His
625                 630                 635                 640

Pro Gln Phe Glu Lys Gly Gly Ser Gly Gly Gly Ser Gly Gly Ser
            645                 650                 655

Ala Trp Ser His Pro Gln Phe Glu Lys
            660                 665

<210> SEQ ID NO 12
<211> LENGTH: 659
<212> TYPE: PRT
<213> ORGANISM: Artificial Sequence
<220> FEATURE:
<223> OTHER INFORMATION: Artificial protein sequence of Strep-Tagged
      SF162 SOSIP.R6.664 gp140 comprising an engineered HIV-1 clade B
      SF162 gp140, a peptide linker, and a Strep-Tag.

<400> SEQUENCE: 12

Val Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu His Cys Thr Asn Leu Lys Asn Ala Thr Asn Thr Lys Ser
            100                 105                 110

Ser Asn Trp Lys Glu Met Asp Arg Gly Glu Ile Lys Asn Cys Ser Phe
        115                 120                 125

Lys Val Thr Thr Ser Ile Arg Asn Lys Met Gln Lys Glu Tyr Ala Leu
    130                 135                 140

Phe Tyr Lys Leu Asp Val Val Pro Ile Asp Asn Asp Asn Thr Ser Tyr
145                 150                 155                 160

Lys Leu Ile Asn Cys Asn Thr Ser Val Ile Thr Gln Ala Cys Pro Lys
                165                 170                 175

Val Ser Phe Glu Pro Ile Pro Ile His Tyr Cys Ala Pro Ala Gly Phe
            180                 185                 190

Ala Ile Leu Lys Cys Asn Asp Lys Lys Phe Asn Gly Ser Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Gly Val Val
225                 230                 235                 240

Ile Arg Ser Glu Asn Phe Thr Asp Asn Ala Lys Thr Ile Ile Val Gln
                245                 250                 255

Leu Lys Glu Ser Val Glu Ile Asn Cys Thr Arg Pro Asn Asn Asn Thr
            260                 265                 270
```

-continued

```
Arg Lys Ser Ile Thr Ile Gly Pro Gly Arg Ala Phe Tyr Ala Thr Gly
        275                 280                 285
Asp Ile Ile Gly Asp Ile Arg Gln Ala His Cys Asn Ile Ser Gly Glu
290                 295                 300
Lys Trp Asn Asn Thr Leu Lys Gln Ile Val Thr Lys Leu Gln Ala Gln
305                 310                 315                 320
Phe Gly Asn Lys Thr Ile Val Phe Lys Gln Ser Ser Gly Gly Asp Pro
                325                 330                 335
Glu Ile Val Met His Ser Phe Asn Cys Gly Gly Glu Phe Phe Tyr Cys
                340                 345                 350
Asn Ser Thr Gln Leu Phe Asn Ser Thr Trp Asn Asn Thr Ile Gly Pro
                355                 360                 365
Asn Asn Thr Asn Gly Thr Ile Thr Leu Pro Cys Arg Ile Lys Gln Ile
            370                 375                 380
Ile Asn Arg Trp Gln Glu Val Gly Lys Ala Met Tyr Ala Pro Pro Ile
385                 390                 395                 400
Arg Gly Gln Ile Arg Cys Ser Ser Asn Ile Thr Gly Leu Leu Leu Thr
                405                 410                 415
Arg Asp Gly Gly Lys Glu Ile Ser Asn Thr Thr Glu Ile Phe Arg Pro
            420                 425                 430
Gly Gly Gly Asp Met Arg Asp Asn Trp Arg Ser Glu Leu Tyr Lys Tyr
            435                 440                 445
Lys Val Val Lys Ile Glu Pro Leu Gly Val Ala Pro Thr Lys Cys Lys
450                 455                 460
Arg Arg Val Val Gln Arg Arg Arg Arg Ala Val Thr Leu Gly
465                 470                 475                 480
Ala Met Phe Leu Gly Phe Leu Gly Ala Ala Gly Ser Thr Met Gly Ala
                485                 490                 495
Arg Ser Leu Thr Leu Thr Val Gln Ala Arg Gln Leu Leu Ser Gly Ile
                500                 505                 510
Val Gln Gln Gln Asn Asn Leu Leu Arg Ala Pro Glu Ala Gln Gln His
            515                 520                 525
Leu Leu Gln Leu Thr Val Trp Gly Ile Lys Gln Leu Gln Ala Arg Val
            530                 535                 540
Leu Ala Val Glu Arg Tyr Leu Lys Asp Gln Gln Leu Leu Gly Ile Trp
545                 550                 555                 560
Gly Cys Ser Gly Lys Leu Ile Cys Cys Thr Ala Val Pro Trp Asn Ala
                565                 570                 575
Ser Trp Ser Asn Lys Ser Leu Asp Gln Ile Trp Asn Asn Met Thr Trp
                580                 585                 590
Met Glu Trp Glu Arg Glu Ile Asp Asn Tyr Thr Asn Leu Ile Tyr Thr
                595                 600                 605
Leu Ile Glu Glu Ser Gln Asn Gln Gln Glu Lys Asn Glu Gln Glu Leu
610                 615                 620
Leu Glu Leu Asp Ala Ala Ala Trp Ser His Pro Gln Phe Glu Lys Gly
625                 630                 635                 640
Gly Gly Ser Gly Gly Gly Ser Gly Gly Ser Ala Trp Ser His Pro Gln
                645                 650                 655
Phe Glu Lys

<210> SEQ ID NO 13
<211> LENGTH: 6
<212> TYPE: PRT
```

```
<213> ORGANISM: Artificial Sequence
<220> FEATURE:
<223> OTHER INFORMATION: Artificial enhanced furin cleavage site protein
      sequence

<400> SEQUENCE: 13

Arg Arg Arg Arg Arg Arg
1               5
```

APPROACH TO PRODUCE HIV-1 GP140 ENVELOPE PROTEIN TRIMERS

CROSS-REFERENCE TO RELATED APPLICATIONS

This application claims benefit of priority to U.S. Provisional Patent Application No. 62/133,578, entitled "A NEW APPROACH TO PRODUCE HIV-1 GP140 ENVELOPE PROTEIN TRIMERS," filed Mar. 16, 2015; U.S. Provisional Patent Application No. 62/166,271, entitled "A NEW APPROACH TO PRODUCE HIV-1 ENVELOPE TRIMERS: BOTH CLEAVAGE AND PROPER GLYCOSYLATION ARE ESSENTIAL TO GENERATE AUTHENTIC TRIMERS," filed May 26, 2015. The entire contents and disclosures of these provisional patent applications are incorporated herein by reference.

This application makes reference to U.S. Provisional Patent Application No. 61/731,147, entitled "DESIGNING A SOLUBLE FULL-LENGTH HIV-1 GP41 TRIMER," filed Nov. 29, 2012 and U.S. patent application Ser. No. 14/091,401, entitled "DESIGNING A SOLUBLE FULL-LENGTH HIV-1 GP41 TRIMER," filed Nov. 27, 2013. The entire disclosure and contents of these patent applications are incorporated herein by reference.

STATEMENT OF GOVERNMENT INTEREST

This invention is made with government support under NIH grant AI102725 awarded by National Institute of Allergy and Infectious Diseases (NIAID) to Venigalla B. Rao. The U.S. Government has certain rights in this invention.

BACKGROUND

Field of the Invention

The present invention relates to HIV-1 envelope protein gp140 and HIV-1 envelope trimers, as well as an HIV vaccine.

Related Art

The trimeric envelope glycoprotein spike of HIV-1 mediates virus entry into human cells. The exposed part of the trimer, gp140, consists of two noncovalently associated subunits, gp120 and gp41 ectodomain. The surface of an HIV-1 virus is covered with 20-50 trimeric envelope spikes that are embedded in the viral envelope. The spike makes the first contact with the human T cell during sexual transmission of the virus. This interaction triggers a series of events leading to fusion of viral and host membranes and delivery of the virus nucleocapsid core into the host cell. This results in the establishment of HIV infection in the human host. A vaccine containing recombinantly produced viral trimers that mimics native spike might elicit trimer-specific antibodies, which by binding to the virus can disable envelope protein (Env) function and block the transmission of HIV into humans. Therefore, development of a recombinant trimer immunogen as a vaccine has been one of the top priorities in the hunt for an effective HIV vaccine. However, preparation of authentic HIV-1 trimers has been challenging. The procedures developed so far have not produced authentic trimers, which appear as three-blade propeller shaped particles when visualized by an electron microscope.

SUMMARY

According to a first broad aspect, the present invention provides a method comprising: attaching a first nucleic acid sequence encoding a tag through a second nucleic acid sequence encoding a peptide linker at 3'end of a third nucleic acid sequence encoding a recombinant HIV-1 gp140 to construct a recombinant DNA encoding a recombinant protein, wherein the recombinant protein comprises the recombinant HIV-1 gp140 fused to the tag through the peptide linker at C-terminus of the recombinant HIV-1 gp140, and wherein the peptide linker is sufficiently long so that the tag is accessible for binding by a binding molecule bound on a solid matrix.

According to a second broad aspect, the present invention provides a method comprising: inserting a first nucleic acid sequence encoding a recombinant HIV-1 gp140 into a first vector to construct a second vector for expression of a recombinant protein comprising the recombinant HIV-1 gp140 fused to a tag through a peptide linker, wherein the first vector comprises an expression cassette comprising: a regulatory region operably linked to a second nucleic acid sequence encoding a secretion signal peptide, a third nucleic acid sequence encoding the peptide linker and the tag to be fused to C-terminus of the recombinant gp140, and an insertion region comprising two or more restriction sites, wherein the second nucleic acid sequence is adjacent to 5' end of the insertion region and the third nucleic acid sequence is adjacent to 3' end of the insertion region, wherein the first nucleic acid sequence is inserted into the first vector at the two or more restriction sites, wherein the peptide linker is sufficiently long so that the tag fused to the recombinant HIV-1 gp140 is accessible for binding by a binding molecule bound on a solid matrix, and wherein the regulatory region regulates expression of the recombinant protein in a cell carrying the second vector.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 35 is an image of negative-stain EM of the peak SEC fraction of purification of uncleaved trimers expressed in 293F cells according to one embodiment of the present invention.

FIG. 36 is an image of negative-stain EM of the peak SEC fraction purification of uncleaved trimers expressed in 293F cells according to one embodiment of the present invention.

FIG. 37 is an image of negative-stain EM of the peak SEC fraction purification of uncleaved trimers expressed in 293F cells according to one embodiment of the present invention.

FIG. 40 is an image of negative-stain EM of the peak SEC fraction of purification of uncleaved trimers expressed in GnTI⁻ cells according to one embodiment of the present invention.

FIG. 41 is an image of negative-stain EM of the peak SEC fraction purification of uncleaved trimers expressed in GnTI⁻ cells according to one embodiment of the present invention.

FIG. 42 is an image of negative-stain EM of the peak SEC fraction purification of uncleaved trimers expressed in GnTI⁻ cells according to one embodiment of the present invention.

DETAILED DESCRIPTION OF THE PREFERRED EMBODIMENTS

Definitions

Figure 1:
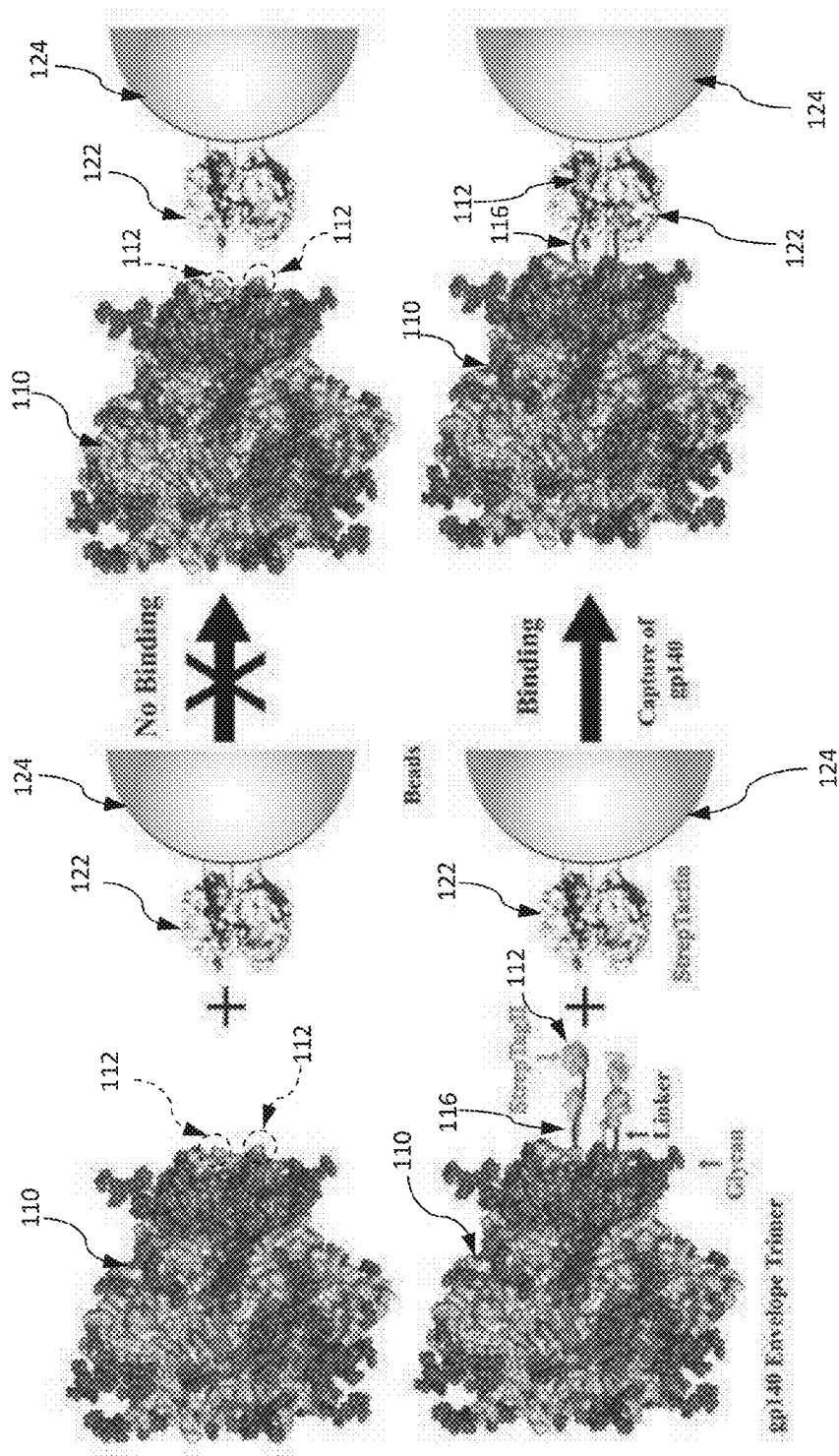
FIG. 1 is a schematic diagram showing a recombinant trimer of envelope protein gp140 fused to tags through long linkers according to one embodiment of the present invention in comparison with a recombinant trimer of envelope protein gp140 fused to tags without long linkers.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, the term "comprising", the term "having", and the term "including" are intended to be open-ended and mean that there may be additional elements other than the listed elements.

For purposes of the present invention, the term "access" refers to approaching near and being able to contact or interact with a molecule. For example, when a binding molecule accesses a target peptide, the binding molecule approaches near the target peptide and then binds to the target peptide. A binding molecule that is accessible to a target peptide is not blocked or sterically hindered by the 3-dimensional (3-D) structure of a protein or a protein complex comprising the target peptide. For example, if a peptide tag fused at an end of a protein or a protein complex is accessible for binding by a binding molecule bound on a solid matrix, the access and binding of the binding molecule bound on a solid matrix to the peptide tag is not sterically hindered by the 3-D structure of the protein or the protein complex.

For purposes of the present invention, the term "accessible for binding" refers to a binding site of a target molecule or target complex that is not blocked or sterically hindered by the 3-D structure of the target molecule or target complex with respect to a binding molecule binding to the binding site. For example, in one embodiment of the present invention where the binding site is a tag fused to a gp140 protein, a long linker is used to separate the tag from the gp140 protein to make the tag available to be bound by a binding molecule, thereby preventing structures of the gp140 protein from sterically hindering or blocking access of the binding molecule to the tag.

For purposes of the present invention, the term "affinity chromatography" refers to a separation technique based upon molecular conformation, which frequently utilizes application specific resins. These resins have ligands attached to their surfaces which are specific for the compounds to be separated. Most frequently, these ligands function in a fashion similar to that of antibody-antigen interactions. For example, many membrane proteins are glycoproteins and can be purified by lectin affinity chromatography. Detergent-solubilized proteins can be allowed to bind to a chromatography resin that has been modified to have a covalently attached lectin. Proteins that do not bind to the lectin are washed away and then specifically bound glycoproteins can be eluted by adding a high concentration of a sugar that competes with the bound glycoproteins at the lectin binding site. Some lectins have high affinity binding to oligosaccharides of glycoproteins that is hard to compete with sugars, and bound glycoproteins need to be released by denaturing the lectin.

For purposes of the present invention, the term "antibody" refers to a protein produced by plasma cells that are used by an immune system to identify and neutralize foreign objects, for example, bacteria and viruses. An "antibody" is also known as an "immunoglobulin." Each antibody recognizes a specific part of a specific foreign object, called an antigen, and binds the specific antigen. Antibodies can cause agglutination and precipitation of antibody-antigen products, prime for phagocytosis by macrophages and other cells, block viral receptors, and stimulate other immune responses, such as the complement pathway.

For purposes of the present invention, the term "attach," when is used in protein or polypeptide, refers to join, fuse, link, or connect two amino acid sequences together. For example, an amino acid tag may be attached to a polypeptide of interest such as a gp140 at C-terminus or N-terminus. Usually, a tag is attached or fused to a polypeptide through a linker, wherein the linker locates between the polypeptide and the tag.

For purposes of the present invention, the term "base of a trimer" and the term "base of a gp140 structure" are used interchangeably to refer to the portion of a gp140 subunit within the trimer or the gp140 structure not including other molecules bound, attached or complexed with one of the gp140 subunits of the trimer. For example, linkers, tags, etc. are not part of the base of a trimer or the base of a gp140 structure.

For purposes of the present invention, the term "bind," the term "binding" or the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "binding molecule" refers to a molecule having a specific interaction with a target complex such as a DNA, a protein, a polypeptide, or a polypeptide oligomer, etc. A specific interaction between the binding molecule and the target complex may be a highly specific interaction such as an interaction between antigen and antibody, or receptor and ligand. A binding molecule may be bound to a solid matrix such as agarose beads and then be used in protein affinity purification to capture a target complex from a mixture containing the target complex. A binding molecule bound to a solid matrix may be a Ni-NTA bead, a STREP-TACTIN® bead, etc. For example, in affinity purification of a protein or an antigen from a mixture, an antibody against a target protein or a target antigen may be used as a binding molecule and be bound to a bead to capture the protein or the antigen from the mixture. In some examples, a binding molecule may be a small molecule specifically binds to a tag fused on a recombinant protein.

For purposes of the present invention, the term "clade" refers to related human immunodeficiency viruses (HIVs) classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, a composition of the invention (e.g., any one of the vaccines of the first or fourth aspects, the compositions of the third aspect, the nucleic acid molecules of the fifth aspect, and/or the vectors of the sixth aspect) as described herein will recognize and raise an immune response (e.g., neutralizing anti-HIV antisera) against two, three, four, five, six, seven, eight, nine, ten or more clades and/or two or more groups of HIV.

For purposes of the present invention, the term "cleavage" refers to breaking of a chemical bond in a polypeptide molecule to separate or divide a polypeptide molecule into two or more portions such as two small peptides.

For purposes of the present invention, the term "correspond" and the term "corresponding" refer to that a protein sequence refer interchangeably to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc.

For purposes of the present invention, the term "constitutively express" refers to the consistent synthesis of a protein. "Constitutively express" is contrary to "inducible expression" which depends on promoters that respond to the induction conditions.

For purposes of the present invention, the term "crosslink" refers to a bond that links one polypeptide to another. Proteins naturally present in the body can contain crosslinks generated by enzyme-catalyzed or spontaneous reactions. Such crosslinks are important in generating mechanically stable structures such as hair, skin and cartilage. Disulfide bond formation is one of the most common crosslinks, but isopeptide bond formation is also common. Proteins can also be cross-linked artificially using small-molecule crosslinkers. Compromised collagen in the cornea, a condition known as keratoconus, can be treated with clinical crosslinking.

For purposes of the present invention, the term "culture medium," the term "culture supernatant," and the term "cell culture supernatant" refer to the media/fluid in which cells are suspended/cultured during growth. Culture supernatant is usually the clear upper liquid part of a mixture including cells and media after being centrifuged. Culture supernatant may also be the liquid lying above a layer of precipitated cells.

For purposes of the present invention, the term "domain" and the term "protein domain" refer to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purposes of the present invention, the term "ectodomain" refers to a domain of a membrane protein that extends into the extracellular space (e.g., a space outside a cell). Ectodomains are usually the parts of proteins that initiate contact with surfaces, which leads to signal transduction. For example, the ectodomain of an HIV-1 envelope glycoprotein (Env) is a heterodimer with mass of approximately 140 kDa, composed of the entire gp120 component, and approximately 20 kDa of gp41, which are displayed on the surface of the viral membrane.

For purposes of the present invention, the term "engineered" refers to being made by biological engineering.

For purposes of the present invention, the term "Env spike" refers to a structure of a complex existing on the envelope of an HIV viral particle. An HIV Env spike is a trimer formed by envelope protein Env gp140.

For purposes of the present invention, the term "envelope glycoprotein" and the term "Env" refer to, but are not limited to, the glycoprotein that is expressed on the surface of the envelope of HIV virions and the surface of the plasma membrane of HIV infected cells. For example, a native env gene encodes gp160, which is proteolytically cleaved into the gp120 and gp41 Envelope (Env) proteins. Gp120 binds to the CD4 receptor on a target cell that has such a receptor, such as, e.g., a T-helper cell. A native Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

For purposes of the present invention, the term "epitope" refers to a molecular region on the surface of an antigen capable of eliciting an immune response and combining with the specific antibody produced by such a response. It is also called "antigenic determinant." T cell epitopes are presented on the surface of an antigen-presenting cell, where they are bound to MHC molecules.

For purposes of the present invention, the term "expression" and the term "gene expression" refer to a process by which information from a gene or a fragment of DNA is used in the synthesis of a functional gene product. A gene which encodes a protein will, when expressed, be transcribed and translated to produce that protein.

For purposes of the present invention, the term "expression cassette" refers to a part of a vector DNA used for cloning and transformation. In each successful transformation, the expression cassette directs the cell's machinery to make RNA and protein. Some expression cassettes are designed for modular cloning of protein-encoding sequences so that the same cassette can easily be altered to make different proteins. Expression cassettes may also refer to a recombinantly produced nucleic acid molecule that is capable of expressing a genetic sequence in a cell. An expression cassette typically includes a regulatory region such as a promoter, (allowing transcription initiation), and a sequence encoding one or more proteins or RNAs. Optionally, the expression cassette may include transcriptional enhancers, non-coding sequences, splicing signals, transcription termination signals, and polyadenylation signals. The sequences controlling the expression of the gene, i.e. its transcription and the translation of the transcription product, are commonly referred to as regulatory unit. Most parts of the regulatory unit are located upstream of coding sequence of the heterologous gene and are operably linked thereto. The expression cassette may also contain a downstream 3' untranslated region comprising a polyadenylation site. The regulatory unit of the invention is either directly linked to the gene to be expressed, i.e. transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the present invention can be used for the construction of an expression vector, in particular a mammalian expression vector.

For purposes of the present invention, the term "expression vector," otherwise known as an expression construct, refers to a plasmid or virus designed for protein expression in cells. The vector is used to introduce a specific gene into a target cell, and can commandeer the cell's mechanism for protein synthesis to produce the protein encoded by the gene. The plasmid is engineered to contain regulatory sequences that act as enhancer and promoter regions and lead to efficient transcription of the gene carried on the expression vector. The goal of a well-designed expression vector is the production of significant amount of stable messenger RNA, and therefore proteins.

For purposes of the present invention, the term "foldon sequence" refers to a sequence derived from the native T4 phage fibritin. The foldon sequence has a sequence of YIPEAPRDGQAYVRKDG EWVLLSTFL (SEQ ID NO: 1). When incorporated at the C-terminal of a protein molecule, the foldon sequence stabilizes the triple helix formed in the protein.

For purposes of the present invention, the term "fragment" of a molecule such as a protein or a nucleic acid refers to a portion of an amino acid sequence of the protein or a portion of a nucleotide sequence of the nucleic acid.

For purposes of the present invention, the term "furin" refers to a protein encoded by the FURIN gene. Some proteins are inactive when they are first synthesized, and must have sections deleted in order to become active. Furin deletes these sections and activates the proteins. Furin is one of the proteases responsible for the proteolytic cleavage of HIV envelope polyprotein precursor gp160 to gp120 and gp41 prior to viral assembly.

For purposes of the present invention, the term "furin cleavage proficient (CP)" refers to offering proficiency for cleavage by furin. A protein with furin cleavage proficient site is likely to be cleaved by furin.

For purposes of the present invention, the term "furin cleavage resistant (CR)" refers to offering resistance to be cleaved by furin. A protein with furin cleavage resistant site is unlikely to be cleaved by furin.

For purposes of the present invention, the term "fuse" refers to join together physically, or to make things join together and become a single thing.

For purposes of the present invention, the term "fusion polypeptide" or the term "fusion protein" refers to a protein having at least two heterologous polypeptides covalently linked, either directly or via an amino acid linker. The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. These terms may also refer to a protein developed from a fusion gene that is created through a joining of two or more genes originally coding for separate proteins. Translation of this fusion gene results in a single or multiple polypeptides with functional properties derived from each of the original proteins. In present invention, "fusion protein" and "recombinant protein" are interchangeable. Fusion proteins of the disclosure may also comprise additional copies of a component antigen or immunogenic fragment thereof.

For purposes of the present invention, the term "fusion polypeptide" or the term "fusion protein" refers to a protein having at least two heterologous polypeptides covalently linked, either directly or via an amino acid linker. The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. These terms may also refer to a protein developed from a fusion gene that is created through a joining of two or more genes originally coding for separate proteins. Translation of this fusion gene results in a single or multiple polypeptides with functional properties derived from each of the original proteins. In present invention, "fusion protein" and "recombinant protein" are interchangeable. Fusion proteins of the disclosure may also comprise additional copies of a component antigen or immunogenic fragment thereof.

For purposes of the present invention, the term "gel electrophoresis" refers to a method for separation and analysis of macromolecules (DNA, RNA and proteins) and their fragments, based on their size and charge. Gel electrophoresis conditions include denaturing condition and native condition (non-denaturing condition). Under denaturing condition, molecules such as proteins are denatured in a solution containing a detergent (SDS). In these conditions, for example, proteins are unfolded and coated with negatively charged detergent molecules. Proteins in SDS-PAGE are then separated on the sole basis of their size. The protein migrates as bands based on size. Each band can be detected using stains such as Coomassie blue dye or silver stain. Unlike denaturing methods, native gel electrophoresis does not use a charged denaturing agent. Under native condition, molecules such as proteins maintain their natural structures. The molecules being separated therefore differ not only in molecular mass and intrinsic charge, but also the cross-sectional area, and thus experience different electrophoretic forces dependent on the shape of the overall structure. For proteins, since they remain in the native state they may be visualized not only by general protein staining reagents but also by specific enzyme-linked staining.

For purposes of the present invention, the term "gene" refers to a nucleic acid (e.g., DNA or RNA) sequence that comprises coding sequences necessary for the production of an RNA or a polypeptide or its precursor. The term "portion," when used in reference to a gene, refers to fragments of that gene. The fragments may range in size from a few nucleotides to the entire gene sequence minus one nucleotide.

For purposes of the present invention, the term "glycosylation" refers to attachment of monosaccharides and oligosaccharides to a protein backbone via a glycosidic linkage. Glycosylation is a post-translation modification. The term "hyper glycosylated" refers to more extensive glycosylation when compared to the "normal" glycosylation observed in the native-like cleaved trimers. These differences can be observed as differences in the mobility upon polyacrylamide gel electrophoresis. In embodiments of the present invention, the term "fully glycosylated" refers to glycosylations that occur in the HEK293 cell, a human embryonic kidney cell line used for production of gp140. "Partial glycosylation" occurs in the GnTI⁻ cell line. The GnTI⁻ cell line lacks the N-acetylglucosamine transferase 1 enzyme, hence it cannot introduce complex glycosylations.

For purposes of the present invention, the term "gp120" and the term "envelope glycoprotein gp120" refers to a glycoprotein exposed on the surface of the HIV envelope. The gp120 in its name comes from its molecular weight of 120 kDa. Gp120 is essential for virus entry into cells as it plays a vital role in attachment to specific cell surface receptors. Gp120 is coded by the HIV env gene, which is around 2.5 kb long and codes for around 850 amino acids. The primary env product is the protein gp160, which gets cleaved to gp120 (~480 amino acids) and gp41 (~345 amino acids) in the endoplasmatic reticulum by the cellular protease furin. The crystal structure of core gp120 shows an organization with an outer domain, an inner domain with respect to its termini and a bridging sheet. Gp120 is anchored to the viral membrane, or envelope, via non-covalent bonds with the transmembrane glycoprotein, gp41. Three gp120s and gp41s combine in a trimer of heterodimers to form the envelope spike, which mediates attachment to and entry into the host cell.

For purposes of the present invention, the term "human immunodeficiency virus" and the term "HIV" refer to a virus of the genus Lentivirinae, part of the family of Retroviridae, and includes, but is not limited to, HIV type 1 (HIV-1) and HIV type 2 (HIV-2), two species of HIV that infect humans. The HIV-I virus may represent any of the known major subtypes or clades (e.g., Classes A, B, C, D, E, F, G, J, and H) or outlying subtype (Group 0). Also encompassed are other HIV-I subtypes or clades that may be isolated. An "HIV isolate" refers to a type of HIV virus that has been separated and identified from other species of HIV.

For purposes of the present invention, the term "HIV-1 gp140," the term "gp140," and the term "gp140 envelope protein" refer to a protein having two disulfide-linked polypeptide chains, the first chain comprising the amino acid sequence of the HIV gp120 glycoprotein and the second chain comprising the amino acid sequence of the water-soluble portion of HIV gp41 glycoprotein ("gp41 portion"). In embodiments of the present invention, HIV gp140 proteins include, but are not limited to, proteins wherein the gp41 portion comprises a point mutation such as I559P. I559P refers to a mutation introduced to change Isoleucine at position 559 to Proline.

For purposes of the present invention, the term "HIV-1 gp41," the term "gp41," the term "glycoprotein 41," and the term "gp41 subunit" refers to a subunit of the envelope protein complex of retroviruses, including Human immunodeficiency virus (HIV). These terms include, but are not limited to: 1) an entire gp41 polypeptide including the transmembrane and cytoplasmic domains; 2) a "gp41 ectodomain" (gp41 ECTo); (3) a gp41 modified by deletion or insertion of one or more glycosylation sites; (4) a gp41 modified so as to eliminate or mask the well-known immunodominant epitope; (5) a gp41 fusion protein; and (6) a gp41 labeled with an affinity ligand or other detectable marker. As used herein, "ectodomain" means the extracellular region of a transmembrane protein exclusive of the transmembrane spanning and cytoplasmic regions.

For purposes of the present invention, the term "host cell" and the term "host" refer to 1) a cell that harbors foreign molecules, viruses, etc.; 2) a cell that has been introduced with DNA or RNA, such as a bacterial cell acting as a host cell for the DNA isolated from a bacteriophage. For example, a host cell may be a living cell in which a virus such as HIV-1 reproduces.

For purposes of the present invention, the term "incorporate" refers to insert a fragment of a first nucleic acid into a fragment of a second nucleic acid.

For purposes of the present invention, the term "immunogen" and the term "immunogenic composition" refer to a substance or material (including antigens) that is able to induce an immune response alone or in conjunction with an adjuvant. Both natural and synthetic substances may be immunogens.

For purposes of the present invention, the term "immune response" refers to any response to an antigen or antigenic determinant by the immune system of a subject (e.g., a human). Exemplary immune responses include humoral immune responses (e.g., production of antigen-specific antibodies, e.g., neutralizing antibodies (NAbs)) and cell-mediated immune responses (e.g., lymphocyte proliferation).

For purposes of the present invention, the term "junction," the term "junction fragment," the term "junction sequence," and the term "junction peptide" are interchangeable and refer to a region or a fragment or a portion of peptide between two subunits or sections within a polypeptide. The two subunits or sections meet or join via the junction fragment.

For purposes of the present invention, the term "ligand" refers to an organic molecule that donates the necessary electrons to form coordinate covalent bonds with metallic ions. Ligand also refers to an ion, a molecule, or a molecular group that binds to another chemical entity to for a larger complex.

For purposes of the present invention, the term "linked" refers to a covalent linkage between two polypeptides in a fusion protein. The polypeptides are typically joined via a peptide bond, either directly to each other or via one or more additional amino acids.

For purposes of the present invention, the term "linker" and the term "peptide linker" are interchangeable and refer to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy. A linker may be from about 3 to about 15 amino acids long. In some embodiments of the present invention, a linker may be about 5 to about 10 amino acids long, however, longer linker may be used in embodiments of the present invention.

For purposes of the present invention, a "long linker" refers to a linker that is sufficiently long that a tag that is fused to a gp140 protein is accessible for binding by a binding molecule. In some embodiments of the present invention, a long linker may be more than 3 amino acids in length. In some embodiments, a long linker may be 20 or more amino acids in length. In some embodiments of the present invention, a long linker may be 23 or more amino acids in length. In some embodiments, a long linker may be 27 or more amino acids in length.

For purposes of the present invention, the term "mimic" refers to have a similar structure. For example, according to embodiment of the present, when a trimer formed by three copies of protein molecule of a recombinant HIV gp140 protein mimics native HIV Envelope protein (Env) gp140 trimer, it means that the trimer formed by three copies of protein molecule of a recombinant HIV gp140 protein resemble the trimeric structure formed by native HIV gp140 at natural condition. A trimer formed by recombinant HIV gp140 protein that mimics native HIVgp140 trimer structure (the native Env spike) may be able to elicit neutralizing antibody responses in immunized animals.

For purposes of the present invention, the term "modified" and the term "mutant" when made in reference to a gene or to a gene product refer, respectively, to a gene or to a gene product which displays modifications in sequence and/or functional properties (i.e., altered characteristics) when compared to the wild-type gene or gene product.

For purposes of the present invention, the term "monomer" refers to a molecule that may bind chemically to other molecules to form a polymer. The term "monomeric protein" may also be used to describe one of the proteins making up a multiprotein complex.

For purposes of the present invention, the term "mutation" refers to a change in the polypeptide sequence of a protein or in the nucleic acid sequence.

For purposes of the present invention, the term "native-like" refers to resemble a naturally existing product or a structure of the native product.

For purposes of the present invention, the term "neutralizing antibody (Nab)" refers to an antibody which either is purified from, or is present in, serum and which recognizes a specific antigen (e.g., HIV Env glycoprotein, such as a gp140 polypeptide or a gp120 polypeptide) and inhibits the effect(s) of the antigen in the host (e.g., a human). As used herein, the antibody can be a single antibody or a plurality of antibodies.

For purposes of the present invention, the term "Ni-based resin" and the term "nickel based resin" refer to a nickel-charged resin that can be used in purification of recombinant proteins carrying a His-tag. Ni-based resins include Ni-NTA agarose or beads, and other Ni-IDA resins. Histidine residues in the His-tag bind to the vacant positions in the coordination sphere of the immobilized nickel ions with high specificity and affinity. For example, cleared cell lysates containing a His-tagged recombinant protein may be loaded onto a Ni-NTA agarose. His-tagged proteins are bound, and other proteins pass through the matrix. After washing, His-tagged proteins are eluted in buffer under native or denaturing conditions.

For purposes of the present invention, the term "nucleic acid" and the term "polynucleotide," as used interchangeably herein, refer to polymers of nucleotides of any length, and include DNA and RNA. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of reverse transcriptase. A polynucleotide may comprise modified nucleotides, such as methylated nucleotides and their analogs.

For purposes of the present invention, the term "oligomer," when used in the context of a protein and/or polypeptide, refers to, but is not limited to, a protein or polypeptide having at least two subunits. Oligomers include, but are not limited to, dimers, trimers, tetramers, pentamers, hexamers, heptamers, octamers, nonamers, decamers and the like. An oligomer can be a macromolecular complex formed by non-covalent bonding of few macromolecules like proteins or nucleic acids. In this sense, a homo-oligomer would be formed by few identical molecules and by contrast, a hetero-oligomer would be made of three different macromolecules.

For purposes of the present invention, the term "operably linked," the term "operably associated," and the term "functionally linked" are used interchangeably and refer to a functional relationship between two or more DNA segment. Particularly, "operably linked" may refer to place a first nucleic acid sequence in a functional relationship with the second nucleic acid sequence. For example, a promoter/enhancer sequence, including any combination of cis-acting transcriptional control elements is operably associated to a coding sequence if the promoter/enhancer sequence affects the transcription or expression of the coding sequence in an appropriate host cell or other expression system. Promoter regulatory sequences that are operably linked to the transcribed gene sequence are physically contiguous to the transcribed sequence.

For purposes of the present invention, the term "optimize" refers to determining conditions for the maximal production of gp140 protein in the culture medium. Optimization of gp140 protein may involve modification of the amino acid sequence of a gp140 to determine conditions for the maximal production of modified gp140 protein in the culture medium.

For purposes of the present invention, the term "optimized polypeptide" refers to an polypeptide that is not a naturally-occurring peptide, polypeptide, or protein, such as a non-naturally occurring viral polypeptide (e.g., a gp140 polypeptide of the invention). Optimized viral polypeptide sequences are initially generated by modifying the amino acid sequence of one or more naturally-occurring viral gene products (e.g., peptides, polypeptides, and proteins, e.g., a viral Env polypeptide, e.g., a viral Env1, Env2, and/or Env3 polypeptide). Thus, the optimized viral polypeptide may correspond to a "parent" viral gene sequence; alternatively, the optimized viral polypeptide may not correspond to a specific "parent" viral gene sequence but may correspond to analogous sequences from various strains or quasi-species of a virus. Modifications to the viral gene sequence that can be included in an optimized viral polypeptide include amino acid additions, substitutions, and deletions.

For purposes of the present invention, the term "polymer" refers to a compound or a mixture of compounds comprising many repeating subunits, known as monomers.

For purposes of the present invention, the term "polypeptide" and the term "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer.

For purposes of the present invention, the term "promoter" refers to a regulatory DNA sequence generally located upstream of a gene that mediates the initiation of transcription by directing RNA polymerase to bind to DNA and initiating RNA synthesis. A promoter may be a constitutive promoter or an inducible promoter. A constitutive promoter (e.g. a viral promoter) is always active. For example, human cytomegalovirus (CMV) promoter drives constitutive protein expression in organisms, such as human cells. An inducible promoter is not always active. Some inducible promoters are activated by physical means such as the heat shock promoter.

For purposes of the present invention, the term "protomer" refers to a structural unit of an oligomeric protein. Protomer describes the fact that in oligomeric proteins some subunits are closer together structurally, and work closer together functionally, than others. For example, an HIV Env trimer encompasses three molecules of heterodimer that is formed by a gp120 subunit and a gp41 subunit, each dimer encompassing a gp120 and a gp41 may be called a protomer.

For purposes of the present invention, the term "protein purification" refers to a series of processes intended to isolate one or a few proteins from a complex mixture, such as cell culture media, cells, tissues or whole organisms, etc. Usually a protein purification protocol contains one or more chromatographic steps. The basic procedure in chromatography is to flow the solution containing the protein through a column packed with various materials. Different proteins interact differently with the column material, and can thus be separated by the time required to pass the column, or the conditions required to elute the protein from the column. Many purification strategies exist. For example, a protein can be attached with an antigen peptide tag by engineering and be purified using an antibody against the antigen peptide tag. Usually, during purification, the protein with an antigen peptide tag can be added on a column loaded with resin that is coated with an antibody or by incubating with a loose resin that is coated with an immobilizing antibody. This particular procedure is known as immunoprecipitation. Immunoprecipitation is quite capable of generating an extremely specific interaction which usually results in binding only the desired protein. The purified tagged proteins can then easily be separated from the other proteins in solution and later eluted back into clean solution.

For purposes of the present invention, the term "purified" refers to the component in a relatively pure state, e.g. at least about 90% pure, or at least about 95% pure, or at least about 98% pure.

For purposes of the present invention, the term "recombinant vaccine" refers to a vaccine made by genetic engineering, the process and method of manipulating the genetic material of an organism. Usually, a recombinant vaccine encompasses one or more protein antigens that have either been produced and purified in a heterologous expression system (e.g., bacteria or yeast) or purified from large amounts of the pathogenic organism. The vaccinated person produces antibodies to the one or more protein antigens, thus protecting him/her from disease.

For purposes of the present invention, the term "recombinant" refers to a genetic material formed by a genetic recombination process. A "recombinant protein is made through genetic engineering. A recombinant protein is coded by a DNA sequence created artificially. A recombinant protein is a protein that is coded by a recombinant nucleic acid sequence. A recombinant nucleic acid sequence has a sequence from two or more sources incorporated into a single molecule.

For purposes of the present invention, the term "regulatory region" refers to a segment of a nucleic acid molecule which is capable of increasing or decreasing the expression of specific genes within an organism. A regulatory sequence may include enhancer/silencer, operator, and promoter regions which regulate the transcription of the gene into an mRNA.

For purposes of the present invention, the term "secretion" and the term "secretion of a protein" or refers to transport a protein synthesized by a cell from intracellular of the cell into the extracellular space.

For purposes of the present invention, the term "secretion signal peptide," the term "secretion peptide," the term "signal peptide," and the term "secretion signal sequence" are used interchangeably and refer to a short (about 5-30 amino acids long) peptide present at the amino-terminus (N-terminus) of secreted and membrane-bound proteins. A secretion signal peptide present at a majority of newly synthesized proteins that are destined towards the secretory pathway. A signal peptide directs a newly synthesized protein to the secretory pathway. The cleavage of the signal peptide from a mature protein may occur during or after completion of translocation to generate a free signal peptide and a mature protein. The free signal peptides are then digested by specific proteases. The signal peptide consists of three regions: an amino-terminal polar region (N region), where frequently positive charged amino acid residues are observed, a central hydrophobic region (H region) of 7-8 amino acid residues and a carboxy-terminal region (C region) that includes the cleavage site.

For purposes of the present invention, the term "solid matrix" refers to a solid phase such as a gel matrix, often of agarose, used in affinity purification of a protein. For example, a ligand such as a nickel (Ni) can be coupled to an agarose to form a Ni-based agarose bead. During affinity purification process, molecules of interest such as a His-tagged target protein or its oligomer can be trapped or captured on a Ni-based agarose bead and be separated from a mixture containing the His-tagged target protein. The trapped molecules of interest can be then released from the Ni-based agarose in a process known as elution.

For purposes of the present invention, the term "steric hindrance" refers to the prevention or retardation of inter molecule interactions as a result of the spatial structure of a molecule. Steric hindrance occurs when the 3-dimensional (3-D) shape of a molecule in large size prevents ready access to the molecule in large size by a molecule in smaller size. For example, a peptide fragment such as a protein tag within a large protein molecule may be sterically hindered to bind to a binding molecule because the 3-D conformation or shape of the large protein molecule blocks the access of the binding molecule to the peptide fragment.

For purposes of the present invention, the term "stimulate," the term "immuno-stimulate" refers to induce the activation or increase the activity of any components in an immune system. For example, T cell activation requires at least two signals to become fully activated. The first occurs after engagement of the T cell antigen-specific receptor (TCR) by the antigen-major histocompatibility complex (MHC), and the second by subsequent engagement of co-stimulatory molecules. Once stimulated, the T cells will recognize the antigen or vaccine used during stimulation or activation of the T cells.

For purposes of the present invention, the term "STREP-TAG® II" refers to an eight-residue minimal peptide sequence (Trp-Ser-His-Pro-Gln-Phe-Glu-Lys) that exhibits intrinsic affinity toward streptavidin and can be fused to recombinant proteins in various fashions.

For purposes of the present invention, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purposes of the present invention, the term "tag," the term "peptide tag," and the term "protein tag" refer to, but are not limited to, a polypeptide sequence that can be added to another polypeptide sequence for a variety of purposes. In certain exemplary embodiments, a protein tag may be removed from a larger polypeptide sequence when it is no longer needed. Protein tags include, but are not limited to, affinity tags, epitope tags, etc. Affinity tags are appended to proteins so that they can be purified from their crude biological source using an affinity technique. For example, an His tag is a widely used protein tag. An His tag has a DNA sequence specifying a string of six to nine histidine residues and is frequently used in vectors for production of recombinant protein. The result is expression of a recombinant protein with an His tag such as a 6×His tag fused to N- or C-terminus of the recombinant protein. Expressed His-tagged proteins can be purified and detected easily because the string of histidine residues binds to several types of immobilized metal ions, including nickel, cobalt and copper, under specific buffer conditions. In addition, anti-His-tag antibodies are commercially available for use in assay methods involving His-tagged proteins. In either case, the tag provides a means of specifically purifying or detecting the recombinant protein without a protein-specific antibody or probe. Other affinity tags include, but are not limited to, chitin binding protein (CBP), maltose binding protein (MBP), glutathione-s-transferase (GST) and the like. Epitope tags are short peptide sequences which are chosen because high-affinity antibodies can be reliably produced in many different species. Epitope tags may be used in anti-body purification. In some situations, after purification, tags are commonly removed by approaches such as specific proteolysis, etc.

For purposes of the present invention, the term "tagged protein" refers to a recombinant protein that is fused with a tag.

For purposes of the present invention, the term "target" refers to a living organism or a biological molecule to which some other entity, such as a small molecule like a ligand or an antibody, is directed and/or binds.

For purposes of the present invention, the term "transfection" refers to a variety of art-recognized techniques for introducing foreign nucleic acid (e.g., DNA) into a host cell by calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), electroporation (e.g., in vivo electroporation), etc. Suitable methods for transfecting host cells can be found in Sambrook, et al., ("Molecular Cloning: A Laboratory Manual." 2nd, ed., Cold Spring harbor Laboratory, Cold Spring Harbor Laboratory Press, Cold Spring Harbor, N.Y., 1989), and other laboratory manuals.

For purposes of the present invention, the term "trimer" refers to "a protein trimer." A protein trimer is a macromolecular complex formed by three macromolecules like proteins. A homo-trimer would be formed by three identical molecules. A hetero-trimer is formed by three different macromolecules. For example, a native and functional HIV-1 envelope glycoprotein (Env) complex is present on the virus surface as a trimer, or trimeric HIV-1 envelope glycoproteins. The trimeric HIV-1 envelope glycoproteins (Env) that are displayed on human and simian immunodeficiency viruses (HIV and SIV, respectively) are heterodimers of the transmembrane glycoprotein (gp41) and a surface glycoprotein (gp120). The glycoproteins gp120 and gp41 are synthesized initially as a single gp160 polypeptide that is subsequently cleaved to generate the noncovalently associated gp120/gp41 complex.

For purposes of the present invention, the term "trimerization" refers to a process of polymerization resulting in a trimer.

For purposes of the present invention, the term "truncation" refers to elimination of the N- or C-terminal portion of a protein by proteolysis or manipulation of the structural gene, or premature termination of protein elongation due to the presence of a termination codon in its structural gene as a result of a nonsense mutation.

For purposes of the present invention, the term "uncleaved" refers to refers to a protein or polypeptide that is not cleaved by furin. For example, the furin cleavage site REKR between a gp120 and gp41 may be mutated to SEKS, which results in a gp140 that is not cleaved into gp120 and gp41 by furin.

For purposes of the present invention, the term "vaccine" refers to a biological compound or an agent used to improve immunity to a particular disease. The agent injected into a human or animal body stimulates the body's immune system to recognize the agent as foreign, destroy it, and keep a record of it, so that the immune system can more easily recognize and destroy any of these microorganisms that it later encounters. For example, an HIV vaccine improves the production of neutralizing anti-HIV antisera.

For purposes of the present invention, the term "vector" and the term "suitable vector" refer to any vehicle used to transfer genetic material to a target cell, such as a plasmid or a viral vector. A vector may also be cloning vector or expression vector. A vector may incorporate a nucleic acid sequence encoding a polypeptide or protein and any desired control sequences. It may bring about the expression of the nucleic acid sequence. The choice of the vector will typically depend on the compatibility of the vector with a host cell into which the vector is to be introduced. A vector may include, but is not limited to, a virus (e.g., adenovirus or poxvirus), naked DNA, oligonucleotide, cationic lipid (e.g., liposome), cationic polymer (e.g., polysome), virosome, nanoparticle, or dentrimer. The nucleic acid material of a viral vector may be encapsulated, e.g., in a lipid membrane or by structural proteins (e.g., capsid proteins), that may include one or more viral polypeptides (e.g., an envelope glycoprotein). The viral vector can be used to infect cells of a subject, which, in turn, promotes the translation of the heterologous gene(s) of the viral vector into a protein product (e.g., one or more of the recombinant gp140 Env polypeptides described herein, such that a stabilized trimer of the invention is formed).

For purposes of the present invention, the term "virus" refers to an infectious agent that is unable to grow or reproduce outside a host cell and that infects mammals (e.g., humans) or birds.

For purposes of the present invention, the term "wild-type" and the term "native," when made in reference to a gene, refers to a gene that has the characteristics of a gene isolated from a naturally occurring source. The term "wild-type" and the term "native," when made in reference to a gene product, refers to a gene product that has the characteristics of a gene product isolated from a naturally occurring source. The term "naturally-occurring" as applied to an object refers to the fact that an object can be found in nature. A wild-type gene is frequently that gene which is most frequently observed in a population and is thus arbitrarily designated the "normal" or "wild-type" form of the gene.

DESCRIPTION

Embodiments disclosed herein provide an approach to capture various forms of recombinant HIV-1 envelope protein (gp140) and recombinant gp140 trimers. A recombinant HIV-1 gp140 can be engineered based on an HIV-1 envelope sequence from any different clades or strains of HIV-1. In some embodiments, engineered HIV-1 envelope protein (gp140) from different clades or strains of HIV-1 are purified from a culture medium under mild conditions that cause minimal, if any, perturbation to the structure of oligomeric state of gp140.

AIDS (acquired immune deficiency syndrome) caused by the human immunodeficiency virus-1 (HIV-1) is a global epidemic. More than 30 million people worldwide currently live with HIV infection and nearly 2 million people die of AIDS every year. Nine genetic subtypes and numerous circulating recombinant forms have been identified. Coupled with this diversity is the extraordinary evolution of the viral envelope protein (Env) in response to host immune pressures. Designing an Env immunogen that can stimulate antibodies (Abs), which in turn can block entry of genetically diverse HIV-1 viruses, has remained as the "holy grail" of the HIV vaccine field.[1,2]

The trimeric Env spike of the HIV-1 virion is the virus entry machine. A trimeric Env spike of the HIV-1 virion is a trimer of hetero-dimer composed of glycoproteins gp120 and gp41 produced by cleavage of the precursor protein gp160.[3,4] The gp41 is a transmembrane glycoprotein displayed on the surface of the viral membrane. The entry of HIV-1 involves a series of well-orchestrated interactions between these proteins and the receptor molecules present on the target cell.[5] The first step might be the capture of the virus through interactions between the V1V2 domain of gp120 and a surface molecule such as the α4β7 integrin of the mucosal T lymphocytes.[6,7] This first step might bring the virus into close proximity to CD4, the primary receptor for HIV-1. Binding to CD4 causes a conformational change in gp120, exposing a site in the V3 domain that binds to the chemokine co-receptor CCR5 or CXCR4.[8-13] A series of conformational changes ensue resulting in the insertion of the gp41 fusion peptide into the host cell membrane.[14] The viral lipid bilayer fuses with the plasma membrane releasing the nucleocapsid core into the target cell.[15] Therefore, Env-specific Abs that can interfere with any of the steps common to diverse HIV-1 viruses can prevent transmission of HIV into the host.

Several human monoclonal Abs (mAbs), referred to as broadly neutralizing Abs (BnAbs), have been discovered that can neutralize infection of a large spectrum of genetically diverse HIV-1 viruses. These include, for instance, BnAbs b12 and VRC01 that bind to the CD4 binding site (bs) of gp120, 2F5 and 4E10 that bind to the membrane proximal external region (MPER) of gp41, and PG9 and PG16 that bind to the V1V2 domains of the trimer.[16,17,18,19] Most of these Abs recognize conformational epitopes and are produced either by "elite controller" individuals with chronic HIV infections, or by selection of rare B cell clones present in HIV-1 infected individuals.[20] They also exhibit unusual features such as the presence of a long heavy chain 3 complementarity determining region (CDR) covering a large area of the epitope as well as dozens of somatic mutations introduced by a process known as "affinity maturation" driven by the evolving envelope protein.[21] Attempts to induce such BnAbs in animal models, or in humans, by vaccination with recombinant Env immunogens have thus far failed.[22,23,24,25]

One reason for this failure may be that the subunit Env immunogens do not recapitulate the trimeric structure of the native Env spike present on the HIV-1 virion.[26] It has been hypothesized that exposure to "native" trimers can lead to activation and expansion of rare B cell clones of the right BnAb lineage.[27] Furthermore, such a trimer can also be used as a scaffold to engineer variants that represent a common structure present in diverse HIV-1 strains. However, production of Env trimers that mimic the native spike has remained a challenge, in part because the recombinant trimers either are unstable or aggregate.

Recently, Ringe et al discovered that an HIV-1 subtype A isolate BG505 naturally produces relatively stable trimers.[26] By further stabilizing the trimer with mutations that cross-link cleaved gp120 and gp41 through a disulfide bond (SOSIP mutations), "native-like" trimers are produced.[26] These "native-like" trimers are then captured by the BnAb 2G12 and purified.[26,28] The structures of the trimers complexed with various BnAbs are determined by cryo-electron microscopy (EM) and X-ray crystallography.[29,30] However, this Ab-based approach has inherent limitations since the gp140 structure and it epitope signatures vary from one HIV strain to another because of the amino acid sequence differences (HIV envelope protein is frequently mutated). Thus, this Ab-based approach is not as effective with diverse HIV-1 strains that might differ in the epitope signature.[31] For example, to create the epitope binding site for 2G12, the wild-type BG505 gp140 is mutated by changing Thr332 to Asn.[26] Moreover, the BnAb 2G12 is not readily available, prohibitively expensive, and not practical for vaccine manufacture.

Based on investigations on the design of HIV-1 Env immunogens and efficient vaccine delivery systems,[32,33,34] embodiments of the present invention provide a new system to isolate and characterize Env trimers, potentially from any HIV-1 virus strain. First, an Env recombinant protein is constructed by attaching a highly specific tag such as an eight amino acid (aa) STREP-TAG® II separated from the carboxy terminus (C-terminus) of a recombinant gp140 by a long linker. The long linker makes the highly specific tag accessible for binding by a binding molecule bound on a solid matrix. The Env recombinant protein can be efficiently captured by a bind molecule such as STREP-TACTIN®, a specially-engineered streptavidin ligand, directly from a culture medium (culture supernatant). The Env recombinant protein bound to STREP-TACTIN® can then be dissociated under mild conditions to generate ~95% pure Env recombinant protein in a single step. Second, embodiments of the present invention develop a screening strategy to optimize any Env recombinant protein construction for maximal trimer production. For example, the JRFL Env gp140 selected by this approach produce ~70% of recombinant gp140 as trimers. Third, the cleaved JRFL Env recombinant trimers exhibit the classic three-blade propeller shape[35] and their biochemical and antigenic properties are consistent with the native trimers. Fourth, according to embodiments, both cleavage and proper glycosylation are critical for maturation of recombinant gp140 into authentic trimers. Although recombinant gp140 can trimerize without cleavage, uncleaved trimers enter aberrant pathways generating hyper-glycosylated and conformationally heterogeneous particles. Finally, the trimers, including the cleaved propeller trimers, show micro-heterogeneity in the extent of gp41 glycosylation.

Tags such as hexa-histidine or STREP-TAG® II (SEQ ID NO: 2) have often been fused to a protein of interest. A binding molecule that is specific to the tag and bound to a solid matrix such as an agarose bead can be used to capture the tag and the protein attached to it. However, previous attempt to selectively capture and purify HIV-1 gp140 envelope protein, by using either a hexa-histidine tag or a STREP-TAG® fused to HIV-1 gp140, from a crude preparation II fails. The reason for the failure may be that a tag such as STREP-TAG® II or hexa-histidine is occluded when it is attached to the base of the gp140 structure. Consequently, the large STREP-TACTIN® beads used to capture the STREP-TAG® II (or the Nickel beads used to capture the histidine tag) may clash with the carboxy terminus of gp140 to which the tag is attached. The glycan shield containing up to 12 large complex glycans that are also attached to the carboxy terminal helix may make the tag even more sterically hindered, which makes the clashes even worse.

According to some embodiments of the present invention, separating a tag from the base of a gp140 envelope trimer by a long linker solves the problem that a tag is sterically hindered by the base of gp140. FIG. 1 is a schematic diagram showing recombinant trimer 110 of envelope gp140 protein fused to tag 112 through long linker 116 according to one embodiment of the present invention in comparison with a recombinant trimer 110 of envelope gp140 protein fused to tag 112 without long linker 116. As shown in FIG. 1, tags 112 not separated from the base of recombinant trimer 110 are sterically hindered by the base of recombinant trimer 110 of envelope gp140 protein and cannot be captured by binding molecule 122 bound on solid matrix 124. Contrarily, by being located further away from the base of recombinant trimer 110 of envelope gp140 protein, tag 112 can be captured by binding molecule 122 bound on solid matrix 124. Binding molecule 122 specifically binds to tag 112 and therefore catches recombinant trimer 110 of envelope gp140 protein which is fused to tag 112 through long linker 116. The separation of tag 112 from the base of recombinant trimer 110 of envelope gp140 protein through long linker 116 allows the capture of near homogenous recombinant trimers 110 directly from a culture medium under a mild condition. Recombinant trimer 110 of envelope gp140 protein purified from the culture medium mimics a native HIV-1 envelope trimer. To capture recombinant trimer 110 of envelope gp140 protein, binding molecule 122 may be a molecule that specifically interacts with tag 112, such as a molecule of streptavidin, nickel, etc. Solid matrix 124 may be an agarose bead. In some embodiment of the present invention, beads may be contained in a chromatography column as a stationary phase to purify recombinant trimers.

FIG. 1 is only an illustrative example of a representative recombinant trimer that can be purified directly from a culture medium under mild condition. A tag that can be used to fuse with a recombinant HIV-1 gp140 for purification is not limited to STREP-TAG® II, which is shown in FIG. 1 as an example. Any tag that can be captured by a binding molecule immobilized on a solid matrix can be used. For example, in addition to STREP-TAG® II, a tag may be an affinity tag such as a strep-tag other than STREP-TAG® II, a hexa-histidine tag, an octa-histidine tag, a chitin binding protein (CBP) tag, a maltose binding protein (MBP) tag, a polyglutamate tag, a glutathione-S-transferase (GST) tag, a FLAG-tag, an SBP-tag, a softag, etc. A tag may also be an epitope tag such as a V5-tag, Myc-tag, HA-tag, E-tag, VSV-tag, etc. The tags listed herein are not exclusive. One of ordinary skill in the art would readily appreciate that any tag that is suitable for purification of a recombinant trimer described herein may be utilized.

Particularly, in some embodiments, a recombinant protein comprises a recombinant HIV-1 gp140, a linker, and a tag, wherein the recombinant HIV-1 gp140 is fused to the tag through the linker between the tag and C-terminus of the recombinant HIV-1 gp140. The linker is long enough to make the tag accessible for finding by a binding molecule bound on a solid matrix; or in other words, the linker is sufficiently long so that the tag is accessible for binding by a binding molecule bound on a solid matrix. The length of the linker varies according to the needs of purifying different types of trimers. The linker may be a flexible linker or a rigid linker. Embodiments provide various linkers with different length. In some embodiments, the linker may be 20 or more amino acids in length. In some embodiments, the linker is 23 or more amino acids in length. In some embodiments, the linker. In some embodiments, the linker may be 27 or more amino acids in length. For example, Foldon sequence (SEQ ID NO: 1) which has 27 amino acids can also be used as a linker.

The recombinant proteins can be expressed in cells and be secreted from the cells into culture medium in which the cells grow. To secret the recombinant protein from cells expressing the recombinant protein into cell culture medium in which the cells grow, a secretion signal peptide may be attached to N-terminus of the recombinant HIV-1 gp140. In some embodiments, the secretion signal peptide is human CD5 secretion signal peptide. Once expressed in cells, the recombinant protein is secreted into the culture medium in which the cells expressing the recombinant protein grow. The recombinant protein then assembles into recombinant trimers that mimic native HIV-1 envelope trimers.

The recombinant proteins and recombinant trimers assembled in culture medium are easy to be captured and purified with a binding molecule bound and immobilized on a solid matrix. The binding molecule that specifically targets to a tag separated from a recombinant gp140 protein or a recombinant trimer base by a linker will access the tag without steric hindrance. Therefore, the binding molecule catches the recombinant gp140 fused to the tag. The binding molecule that is specific to a tag fused to a recombinant HIV-1 gp140 may be STREP-TACTIN® or Nickel beads. The solid matrix that the binding molecule bound on may be agarose beads. This approach allows the capture of near-homogeneous recombinant gp140 and trimers directly from culture medium under a mild condition. Under mild condition, the recombinant HIV-1 envelope trimer purified from the culture medium mimics a native HIV-1 envelope trimer.

Figure 2:
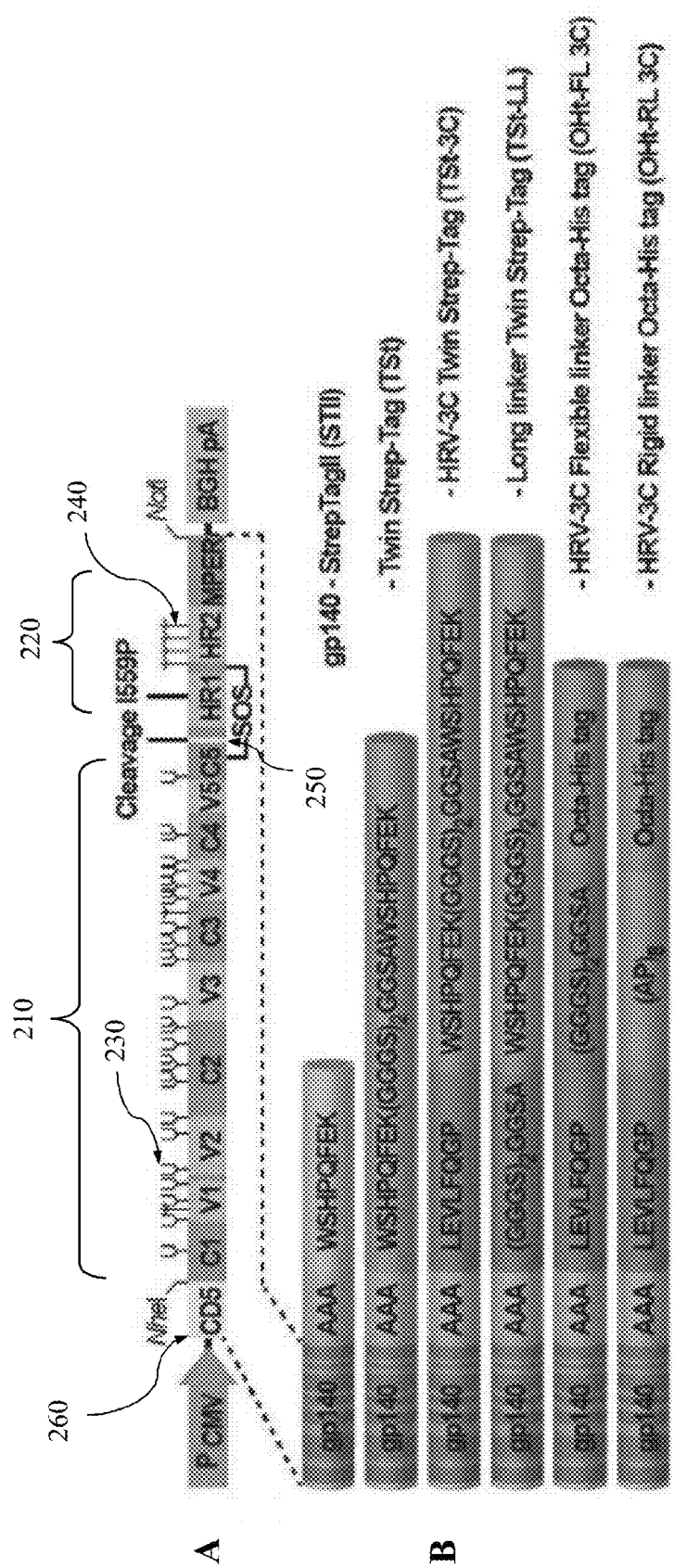
FIG. 2 is a set of schematic images of gp140 expression cassette encompassing various exemplary linkers and tags attached to an HIV-1 gp140 C-terminus according to some embodiments of the present invention.

FIG. 2 is a schematic image of gp140 expression cassette encompassing various exemplary linkers and tags attached to C-terminus of a recombinant HIV-1 gp140. In Panel A of FIG. 2, $P_{CMV}$ refers to CMV promoter and CD5 refers to secretion peptide; C1-C5 are conserved domains in gp120 subunit 210, and V1-V5 are variable domains in gp120 subunit 210; Heptad repeats 1 and 2 (HR1 and HR2) and membrane proximal external region (MPER) are regions in gp41 subunit 220. Both gp120 and gp41 have many N-linked glycosylation sites (see trees 230 and trees 240). The positions of a Furin Cleavage site is located within a junction between the gp120 subunit 210 and the gp41 subunit 220. Panel A of FIG. 2 also shows disulfide bond mutations (SOS) and I559P mutation in the gp140 expression cassette. A secretion peptide 260, such as a human CD5, is fused to C1 domain at N-terminal region of the gp120 subunit 210. Panel B of FIG. 2 is a schematic drawing illustrates various exemplary linkers and tags attached to HIV-1 gp140 C-terminus. The amino acid sequence of each tag or linker is shown in the boxes. HRV-3C refers to human rhinovirus protease cleavage site.

FIG. 2 is only an illustrative representation of a gp140 expression cassette encompassing a recombinant HIV-1 gp140. Tags and linkers that can be used for fusing with a recombinant HIV are not limited to the linker and tag shown in FIG. 2. One of ordinary skill in the art would readily appreciate that any linker and tag that are suitable for constructing a recombinant trimer described herein may be utilized.

Embodiments provide various linkers and tags as examples. For example, tags may be a STREP-TAG® II (SEQ ID NO: 2) or a poly-His tag such as an octa-histidine (His) tag (SEQ ID NO: 3), a hexa-histidine tag (SEQ ID NO: 4), etc. In some embodiments, an octa-histidine (SEQ ID NO: 3) tag is used instead of a hexa-histidine tag (SEQ ID NO: 4) because the former is more specific than the latter. In some embodiments, for example as shown in FIG. 2, a linker is an $(Ala)_3$ linker which comprises three alanines (Ala) at the N-terminus of the linker sequence. The length of a linker to separate a tag from a recombinant gp140 varies according to the needs for purifying different types of recombinant gp140. In one embodiment, the sequence of the linker comprises SEQ ID NO: 5, which has 23 amino acids in length. In some embodiments, a linker may have a sequence of SEQ ID NO: 6, SEQ ID NO: 7, SEQ ID NO: 8, or SEQ ID NO: 9, in which the linker comprising SEQ ID NO: 8 is an HRV-3C flexible linker, and the linker comprising SEQ ID NO: 9 is an HRV-3c rigid linker. In some embodiment, a linker may be a foldon sequence (27aa) that has an amino acid sequence comprises SEQ ID. NO: 1.

As illustrated in Panel B of FIG. 2, a linker and a tag may be shown as an extended tag that encompasses both the sequence of a linker and the sequence of a tag. For example, as extended tag may be Twin STREP-TAG® (TSt), HRV-3C Twin STREP-TAG® (TSt-3C), HRV-3C Twin STREP-TAG® (TSt-3C), Long linker Twin STREP-TAG® (TSt-LL), HRV-3C Flexible linker octa-His tag (OHt-FL 3C) and HRV-3C Rigid linker octa-His tag (OHt-RL 3C). Some of the linkers, for example, HRV-3C Twin STREP-TAG® (TSt-3C) and HRV-3C Twin STREP-TAG® (TSt-3C), comprise a portion of a sequence from a tag. This portion of sequence functions as a part of linker to extend the amino acid length between a tag and C-terminus of a recombinant HIV-1 gp140.

Accordingly, a series of recombinant proteins are engineered by fusing the gp140 C-terminus to a tag, such as a hexa-histidine tag, an octa-histidine tag, or a STREP-TAG® II tag, with various linkers in the middle to separate the tag from the gp140 base. The recombinant HIV-1 gp140 may be derived from any HIV-1 gp140. For example, in some embodiments, the HIV-1 clade B JRFL gp140 and clade A BG505 gp140 sequences are used as templates to engineer the recombinant proteins, respectively. Further, in some embodiments, a recombinant HIV-1 gp140 protein comprising a gp120 and a gp41 ectodomain may have a sequence truncated at amino acid residue 664 (aa664) (based on HXB2 numbering) or at a position not beyond aa664. The gp120 and the gp41 ectodomain are joined via a junction sequence that contains a furin cleavage site REKR. In some embodiments, the furin cleavage site REKR is mutated to SEKS, and such mutation results in a recombinant gp140 that is furin cleavage resistant (CR). In come embodiments, the recombinant gp140 is furin cleavage proficient (CP), in which the furin cleavage site REKR is mutated to RRRRRR (SEQ ID NO: 13).

According to some embodiments, a recombinant HIV-1 gp140 may further comprise three "SOSIP" mutations that include A501C, T605C, and I559P. In some embodiments, a recombinant HIV-1 gp140 may further comprise five "stabilizing" mutations which include I535M, Q543L, S553N, K567Q, and R588G. The A501C and T605C mutations create an intra-protomer disulfide bond between gp120 and gp41. The I559P mutation is a point mutation wherein the isoleucine residue at position aa559 of a polypeptide chain of an HIV-1 gp140 is replaced by a proline residue. The I559P mutation strengthens inter-subunit interactions.

Embodiments of the present invention also provide methods to produce recombinant trimers that mimic native HIV-1 Env trimers. The recombinant trimers can be purified from a culture medium for growing cells that express and secrete the recombinant proteins described above.

In some embodiment, recombinant trimers are uncleaved recombinant trimers. Particularly, the uncleaved recombinant trimers are assembled by a recombinant protein that is not cleaved by furin. This uncleaved recombinant protein comprises a recombinant HIV-1 gp140 fused to a tag through a linker. The linker is sufficiently long so that the tag is accessible for binding by a binding molecule bound on a solid matrix. The recombinant HIV-1 gp140 comprises two subunits: a gp120 and a gp41 ectodomain that are connected together via a junction sequence (also called a junction peptide). The gp41 ectodomain may further have a truncation at aa664 or have a truncation at a position not beyond aa664 based on HXB2 numbering. The junction sequence between the gp120 and gp41 ectodomain is absent of a furin cleavage site REKR but instead contains a furin cleavage resistant sequence SEKS. Therefore, the recombinant HIV-1 gp140 are furin cleavage resistant and will not be cleaved by furin. To secret the recombinant protein into a culture medium, a secretion signal peptide such as a human CD5 secretion signal peptide is fused at N-terminus of the recombinant HIV-1 gp140. When the recombinant protein comprising a recombinant HIV-1 gp140 fused to a tag through a linker disclosed herein is expressed in a cell growing in a culture medium, the recombinant protein is secreted from the cell into the culture medium and assembles into trimers in the culture medium.

Embodiments also provide cleaved trimers, which are recombinant trimers of heterodimers composed of a cleaved gp120 and a cleaved gp41ectodomain. A tag is fused to C-terminus of the cleaved g41 ectodomain through a linker. The cleaved gp120 and cleaved gp41 ectodomain are produced by a cleavage of a recombinant protein comprising a recombinant HIV-1 gp140 fused to a tag through a linker. The recombinant HIV-1 gp140 has a gp120 and a gp41 ectodomain connected by a junction sequence between the gp120 and the gp41 ectodomain. The junction sequence includes a furin cleavage site REKR. To improve cleavage efficiency, the furin cleavage site REKR is mutated to RRRRRR (SEQ ID NO: 13). The linker is long enough to make the tag accessible for finding by a binding molecule bound on a solid matrix; or in other words, the linker is sufficiently long so that the tag is accessible for binding by a binding molecule bound on a solid matrix. In some embodiments, the linker has an amino acid sequence comprising 20 amino acids in length or longer. In some embodiments, the linker has an amino acid sequence comprising 23 amino acids in length or longer. A secretion signal peptide such as a human CD5 secretion signal peptide is fused at N-terminus of the recombinant HIV-1 gp140 fused to a tag for secretion of the recombinant protein into culture medium one the recombinant protein is expressed in cells growing in the culture medium. As a result, when the recombinant protein is expressed in a cell, the recombinant protein is secreted from the cell into a culture medium in which the cell grows and is cleaved by furin into a cleaved gp120 and a cleaved gp41ectodomain. The cleaved gp120 and the cleaved gp41 ectodomain form a heterodimer in which the cleaved gp120 and the cleaved gp41 ectodomain are covalently associated through a disulfide bond. The heterodimer assembles into trimers that mimic native HIV-1 envelope trimers in the culture medium. In the heterodimer, the tag is fused to the C-terminus of the cleaved gp41 ectodomain through the linker. The linker is long enough to separate the tag from the trimer base of the heterodimer, as a result, the tag is accessible for binding by a binding molecule bound on a solid matrix.

According to embodiments, in both cleaved and uncleaved trimers, a tag may be a STREP-TAG® II tag, a hexa-histidine tag, or an octa-histidine tag. A linker is in the middle of the tag and the recombinant HIV-1 gp140 and separates the tag from the recombinant gp140 base. The linker is long enough to make the tag accessible for finding by a binding molecule bound on a solid matrix; or in other words, the linker is sufficiently long so that the tag is accessible for binding by a binding molecule bound on a solid matrix. The linker may be flexible or rigid, and varies in length according to the needs of purifying different types of trimers. In some embodiments, a linker is 20 amino acids in length or longer. In some embodiments, a linker is 23 amino acids in length or longer. In one embodiment, a linker comprises a foldon sequence that is 27 amino acids in length (SEQ ID NO: 1).

In producing both cleaved and uncleaved trimers, three "SOSIP" mutations may be introduced into a sequence of an HIV-1 gp140 to construct a recombinant HIV-1 gp140. The "SOSIP" mutations include A501C, T605C, and I559P. In some embodiments, the recombinant HIV-1 gp140 may also encompass five "stabilizing" mutations (in comparing with a native HIV-1 gp140). The five "stabilizing" mutations include I535M, Q543L, S553N, K567Q, and R588G. In some embodiments, the recombinant HIV-1 gp140 is engineered based on the sequence of an HIV-1 clade B gp140 such as JRFL gp140 or SF162 gp140. In some embodiment, the recombinant HIV-1 gp140 is engineered based on the sequence of an HIV-1 clade A gp140 such as BG505 gp140. For example, embodiments provide a recombinant protein JRFL SOSIP(1-5).R6.664 gp140 that is a Strep-Tagged gp140 protein engineered by using an HIV-1 clade B JRFL gp140 as a template. The recombinant protein JRFL SOSIP (1-5).R6.664 gp140 has an amino acid sequence corresponding to SEQ ID NO: 10. Embodiments also provide a recombinant protein BG505 SOSIP.R6.664 gp140 which is a Strep-Tagged gp140 protein engineered by using an HIV-1 clade A BG505 gp140 as a template. The recombinant protein BG505 SOSIP.R6.664 gp140 has an amino acid sequence corresponding to SEQ ID NO: 11. Embodiments also provide a recombinant protein SF162 SOSIP.R6.664 gp140 is a Strep-Tagged gp140 protein engineered by using an HIV-1 clade B SF162 gp140 as a template. The recombinant protein SF162 SOSIP.R6.664 gp140 has an amino acid sequence corresponding to SEQ ID NO: 12.

In some embodiments, a recombinant protein comprising a recombinant HIV-1 gp140 attached to a tag through a linker at C-terminus of the recombinant HIV-1 gp140 is expressed in mammalian cell lines such as HEK293F (293F), 293T, 293EXPI, CHO, HEK293S GnTI⁻ (GnTI⁻), etc. When the recombinant HIV-1 gp140 is expressed in cells growing in a culture medium, the secretion signal peptide fused at the N-terminus of the recombinant HIV-1 gp140 helps the recombinant protein translocate from inside the cells into the culture medium in which the recombinant protein assembles into trimers.

According to embodiments, cells expressing a recombinant protein are transfected with a recombinant DNA encoding a recombinant protein comprising recombinant HIV-1 gp140 fused to a tag through a linker. The linker is sufficiently long so that the tag is accessible for binding by a binding molecule bound on a solid matrix. The linker may be flexible or rigid, and varies in length according to the needs of purifying different trimers. In some embodiments, the linker is at least 20 amino acids. In some embodiments, the linker is 23 amino acids in length or longer. In one embodiment, 293F cells are transfected with a recombinant DNA encoding a recombinant protein comprising recombinant HIV-1 gp140 fused to a tag through a linker. The recombinant protein may be expressed in the transfected 293F cells with a control of a promoter. The promoter may be a constitutive promoter or an inducible promoter. In one embodiment, a promoter regulating the expression of the recombinant protein is promoter CMV. Once expressed, the recombinant protein is secreted from the 293F cells into the culture medium and assembles into trimers in the culture medium. The recombinant protein without furin cleavage site will assembles into uncleaved trimers in the culture medium. The recombinant protein with a furin cleavage site, including an enhanced furin cleavage site, will be cleaved by furin into a cleaved gp120 and a cleaved gp41 ectodomain and form a heterodimer, wherein the cleaved gp120 and the cleaved gp41 are covalently associated through a disulfide bond.

In one embodiment, GnTI⁻ cells are transfected with a recombinant DNA encoding a recombinant protein comprising recombinant HIV-1 gp140 fused to a tag through a linker. The recombinant protein may be expressed in the transfected GnTI⁻ cells with a control of a promoter. The promoter may be a constitutive promoter or an inducible promoter. In one embodiment, a promoter regulating the expression of the recombinant protein is promoter CMV. Once expressed or produced, the recombinant protein is secreted from the GnTI⁻ cells into the culture medium. The recombinant protein without furin cleavage site will assembles into uncleaved trimers in the culture medium. The recombinant protein with a furin cleavage site, including an enhanced furin cleavage site, will be cleaved by furin into a cleaved gp120 and a cleaved gp41 ectodomain and form a heterodimer, wherein the cleaved gp120 and the cleaved gp41 are covalently associated through a disulfide bond.

In some embodiments, a recombinant DNA encoding a recombinant HIV-1 gp140 that has a furin cleavage site, including an enhanced furin cleavage site RRRRRR, is co-transfected into cells with a recombinant DNA encoding a protein furin. Such co-transfection enhances the cleavage efficiency and increases the production of heterodimers formed by cleaved gp120 and gp41 ectodomain.

According to embodiments, a recombinant HIV-1 gp140 expressed in GnTi⁻ cells is partially glycosylated, while a recombinant HIV-1 gp140 expressed in 293F cells is hyperglycosylated or fully glycosylated. In some embodiments, the recombinant gp140 purified by the method disclosed herein is about 95% pure. According to embodiments, cleavage of gp140 is not essential for trimerization, but it triggers a conformational change that channels trimers into correct glycosylation pathways generating compact three-blade propeller-shaped trimers. Most uncleaved trimers enter aberrant pathways resulting in hyper-glycosylation and conformational heterogeneity. Embodiments of the present invention establish a broadly applicable system for production and characterization of HIV-1 trimers and generate new insights into the assembly and maturation of HIV-1 trimers that will have implications to the design of an effective HIV vaccine. A vaccine developed from the recombinant trimer disclosed herein that mimics native spike may elicit entry-blocking antibodies and prevent HIV infection.

Corresponding to recombinant proteins described above, embodiments of the present invention also provide a recombinant DNA encoding a recombinant protein for making recombinant trimers that mimic native HIV-1 envelope trimers. Accordingly, a recombinant DNA is constructed to encompass a nucleic acid sequence encoding a recombinant protein, wherein the recombinant protein encompasses a recombinant HIV-1 gp140 fused to a tag through a peptide linker at C-terminus of the recombinant HIV-1 gp140. The peptide linker is sufficiently long so that the tag is accessible for binding by a binding molecule bound on a solid matrix. In some embodiments, the peptide linker has a length of 20 amino acids or longer. In some embodiments, the peptide linker has a length of 23 amino acids or longer. A nucleic acid sequence encoding a secretion signal peptide is attached at 5' end of the sequence encoding the recombinant HIV-1 gp140. The recombinant DNA may be transfected into cells for expression of the fusion protein. Cells carrying the recombinant DNA after transfection may grow in a medium to allow the expression of the recombinant protein. The recombinant protein expressed in the cells is then secreted from the cells into culture medium and assembles into recombinant trimers that mimic native HIV-1 Env trimers.

According to embodiments of the present invention, the peptide linker may vary in length according to the needs of purifying different types of trimers. The peptide linker is selected for separating the tag from the recombinant HIV-1 gp140, so that a binding molecule specifically target the tag will not be sterically hindered to access the tag. The peptide linker comprises an amino acid sequence that is long enough to make the tag accessible for binding by a binding molecule bound on a solid matrix, and is flexible enough to freely expose the tag for capture by the binding molecule. Hence, a peptide linker used to separate the tag and the recombinant HIV-1 gp140 may be flexible or rigid. In some embodiment, a peptide linker is at least 20 amino acids in length. In some embodiment, a peptide linker may have 23 amino acids in length. In some embodiment, a peptide linker is longer than 23 amino acids in length. The nucleic acid sequence for a peptide linker may vary corresponding to the peptide linker selected. In some embodiments, the amino acid sequence of the linker contains repeats of glycine as well as amino acids such as alanine and serine, and proline. In some embodiments, a peptide linker may have an amino acid sequence of SEQ ID NO: 5, SEQ ID NO: 6, SEQ ID NO: 7, SEQ ID NO: 8, or SEQ ID NO: 9, in which the peptide linker comprising SEQ ID NO: 8 is an HRV-3C flexible linker, and the peptide linker comprising SEQ ID NO: 9 is an HRV-3c rigid linker. In some embodiment, a peptide linker may be a foldon sequence (27aa) that has an amino acid sequence comprises SEQ ID. NO: 1.

A nucleic acid sequence of a tag may also vary according to need. For example, a nucleic acid sequence of a tag may encode a STREP-TAG® II comprising SEQ ID NO: 2, an octa-histidine tag comprising SEQ ID NO: 3, or a hexa-histidine tag comprising SEQ ID NO: 4.

Correspondingly, the recombinant DNA in some embodiment encompasses a nucleic acid sequence encoding a recombinant HIV-1 gp140 comprising a gp120 and a gp41 ectodomain, in which the gp120 and the gp41 ectodomain are joined together by a junction sequence containing a furin cleavage site REKR. In some embodiments, the gp41 ectodomain is truncated at aa664 or a position not beyond aa664, based on HXB2 numbering. In some embodiments, a nucleic acid sequence encoding a furin cleavage site REKR is mutated to encoding a sequence of SEKS, resulting in producing a recombinant HIV-1 gp140 that is furin cleavage resistant. In some embodiments, a nucleic acid sequence encoding a furin cleavage site REKR is mutated to encoding a sequence of RRRRRR, resulting in producing a recombinant HIV-1 gp140 that is furin cleavage proficient.

In some embodiments, a recombinant DNA has a nucleic acid sequence encoding a recombinant HIV-1 gp140 that has "SOSIP" mutations comprising A501C, T605C, and I559P. In some embodiments, the recombinant DNA has a sequence encoding a recombinant HIV-1 gp140 that has both "SOSIP" mutations and "stabilizing" mutations. The "stabilizing" mutations include I535M, Q543L, S553N, K567Q, and R588G.

According to one embodiment of the present invention, a nucleic acid sequence encoding a recombinant protein comprising a recombinant HIV-1 gp140 fused to a tag through a linker disclosed herein may be derived from any HIV-1 clade sequence. For example, a recombinant DNA may have a nucleic acid sequence encoding a recombinant protein engineered based on a sequence of an HIV-1 clade B JRFL gp140 or HIV-1 clade B SF162 gp140. In another embodiment, a recombinant DNA may have a nucleic acid sequence encoding a recombinant protein engineered based on a sequence of an HIV-1 clade A BG505 gp140. In one embodiment, a recombinant DNA has a nucleic acid sequence encoding a recombinant protein comprising SEQ ID NO: 10. In one embodiment, a recombinant DNA has a nucleic acid sequence encoding a recombinant protein comprising SEQ ID NO: 11. In one embodiment, a recombinant DNA has a nucleic acid sequence encoding a recombinant protein comprising SEQ ID NO: 12.

Embodiments further provide various vectors for expression the recombinant proteins comprising recombinant HIV-1 gp140 fused to a tag through a peptide linker disclosed herein (may be called tagged HIV-1 gp140). A vector may have a regulatory region operably linked to a nucleic acid sequence encoding a recombinant protein described above. The regulatory region regulates the expression of the recombinant protein in a cell carrying the vector. Once being expressed in cells carrying the vector and secreted into culture medium that the cells grow, the recombinant protein has a capacity of assembly into recombinant trimers mimicking native HIV-1 Env trimers. In some embodiment, the expression of the recombinant is regulated under a regulatory region comprising an inducible promoter, and the recombinant protein is not consistently expressed in a cell carrying the vector but can be induced as needed. In some embodiment, the expression of a recombinant protein described herein in a cell carrying the vector is controlled under a constitutively promoter. A cell carrying a vector comprising a constitutive promoter such as a CMV promoter will constitutively express the tagged recombinant HIV-1 gp140. In some embodiments, a human cytomegalovirus (CMV) promoter locates at upstream of the nucleic acid sequence encoding a recombinant protein comprising a recombinant HIV-1 gp140 attached to a tag via a peptide linker. CMV promoter is a constitutive promoter and is always active.

Embodiments further provide various vectors comprising expression cassette to construct expression vectors for producing recombinant protein described herein. In some embodiments, a vector comprising an expression cassette may comprise a regulatory region operably linked to a first nucleic acid sequence that encodes a secretion signal peptide. The first nucleic acid sequence is linked to a second nucleic acid sequence with an insertion region comprising two or more restriction sites. The insertion region is use for insertion a recombinant DNA encoding a recombinant HIV-1 gp140. The second nucleic acid sequence encodes a peptide linker and a tag. As a result, a vector to express a recombinant protein described herein may be easily constructed by insertion a recombinant nucleic acid sequence encoding a recombinant HIV-1 gp140 using the two restriction sites in the insertion region. A recombinant nucleic acid sequence encoding a recombinant HIV-1 gp140 can be engineered by either overlap-extension PCR or gene assembly PCR using appropriated set of primers, and by modification of any HIV-1 clade gp140.

In some embodiments, the insertion region has two restriction sites: NheI and NotI. In some embodiments, three alanines are located at N-terminus of the linker. In some embodiments, the sequence encoding a secretion signal peptide is a sequence encoding a human CD5 signal peptide. A promoter in the vector may be a constitutive promoter or an inducible promoter. A promoter may be a CMV promoter. In some embodiments, the vector is a plasmid vector and can be transformed into bacteria to store or to amplify, and can be transfected into mammalian cells to express the recombinant protein. The recombinant protein has the capacity to form recombinant trimers mimicking native HIV-1 envelop trimers. Once expressed in cells, the recombinant protein can be secreted into cell culture medium and assemble into recombinant trimers.

Figure 3:
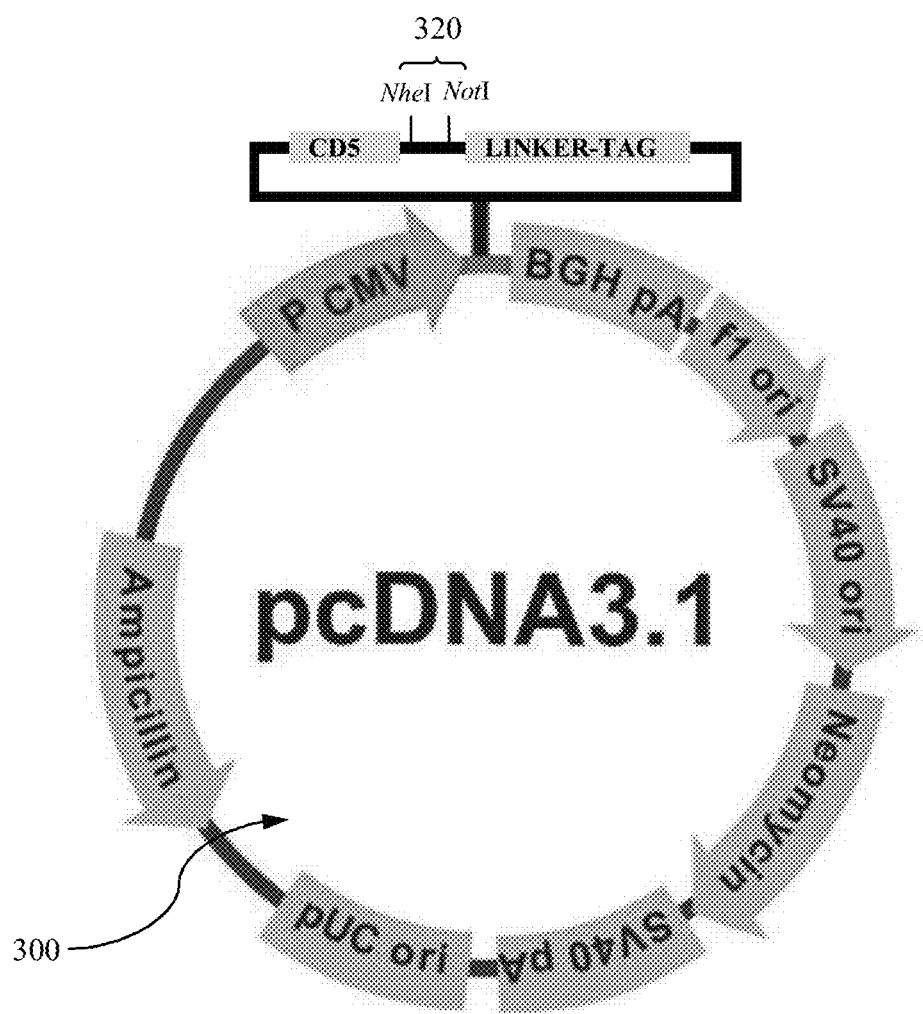
FIG. 3 is a schematic drawing of a plasmid vector comprising expression cassette according to some embodiments of the present invention.

FIG. 3 illustrates an example of a vector that comprises an expression cassette and can be used for insertion of a recombinant DNA encoding a recombinant HIV-1 gp140 and expression a recombinant HIV-1 gp140 fused to a tag via a peptide linker. As shown in FIG. 3, a vector 300 may contain a CD5 secretion signal, a peptide linker, and various tags such as STREP-TAG® II and octa-histidine tags described in Panel A of FIG. 2. In some embodiments, a peptide linker contains three alanines at the N-terminus of the linker (which is called "alanine linker"). In one example, an insertion region 320 between the CD5 signal and the alanine linker contains two or more restriction sites. The two or more restriction sites may be restriction sites NheI and NotI. These plasmid vector DNAs may be isolated from 5-alpha competent E. coli cells and be digested with NheI and NotI and dephosphorylated with alkaline phosphatase. Recombinant DNA encoding a recombinant HIV-1 gp140 may be inserted into the vector at the restriction sites NheI and NotI.

Embodiments provide methods to purify recombinant trimers described herein. According to embodiments, the material used to capture a recombinant HIV-1 envelope protein gp140 and recombinant trimers may be a binding molecule bound or immobilized on a solid matrix such as agarose beads. Binding molecules may be SREP-TAC-TIN®, nickel, etc.

In some embodiments, purification of the recombinant proteins or trimers may be carried out by centrifugation. In some embodiments, purification of the recombinant proteins or trimers is carried out by affinity chromatography and by size exclusion chromatography (SEC), and the size exclusion chromatography is conducted after the affinity chromatography is conducted.

In some embodiments of the present invention, purification is achieved by column chromatography. By this approach, a binding molecule bound on a solid matrix is packed onto a column, and a culture medium containing the recombinant protein or the recombinant trimer runs through the column to allow the recombinant protein or the recombinant trimer bind to the binding molecule. Subsequently, a wash buffer runs through the column and an elution buffer is applied to the column to elute the recombinant protein or the recombinant trimer from the solid matrix.

Alternatively, in some embodiments, purification of the recombinant protein or the recombinant trimer is done by using a batch treatment. A binding molecule bound and immobilized on a solid matrix is added into a culture medium containing the recombinant protein or the recombinant trimer in a container. After mixing, the recombinant protein or the recombinant trimer binds to the binding molecule and can be separated from the culture medium by centrifugation. For example, STREP-TACTIN® beads may be added to a culture medium containing recombinant trimers comprising STREP-TAG® to form a bead mixture allowing the binding between the STREP-TACTIN® beads and the recombinant trimers. The STREP-TACTIN® beads bound to the recombinant trimers may be then separated from the culture medium by centrifugation. Bounded trimers may further be eluted with elution buffer. Alternatively, the STREP-TACTIN® beads bound to the recombinant trimers or the recombinant proteins may be packed onto a column, followed with washing and elution on the column packed with the STREP-TACTIN® beads to purify the recombinant trimers or the recombinant proteins.

Embodiments of the present invention demonstrate that the linker approach is highly effective to directly capture a recombinant protein comprising a recombinant HIV-1 gp140 from a culture medium. In some embodiments, STREP-TACTIN® beads are directly added to a cell culture medium into which the recombinant protein is secreted. The beads that bind the recombinant protein may be separated by simple centrifugation. The recombinant protein bound on the beads may be then eluted using mild buffer conditions such as conditions containing desthiobiotin. Similarly, in some embodiments, the recombinant HIV-1 gp140 attached to an octa-histidine tag with a long linker in the middle is captured by Nickel beads. The recombinant HIV-1 gp140 bound on the Nickel beads is eluted with imidazole. In some embodiments, the linker is effective when it is ~23 amino acids or longer and both a flexible linker and a rigid linker are equally effective in capturing a recombinant gp140. In some embodiments, a linker comprises a foldon sequence of SEQ ID NO: 7. The foldon sequence has a length of 27 amino acids.

In some embodiments, the recombinant HIV-1 gp140 for producing the recombinant trimers comprises three "SOSIP" mutations (in comparing with a native HIV-1 gp140). The three "SOSIP" mutations include A501C, T605C, and I559P. In some embodiments, a recombinant HIV-1 gp140 may further encompass five "stabilizing" mutations (in comparing with a native HIV-1 gp140). The five "stabilizing" mutations include I535M, Q543L, S553N, K567Q, and R588G.

According to embodiments, a variety of recombinant gp140 variants, cleaved, uncleaved, partially glycosylated, fully glycosylated, from clades A and B, are purified by this approach. Upon purification and optimization, recombinant trimers that mimic native HIV-1 Env trimers are obtained. Since the structure of the HIV-1 trimer base is conserved among different HIV viruses, this approach can be broadly applied to produce recombinant gp140 and recombinant trimers from any HIV-1 clade or strain, wherein the recombinant trimers mimic native trimers of various HIV-1 clade or strains.

Therefore, embodiments of the present invention develop a new and simple approach to produce HIV-1 envelope trimers. In some embodiments, the C-terminus of gp140 is attached to a tag such as STREP-TAG® II with a long linker separating the tag from the massive trimer base and glycan-shield. This allows a capture of near-homogenous gp140 directly from the supernatant of culture medium. Extensive biochemical characterizations show that cleavage of gp140 is not essential for trimerization, but it triggers a conformational change that channels trimers into correct glycosylation pathways generating compact three-blade propeller-shaped trimers. Uncleaved trimers enter aberrant pathways resulting in hyper-glycosylation, nonspecific crosslinking, and conformational heterogeneity. Even the cleaved trimers show micro-heterogeneity in gp41 glycosylation.

Embodiments of the present invention are further defined in the following examples. It should be understood that these examples are given by way of illustration only. From the above discussion and these examples, one skilled in the art can ascertain the essential characteristics of embodiments of the present invention. Without departing from the spirit and scope thereof, one skilled in the art can make various changes and modifications of the invention to adapt it to various usages and conditions. Although specific terms have been employed herein, such terms are intended in a descriptive sense and not for purposes of limitation. All publications, including patents and non-patent literature, referred to in this specification are expressly incorporated by reference herein.

EXAMPLES

Example 1

Experimental Procedures

Antibodies

The following reagents are obtained through the NIH AIDS Reagent Program, Division of AIDS, NIAID, NIH: HIV-1 gp120 Monoclonal Antibody (2G12)[36, 37, 38, 39, 40] from Dr. Hermann Katinger, HIV-1 gp120 MAb (VRC01)[17] from Dr. John Mascola, PGT 121 (Cat#12343),[41] HIV-1 gp41 Monoclonal Antibody (F240)[42] and HIV-1 gp120 Monoclonal Antibody (F105)[43, 44, 45, 46] from Dr. Marshall Posner and Dr. Lisa Cavacini. The PG9,[19] PG16,[19] PGT145,[41] PGT151,[47] and b6,[16] are obtained from Scripps Research Institute and International AIDS Vaccine Initiative Neutralizing Antibody Center (IAVI NAC). Polyclonal Bas against HIV-1 JREL gp140 are raised in mice in our laboratory.

Clone Constructions

The furin-expressing plasmid, Furin: FLAG/pGEM7Zf (+), is obtained from Dr. Gary Thomas (Vollum Institute, Portland, Oreg.). The furin fragment from this plasmid is sub-cloned into pcDNA3.1(–) (Life Technologies) using EcoRI and HindIII restriction sites.

Codon optimized gp140 DNAs from JRFL-FD, SF162-FD, and CONPEP-FD are provided by Dr. Peter Kwong (Vaccine Research Center, NIH). These DNAs contained the sequence corresponding to gp120 and gp41 ectodomain up to aa683. In addition, they have human CD5 secretion signal at the 5'end, furin cleavage resistant mutation SEKS at the junction of gp120 and gp41, and bacteriophage T4 fibritin trimerization motif followed by the hexa-histidine tag at the C-terminus.[48] Using the JRFL-FD as the starting template, a series of additional mutations are introduced. These include, for instance, SOSIP mutations,[49,50] stabilizing mutations,[51] enhanced furin cleavage site RRRRRR,[52] and various truncations shown in FIG. 2 and in the following examples. JRFL gp120 clone is also constructed from the same template by polymerase chain reaction (PCR) amplification of the appropriate sequence corresponding to gp120.

BG505 (BG505.W6M.ENV.C2)[28,53] gp140 envelope sequence is codon-optimized and the optimized sequence is synthesized using the GenArt Strings technology (Life Technologies). During this process, a series of mutations are also introduced as follows: Asn at aa332 to introduce an N-linked glycosylation site that allows binding of BG505 gp140 to 2G12 BnAb;[54] SOSIP;[28] RRRRRR;[52] and various other mutations described in the following examples.

A series of modified pcDNA3.1(–) vectors are constructed, each containing CD5 secretion signal, a liker containing three alanines, and various Strep-Tag II and Octa-histidine tags described in the following examples. Restriction sites NheI and NotI are introduced in between the CD5 signal and the alanine linker. These plasmid vector DNAs isolated from 5-alpha competent E. coli cells (New England BioLabs, Inc.) are digested with NheI and NotI and dephosphorylated with FastAP alkaline phosphatase (Life Technologies).

The gp140 (and gp120) clones (recombinant DNA encoding recombinant HIV-1 gp140) are constructed by either overlap-extension PCR[55] or gene assembly PCR[56] using appropriate sets of primers. Restriction sites for NheI and NotI are introduced into the end primers. The amplified DNAs are digested with NheI and NotI and purified by agarose gel electrophoresis. The DNAs are then ligated with the NheI-NotI-digested and dephosphorylated pcDNA3.1(–) plasmid DNA. Directional insertion of gp140 DNA results in the in-frame fusion of gp140 with CD5 signal peptide at the N-terminus and the alanine linker followed by various tags at the C-terminus (see FIG. 2, Panel B).

The gp140 (and gp120) clones are transformed into 5-alpha competent E. coli cells (New England BioLabs, Inc) and the plasmid DNAs are purified using the GeneJET plasmid miniprep kit (Life Technologies). The DNAs are then sequenced to confirm 100% accuracy of the cloned gp140 DNA. For transfection into mammalian cells, the plasmid DNAs are purified using the GeneJET plasmid midiprep kit (Life Technologies) as per the manufacturer's instructions.

Small-Scale Transfection.

Suspension cells HEK293F (Life Technologies) and HEK293S GnTI⁻ (ATCC CRL-3022) are maintained in FreeStyle 293 expression medium (Life Technologies). The cells are incubated in a Multitron Pro shaker (Infors HT) at 37° C. in 8% $CO_2$. In the case of HEK293S GnTI⁻, the growth medium is supplemented with 1% heat-inactivated fetal bovine serum (FBS, Quality Biologicals). For transfection, cells are grown overnight to a density of $1\times10^6$ cells per ml. Two hours prior to transfection, 6 ml cultures are centrifuged at 100 g for 5 min and resuspended in fresh medium to a density of $3\times10^6$ cells per ml in the absence of FBS. Three ml of cells are then transferred to each well of a 16.8 ml 6 Well Clear Not Treated plates (Corning Inc.). For CR (and gp120) DNA, 6 μg of gp140 plasmid DNA is added to the cells followed by the addition of linear polyethylenimine (PEI25k, Polyscience Inc.) to a PEI:DNA (wt/wt) ratio of 3:1. For CP DNA, the cells are cotransfected with 3 μg of furin plasmid DNA. The cells are then incubated at 37° C. in 8% $CO_2$ while shaking at 130 r.p.m. overnight. After 12 h, 2 ml of fresh medium, 1 ml HyClone SFM4HEK293 medium (GE Healthcare), and protein expression enhancing sodium butyrate[57] (SIGMA-ALDRICH) to a final concentration of 2 nM are added to the cells. On day 5, the supernatant is harvested and clarified using a 0.2 μm filter (Corning Inc.).

Large-Scale Transfection

Transfection is carried out similar to the small scale transfection, but it is scaled up to 1.2 L cultures in a 2.8 L flask and incubated at 37° C. in 8% $CO_2$ while shaking at 90 r.p.m.

Small-Scale gp140 Purification

To inactivate biotin present in the supernatant, 20 μl of Bio-Lock biotin blocking solution (iba Life Sciences) is added to 5 ml of the supernatant containing the secreted gp140 (or gp120). After 30 min incubation at 4° C., 100 μl of STREP-TACTIN® beads (Qiagen) are added and allowed to rotate overnight at 4° C. The bead mixture is spun down at 200 r.p.m. to pellet the beads. The beads are then applied to a spin column (PIERCE™) and briefly centrifuged to remove residual supernatant and then washed twice with 50 mM Tris-HCl, pH 8, and 300 mM NaCl. The bound gp140 or gp120 proteins are eluted with 200 μl of STREP-TACTIN® elution buffer (2.5 mM d-Desthiobiotin (SIGMA), 25 mM Tris-HCl, pH 8, and 150 mM NaCl).

Large-Scale gp140 Purification

To prevent nonspecific protease degradation, protease inhibitor tablets (Roche Diagnostics) are added to the clarified supernatant according to manufacturer's instructions. To inactivate free biotin present in the culture medium, BioLock-biotin blocking solution (iba Life Sciences) is added and the medium is incubated at 4° C. for 30 min. The gp140 is purified by STREP-TACTIN® affinity chromatography followed by size exclusion chromatography (SEC). The supernatants are loaded onto a 1 ml STREP-TACTIN® column (Qiagen) at 0.7 ml/min using the ÄKTA prime-plus liquid chromatography system (GE Healthcare). Nonspecifically bound proteins are washed off by passing at least 20 column volumes of wash buffer (50 mM Tris-HCl, pH 8, and 300 mM NaCl) until the absorbance reaches baseline level. The Strep-Tagged gp140 proteins are then eluted with elution buffer (2.5 mM d-Desthiobiotin (SIGMA), 25 mM Tris-HCl pH 8 and 150 mM NaCl) at a flow rate of 1 ml/min. The peak fractions are pooled and concentrated using 100 kDa MWCO Amicon Ultra-4 centrifugal filter units (Millipore). The samples are then applied to a Hi-Load 16/600 Superdex-200 (prep-grade) size exclusion column (GE Healthcare) equilibrated with the gel filtration buffer (25 mM Tris-HCl, pH 8, 150 mM NaCl). Chromatography is done using the ÄKTA FPLC system (GE Healthcare) and fractions are collected and stored in 10% glycerol at −80° C.

The gp140 clones fused to hexa-histidine or octa-histidine tags are purified by HisTrap affinity chromatography followed by SEC. The culture supernatant is loaded onto a 1 ml HisTrap HP column (GE Healthcare) at a flow rate of 0.7 ml/min using the ÄKTA prime-plus liquid chromatography system (GE Healthcare). Nonspecifically bound proteins are removed using a buffer containing 50 mM Tris-HCl, pH 8, 300 mM NaCl and 20 mM imidazole until the absorbance reached baseline level. The proteins are then eluted using a 20-500 mM imidazole gradient. The peak fractions are then applied to Hi-Load 16/600 Superdex-200 (prep-grade) size exclusion column (GE Healthcare) and purified as described above.

SDS-PAGE and Blue Native (BN) PAGE

SDS-PAGE analyses are performed using 4-20% gradient Tris-glycine gels (Life Technologies) or home-made 10% gels in the presence (reducing) or absence (non-reducing) of DTT. The BLUEstain™ protein ladder 11-245 kDa (a three-color protein standard with prestained proteins covering a wide range molecular weights produce by Gold Biotechnology®) is used as a molecular weight (MW) marker. BN-PAGE is performed using the Novex® NativePAGE™ Bis-Tris gel system in 4-16% gradient gels according to manufacturer's instructions (Life Technologies). In the case of JRFL-FD, a native 4-12% gradient Tris-Glycine gel (Life Technologies) is used with Tris-Glycine buffer (Bio-Rad). The NativeMark™ unstained protein standard (Life Technology) is used as the MW marker. All gels are stained with Coomassie blue R-250 solution.

Protease Cleavage

SEC-purified gp140 trimers are incubated with 10-fold serial dilutions (1-0.001 μg/ml) of Proteinase K (Thermo Scientific) at 37° C. for 1 h. The same preparation incubated at 4° C. and 37° C. without protease is used as a negative control. The samples are electrophoresed on reducing SDS gels for cleavage resistant gp140 and non-reducing SDS gels for cleavage proficient gp140.

Deglycosylation

For STREP-TACTIN® purified gp140, 1 μl (500 Units) of PNGase F (New England BioLabs, Inc.) is used to deglycosylate 10 μg of protein in the absence of DTT following manufacturer's instructions. For SEC-purified trimers, deglycosylation is performed under native conditions using 3 μl (1,500 Units) of PNGase F per 10 μg of protein and by incubating for 5 h at room temperature.

STREP-TACTIN® ELISA

STREP-TACTIN® coated microplates (iba Life Sciences) are coated with 1 μg/ml SEC-purified gp140 trimers in a volume of 100 μl per well of buffer (25 mM Tris-HCl pH 7.6, 2 mM EDTA, and 140 mM NaCl) and incubated for 2 h at room temperature. Following 3 washes with PBST (0.05% Tween-20 in PBS), 100 μl of serially diluted antibodies (10-0.001 μg/ml) in PBS are added to the wells and the plates are incubated for 1 h at 37° C. After 3 washes with PBST, the plates are incubated with 100 μl of rabbit anti-human antibody (Santa Cruz Biotechnology) diluted 1:3,000 in PBS for 30 min at 37° C. After the final 3 washes with PBST, the reaction is developed with peroxidase (TMB Microwell Peroxidase Substrate system, KPL). The reaction is terminated by adding 100 μl of BlueSTOP™ solution (KPL) and $OD_{650}$ is recorded using VersaMax™ ELISA Microplate Reader (Molecular Devices).

Western Blotting

Polyclonal mouse antibodies against HIV-1 gp140 prepared in our laboratory are used as the primary antibody and rabbit HRP-conjugated anti-mouse IgG (H+L) is used as the secondary antibody (Novex, Life Technologies). For STREP-TAG® II detection, StrepMAB-Classic HRP conjugated antibody (iba Life Sciences, dilution 1:1,000 in PBS) is used. Band intensities are measured using Biorad Gel doc XR+System and Image Lab software.

Negative-Stain EM

Samples are diluted to 20-30 μg/ml and added to a glow-discharged carbon-coated grid. Samples are left on the grid for 2 min, blotted with a filter paper, and stained with Nano-W™ (Nanoprobes, Yaphank, N.Y.) for 30 s, with two cycles of rinsing followed by stain application. After the last round of staining, the grid is blotted and allowed to dry completely before being imaged. Grids are imaged on an FEI Tecnai T12 microscope operating at 120 kV. Images are captured at a nominal magnification of 67,000× on a Gatan UltraScan CCD using a dose of 20 electrons per Angstrom squared. Particles are selected semi-automatically using e2boxer within EMAN2 with a box width of 200 Angstroms. Reference-free 2D class averages are generated using EMAN2.[58] Briefly, several particles are manually picked to initiate automated particle picking using e2boxer within EMAN2. After automated particle picking, reference-free 2D class averages are generated using e2refine2d within EMAN2. Each sample goes through 15 iterations of 2D classification and 32 classes are generated per sample.

Example 2

Conventional Strategies have not been Very Effective to Produce HIV-1 Env Trimers This example shows that a STREP-TAG® II with an extended linker allows rapid purification of HIV-1 gp140 envelope trimers.

Figure 4:
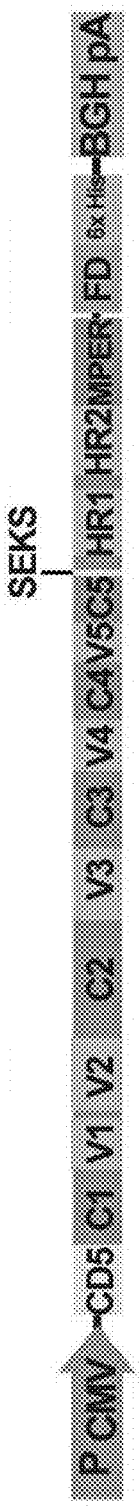
FIG. 4 is a schematic drawing of a JRFL foldon-gp140 recombinant construct showing the positions of the cleavage resistant SEKS mutation, foldon, and His-tag according to some embodiments of the present invention.

Several codon-optimized gp140 constructs from HIV-1 strains JRFL, SF162 (clade B viruses), and CONPEP (clade C) for production of Env trimers are tested. As an example, FIG. 4 is a schematic image of the JRFL foldon-gp140 recombinant construct showing the positions of the cleavage resistant SEKS mutation, foldon, and His-tag. The gp140 DNA containing gp120 and gp41 ectodomain sequences truncated at aa664 or 683 (HXB2 numbering) is cloned under the control of the CMV promoter (FIG. 4) and transfected into a variety of mammalian cell lines (293F, 293T, 293EXPI, CHO, GNTI-). With a signal peptide fused to the N-terminus, gp140 is secreted into the culture medium and the efficiency of production is quantified. Both cleavage resistant (CR) and cleavage proficient (CP) clones are tested. For CR gp140, the furin cleavage site REKR between gp120 and gp41 is mutated to SEKS and for CP gp140, it is mutated to RRRRRR and co-transfected with a second furin-containing plasmid to enhance cleavage.[52]

Of the three signal peptides tested, CD5, tPA, and Gluc, CD5 show consistently better expression. Fusing a hexa-histidine (His) tag at the C-terminus of recombinant gp140 did not affect expression, whereas an N-terminal tag shows poor expression probably because the hydrophilic tag affected cleavage of the adjacent, largely hydrophobic, signal peptide. However, the C-terminal tag bound poorly, if at all, to Ni-agarose.

Figure 5:
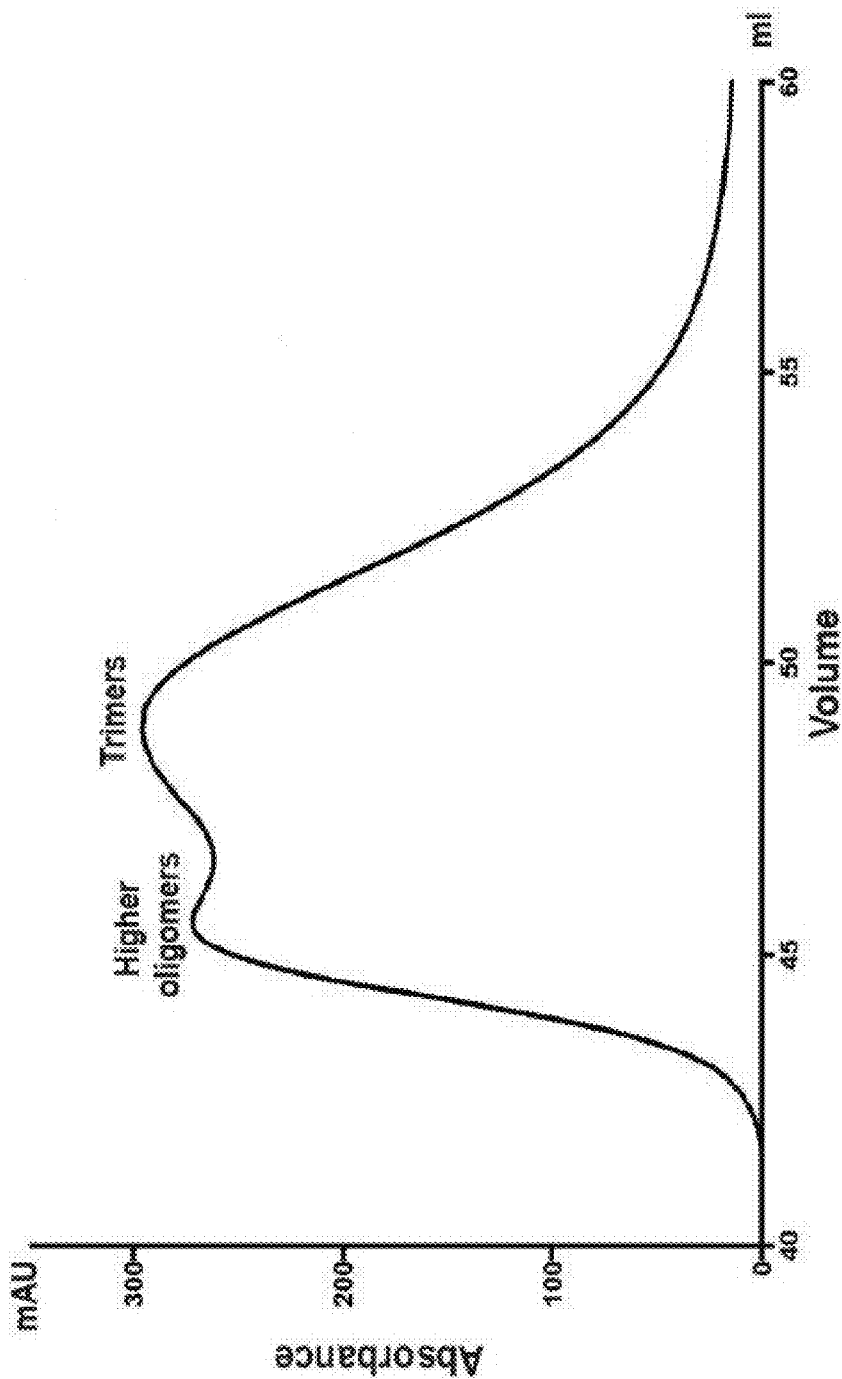
FIG. 5 is a graph of elution profile of trimers and oligomers on SEC for the purification of uncleaved JRFL gp140 foldon trimers according to some embodiments of the present invention.
Figure 6:
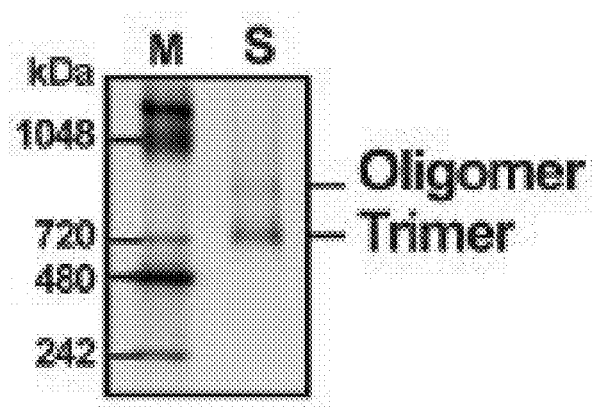
FIG. 6 is an image of native gel of starting material from HisTrap column that is loaded on SEC (lane S) according to some embodiments of the present invention.
Figure 7:
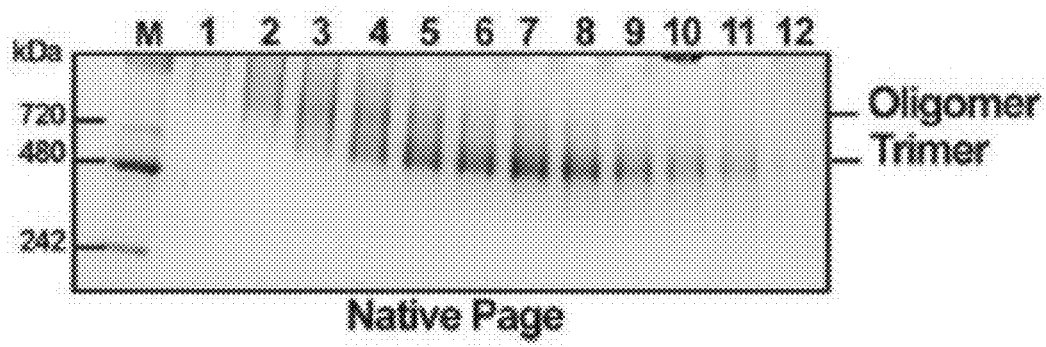
FIG. 7 is an image of native gel of the SEC fractions according to some embodiments of the present invention.

In some example, clones are also constructed by inserting the 27aa phage T4 fibritin trimerization motif (foldon)[48] which has a sequence comprising SEQ ID NO: 7 between the C-terminus of recombinant gp140 and the His-tag (e.g., JRFL, FIG. 3). As shown in FIG. 4, for CR gp140, the furin cleavage site REKR between gp120 and gp41 is mutated to SEKS. These constructions produce a mixture of trimers and higher oligomers but no protomers (monomers and dimers). These trimers bind to Ni-agarose and can be further purified by size exclusion chromatography (SEC), which resolves the oligomers, but the elution profiles overlap (FIGS. 5, 6, and 7). These results are consistent with the foldon-based trimers reported by other investigators[26,59,60] (also see Table 1 below).

FIG. 5 shows elution profile of trimers and oligomers on SEC for purification of uncleaved JRFL gp140 foldon trimers. FIG. 6 is an image of native gel of starting material from HisTrap column that is loaded on SEC (lane S). The gel is stained with Coomassie blue. Lanes "M" show MW markers. The MWs in kDa of the marker proteins are shown on the left. FIG. 7 is an image of native gel of the SEC fractions. The gels in FIG. 6 and FIG. 7 are stained with Coomassie blue. Lanes "M" show MW markers. The MWs in kDa of the marker proteins are shown on the left. Further biochemical analyses show that the protomers of these trimers are non-specifically crosslinked with disulfide bonds (see below).

Recombinants without any tag are constructed and recombinant gp140 is captured using lectin beads (*Galanthus nivalis* lectin or concanavalin A). The protein is then purified by SEC. But the yields of the trimers vary either by direct application of the culture supernatant or after 2-3× concentration by tangential flow filtration. Aggregation of some of the gp140 during lectin chromatography occurs. Furthermore, the binding potency of lectin diminishes progressively after each use.

Figure 8:
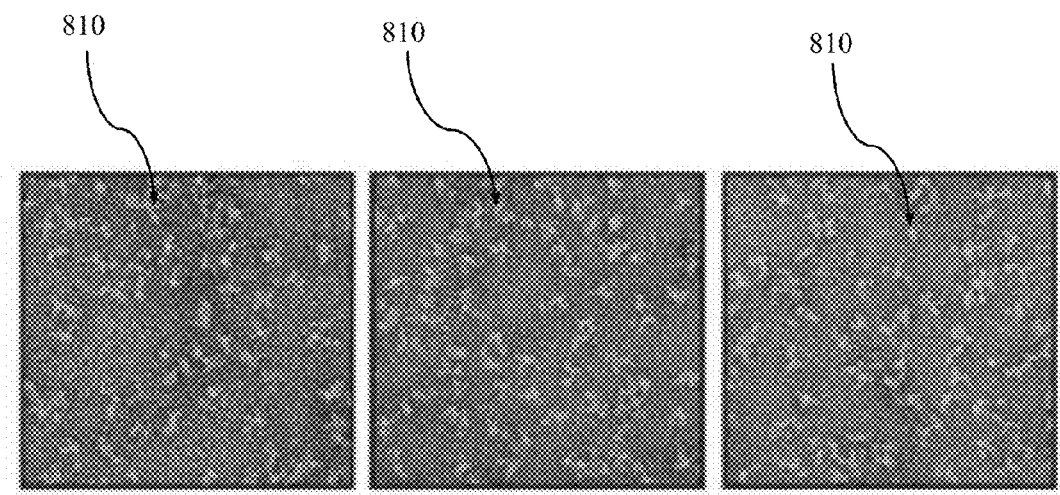
FIG. 8 is an image of negative-stain EM of the peak trimer fraction from FIG. 4 according to some embodiments of the present invention.
Figure 9:
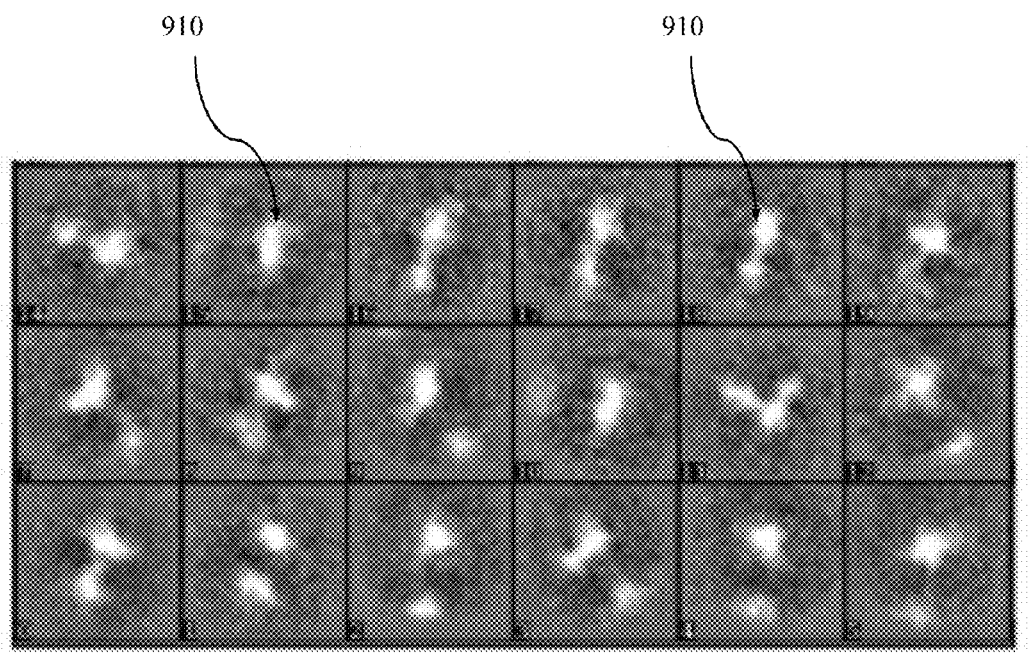
FIG. 9 is an image of 2D class averages of foldon trimers from FIG. 7 according to some embodiments of the present invention.

FIG. 8 illustrates negative-stain EM of the peak trimer fraction from FIG. 5. FIG. 9 illustrates 2D class averages of foldon trimers shown in FIG. 8. As illustrated in FIGS. 7 and 8, negative-stain EM of trimers produced by the above approaches shows heterogeneous mixtures of particles. Relatively few are classic three-blade propeller shaped, and some, for instance the JRFL foldon trimers, show variably shaped particles 810 (FIG. 8) and 910 (FIG. 9), similar to that reported by Georgiev et al,[60] even though all these preparations behave as "true" trimers by SEC and Blue native (BN) gel electrophoresis (See Table 1).

In Table 1, various approaches used for the purification of HIV-1 trimers are compared. As shown in table 1, the approach of fusing an eight amino acid STREP-TAG® II tag through a >20 amino acid linker to the C-terminus of gp140 provides several useful features and is broadly applicable to generate trimers from potentially any HIV-1 virus.

TABLE 1

Comparison of various approaches used for the purification of HIV-1 trimers

| | Lectin | 2G12 | Foldon | STREP-TAG ® II |
|---|---|---|---|---|
| Ligand | *Galanthus nivalis* lectin attached to solid matrix | BnAb 2G12 coupled to Sepharose 4B (Sanders 2013) | Ni (or a heavy metal such as Co) attached to solid matrix | Modified streptavidin, referred to as STREP-TACTIN ®, attached to solid matrix |
| gp140 | Wild-type | Wild-type | The 27-amino acid trimerization motif, referred to as foldon or fibritin, followed by His-tag fused to the C-terminus of gp140 | The 8-amino acid STREP-TAG ® II peptide with a >20 amino acid linker fused to the C-terminus of gp140 |
| Specificity | Low, broad All molecules (not only proteins) containing mannose captured | High, narrow Requires epitope containing α1-2-linked mannoses in appropriate structural context; envelope proteins of variant HIV viruses lacking the epitope may not be captured; these must be mutated to create a binding site for 2G12 BnAb (Murin 2014 & Sanders 2013) | High Binds to hexa- or octa-histidine tag at the C-terminus | High Binds to STREP-TAG ® II at the C-terminus |
| Elution | Strong reagent (1M mannose) | Strong reagent (3M MgCl$_2$) | Strong reagent (200-400 mM imidazole) | Mild reagent (2.5 mM d-Desthiobiotin) |
| Purity | Low to Medium In addition to gp120, gp140 protomers (monomers and dimers) and trimers, mannose-containing non-target molecules will also be captured and co-purified; the purified sample therefore may contain significant amounts of these contaminants | High Captures only the envelope protein molecules containing the 2G12 epitope; these include gp120, gp140 protomers (monomers and dimers) and trimers | Low to Medium In addition to His-tag containing gp140 protomers (monomers and dimers) and trimers, Ni can non-specifically bind to non-target contaminating proteins | High Because of high specificity to STREP-TACTIN ®, only the STREP-TAG ® containing gp140 protomers (monomers and dimers) and trimers will be captured |
| End specificity | No Does not discriminate between the full-length gp140 molecules and gp120 or truncated products of gp140; the latter would remain as contaminants | No Does not discriminate between the full-length gp140 molecules and gp120 or truncated products of gp140; the latter would remain as contaminants | Yes Since binding requires the C-terminally fused tag, the purified sample essentially contains full-length gp140 molecules; gp120 and most of the truncated products will be excluded by the column | Yes Since binding requires the C-terminally fused tag, the purified sample essentially contains full-length gp140 molecules; gp120 and most of the truncated products will be excluded by the column |
| Quality of trimers | Medium The co-purified contaminants might affect the quality of the trimers. | High High percentage (>90%) of three-blade propeller shaped trimers demonstrated with cleaved BG505 gp140 | Low Primarily used for production of uncleaved trimers; trimers are irregular shaped and non-specifically crosslinked | High High percentage (>90%) of three-blade propeller shaped trimers demonstrated with cleaved JRFL gp140 |
| Stripping | No Contaminants nonspecifically bound to the column cannot be completely stripped off using conventional reagents such as | No Stripping with urea or NaOH will likely disrupt epitope binding; washing with 3M MgCl$_2$ might remove some of the contaminants | Yes Can be stripped with EDTA, urea, or NaOH multiple times | Yes Can be stripped with NaOH multiple times |

TABLE 1-continued

Comparison of various approaches used for the purification of HIV-1 trimers

| | Lectin | 2G12 | Foldon | STREP-TAG ® II |
|---|---|---|---|---|
| | urea or NaOH as these will denature the lectin; washing with high salt buffers can strip some of the contaminants | | | |
| Re-use | Limited Can be re-used but the binding capacity significantly reduced after each use | Not known | High Can be stripped and re-used multiple times without significantly losing the binding capacity. | High Can be stripped and re-used multiple times without significantly losing the binding capacity. |
| Capacity | Low to Medium 3 mg ligand/ml | Not known | High 50 mg ligand/ml | High 9 mg ligand/ml |
| Cost | Medium $130 for 2 ml or 6 mg of *Galanthus nivalis* lectin GNL (Vector Laboratories) Cost would be higher than the amount shown because independent columns may need to be used for purification of different gp140 proteins to avoid cross-contamination | High $565 for 1 mg of 2G12 Ab (Polymun Scientific) Cost might be higher because, i) all the 2G12 may not be coupled to Sepharose in an active form; and ii) independent columns may need to be used for purification of different gp140 proteins to avoid cross-contamination | Low $23 for 2 ml of Ni— NTA Agarose (Qiagen) Since complete stripping can be done, the same column can be re-used for purification of a different gp140 protein; cross contamination, if any, would be minimal | Low $166 for 2 ml of STREP-TACTIN ® Superflow Plus (Qiagen) Since complete stripping can be done, the same column can be re-used for purification of a different gp140 protein; cross contamination, if any, would be minimal |

Example 3

Extended STREP-TAG® II Allows Efficient Isolation of gp140

This example illustrates an approach that allows selective capture of gp140 directly from the culture medium and is desirable for the production of trimers. Previous attempts to achieve this by fusing gp140 with a tag such as the His-tag have failed. It is hypothesized that these failures stemmed from the possibility that the tag, when attached to the base of the gp140 structure, is probably occluded, a problem further compounded by the presence of glycan shield, with up to 12 glycans attached to the C-terminal heptad repeat (HR)-2 helices. If the hypothesis is correct, extending the tag away from the base should make it more accessible for binding. This reasoning is supported by an example showing that an insertion of a 27aa foldon sequence comprising SEQ ID NO: 7 between the C-terminus of gp140 and the His-tag allows efficient binding to Ni-agarose.

A series of 36 recombinant clones are constructed as shown in FIG. 2 by fusing the gp140 C-terminus to STREP-TAG® II and octa-histidine tag with various linkers in the middle. STREP-TAG® II is an 8aa peptide (WSHPQFEK) comprising SEQ ID NO: 1 that binds to modified streptavidin, namely STREP-TACTIN®, at μM affinity and stringent specificity. Yet, the complex can be dissociated with desthiobiotin, a mild condition. Clade B JRFL gp140 is chosen as a template to evaluate this approach, but it is also constructed, in parallel, clade A BG505 gp140 clones for comparison. Three "SOSIP" mutations and five "stabilizing" mutations are introduced to stabilize JRFL trimers.[49, 50] The three "SOSIP" mutations include A501C, T605C, and I559P mutations. The A501C and T605C mutations create an intra-protomer disulfide bond between gp120 and gp41, and the I559P mutation in the heptad repeats HR1 helix strengthens inter-subunit (gp41) interactions. The five "stabilizing" mutations in or near HR1 (I535M, Q543L, S553N, K567Q, and R588G) strengthen gp120 and gp41 interactions at the interface.[49,50,51]

Figures 10, 11:
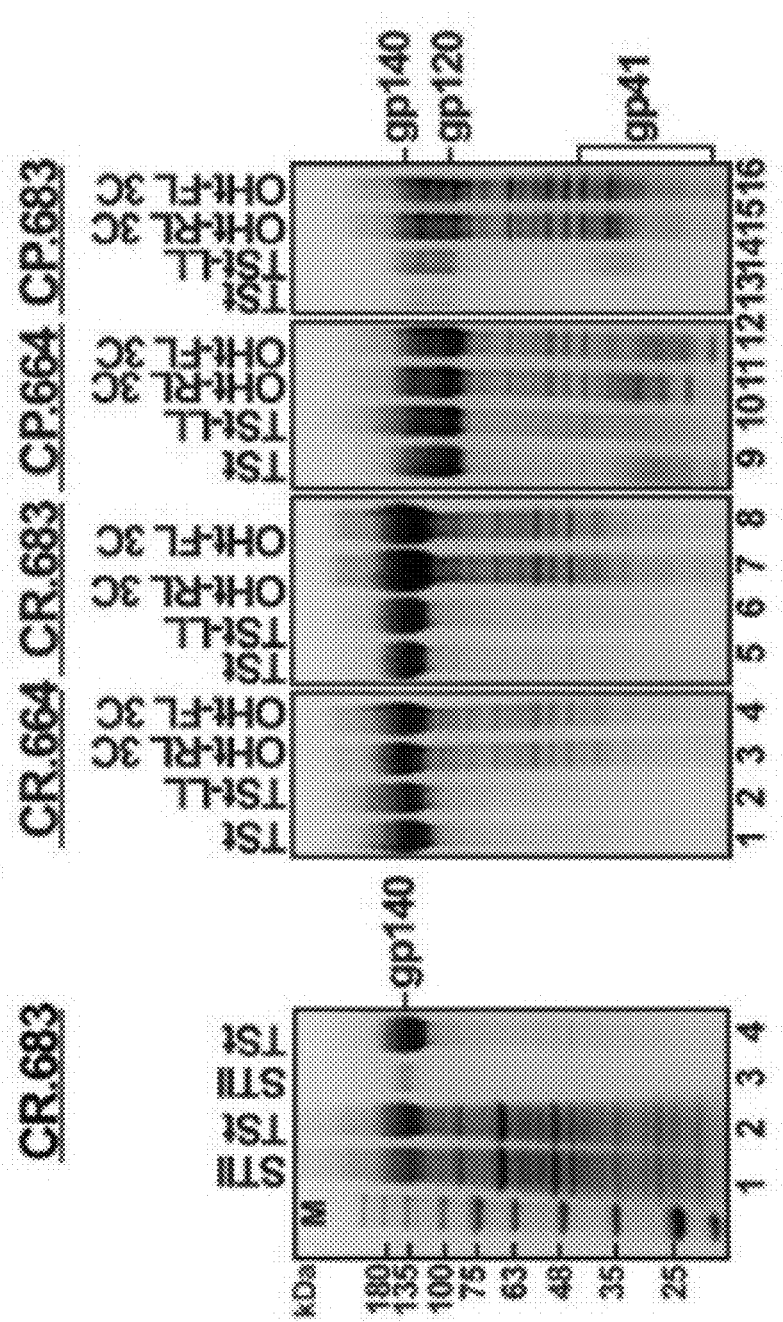
FIG. 10 is an image of reducing SDS polyacrylamide gel showing protein patterns of the samples as indicated at the top according to one embodiment of the present invention.
FIG. 11 is a set of images of reducing SDS polyacrylamide gels showing protein patterns of the samples as indicated at the top according to one embodiment of the present invention.

FIGS. 10 and 11 are images of reducing SDS polyacrylamide gels showing protein patterns of the samples as indicated at the top according to one embodiment of the present invention. Gels are stained with Coomassie blue. Lanes labeled as "M" show MW markers. The MWs in kDa of the marker proteins are shown on the left. The data demonstrate that the STREP-TAG® II approach is highly effective to capture gp140 from the culture medium. Strep-Tagged gp140 with a short $(Ala)_3$ (or GlySerGlySer) linker bound poorly to STREP-TACTIN® (FIG. 10, lane 3), whereas the Twin STREP-TAG® containing 23aa linker is efficiently captured (FIG. 10, lane 4), even though both clones expressed gp140 at similar levels (FIG. 10, lanes 1 and 2).

As shown in FIG. 11, bound gp140 can be specifically dissociated with 2.5 mM desthiobiotin and the eluted protein is ~95% pure (e.g., FIG. 11, lanes 1 and 2). An HRV 3C protease cleavage site engineered between the gp140 C-terminus and the linker is not cleaved, consistent with the hypothesis that a large protease molecule would encounter clashes with the protomer base. Various forms of gp140 can be efficiently captured: uncleaved (FIG. 11, lanes 1-8) or cleaved (FIG. 11, lanes 9-16); truncated at aa664 (FIG. 11, lanes 1-4 and 9-12) or aa683 (FIG. 11, lanes 5-8 and 13-16); tagged with octa-His with a flexible linker (FIG. 11, lanes 4, 8, 12, 16) or a rigid linker (FIG. 11, lanes 3, 7, 11, 15).

Figure 12:
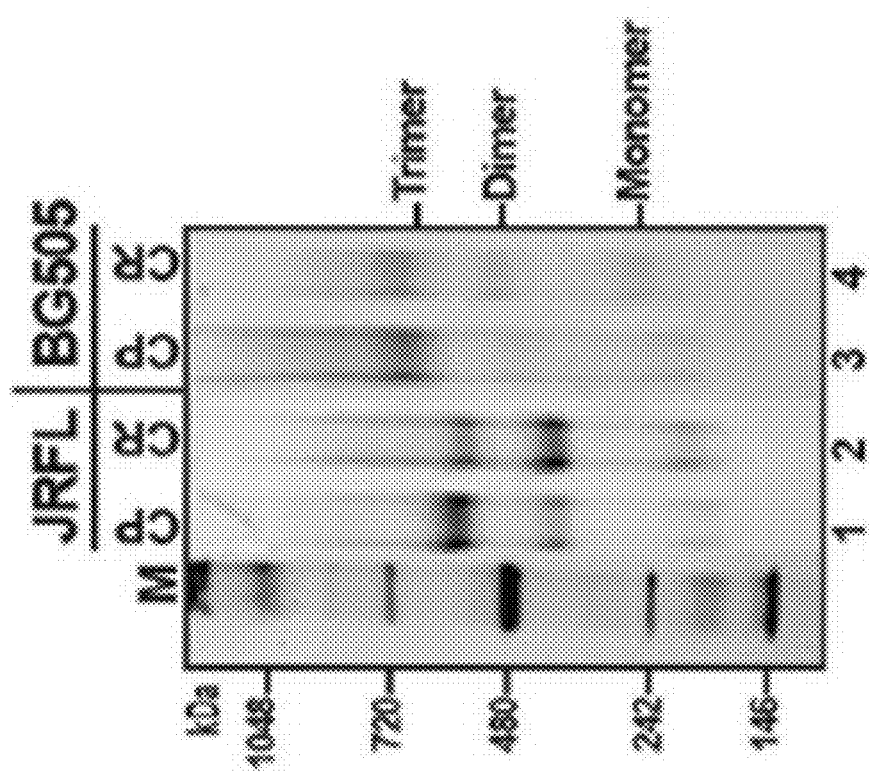
FIG. 12 is an image of Blue native (BN) gel of STREP-TACTIN® purified gp140 samples according to one embodiment of the present invention.

Various forms of gp140 developed from clade A(BG505), clade B (JRFL), and clade A-E viruses can also be captured. FIG. 12 is an image of Blue native (BN) gel of STREP-TACTIN® purified gp140 samples. Lanes labeled as "M" show MW markers. The MWs in kDa of the marker proteins are shown on the left. Gels are stained with Coomassie blue. As shown in FIG. 12, cleaved and uncleaved gp140 from clade A and clade B viruses can be captured. In addition, trimers from SF162 (clade B) and 40007 (clade CRF01 A-E) viruses are also purified. Furthermore, unlike the capture methods employing lectin or 2G12 BnAb, the approach disclosed herein specifically captures full-length gp140 molecules and excludes gp120 and the truncated molecules that are often generated by nonspecific proteases (see Table 1).

Example 4

Strep-Tagged JRFL gp140 Produces Abundant Amounts of Trimers

Figures 13, 14:
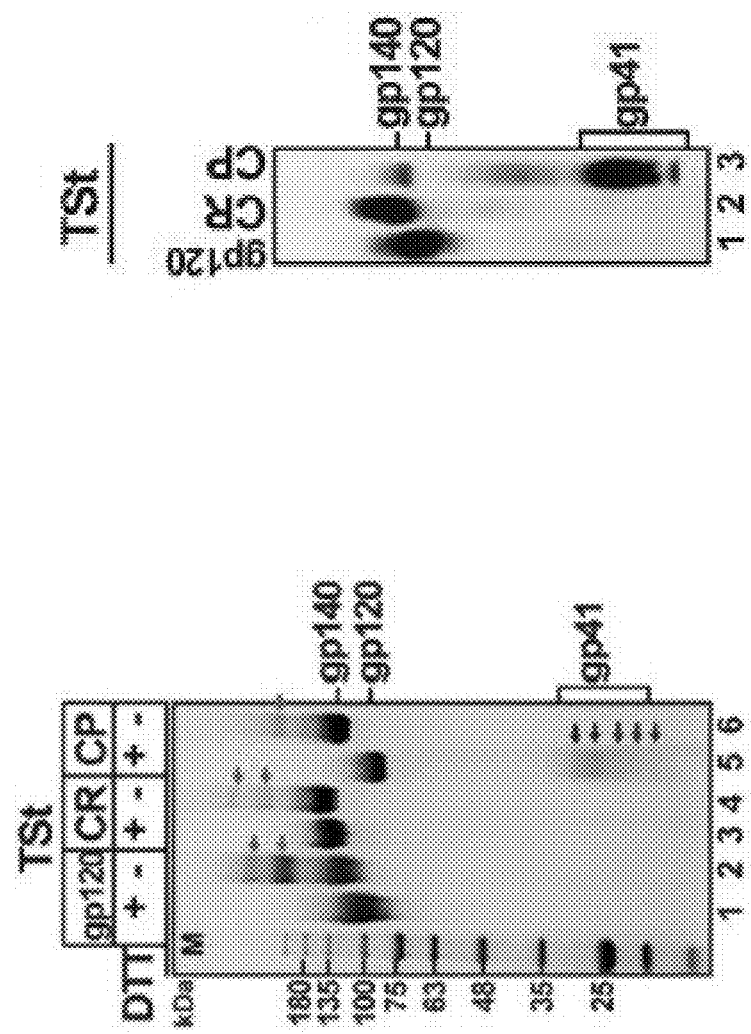
FIG. 13 is an image of SDS gel of samples under reducing (+DTT) or non-reducing (−DTT) conditions according to one embodiment of the present invention.
FIG. 14 is an image of Western blot using STREP-TAG® II specific mAb according to one embodiment of the present invention.

CP and CR gp140 produce cleaved and uncleaved trimers, respectively. FIG. 13 is an image of SDS gel of samples under reducing (+DTT) or non-reducing (−DTT) conditions. Short arrows show oligomers of gp120 or gp140 formed by nonspecific disulfide crosslinking. Long arrows correspond to the ladder of gp41 ectodomain bands glycosylated to varying extents. Lanes labeled as "M" show MW markers. The MWs in kDa of the marker proteins are shown on the left. Gels are stained with Coomassie blue. As shown in FIG. 13, cleavage by furin is nearly complete in CP gp140 (FIG. 13, lane 5) whereas little or no cleavage is evident in CR gp140 (FIG. 13, lane 3). The cleaved gp120 and gp41 subunits are covalently associated through the SOS disulfide bond as evident from the appearance of a single 140 kDa band under non-reducing conditions (FIG. 13, lane 6) and two bands (gp120 and gp41) under reducing conditions (FIG. 13, lane 5). However, a ladder of five gp41 bands is also seen (arrows in lane 5, FIG. 13), probably corresponding to glycosylation of 0 to 4 N-linked glycosylation sites (see below). The CR gp140, on the other hand, shows a single 140-kDa band under both reducing and non-reducing conditions (FIG. 13, lanes 3 and 4). The lack of cleavage of CR gp140 is further confirmed by Western blotting using a highly sensitive STREP-TAG® specific mAb as shown in FIG. 14.

Whether the CR gp140 also forms the SOS bond cannot be determined. Varying levels of higher oligomers are also seen in all preparations (including gp120), probably due to nonspecific disulfide crosslinking of the protomers under non-reducing conditions, but much less so with the cleaved gp140 (arrows in lanes 2, 4, and 6 of FIG. 13). About two-thirds of the Strep-Tagged JRFL CP664-gp140 assemble into trimers (FIG. 12, lane 1), whereas CR664-gp140 produces more dimers than trimers (FIG. 12, lane 2). Similar patterns are also seen with Strep-Tagged BG505 gp140. However BG505 produces higher levels of uncleaved trimers (FIG. 12, lane 4, compare with lane 2), and the trimer bands are more diffused than JRFL indicating more extensive glycosylation as also evidenced by slightly higher MW of these bands (FIG. 12, lanes 3 and 4, compare with lanes 1 and 2).

Example 5

Truncation of Cleaved gp140 Beyond aa664 Results in Poor gp140 Production

This example illustrates that truncations beyond aa664 produce little or no gp140 trimers. (FIGS. 15, 16, 17, 18 and 19). In this example, a rapid strategy to optimize various parameters for maximal trimer production, using any HIV-1 Env sequence, is developed.

Figure 15:
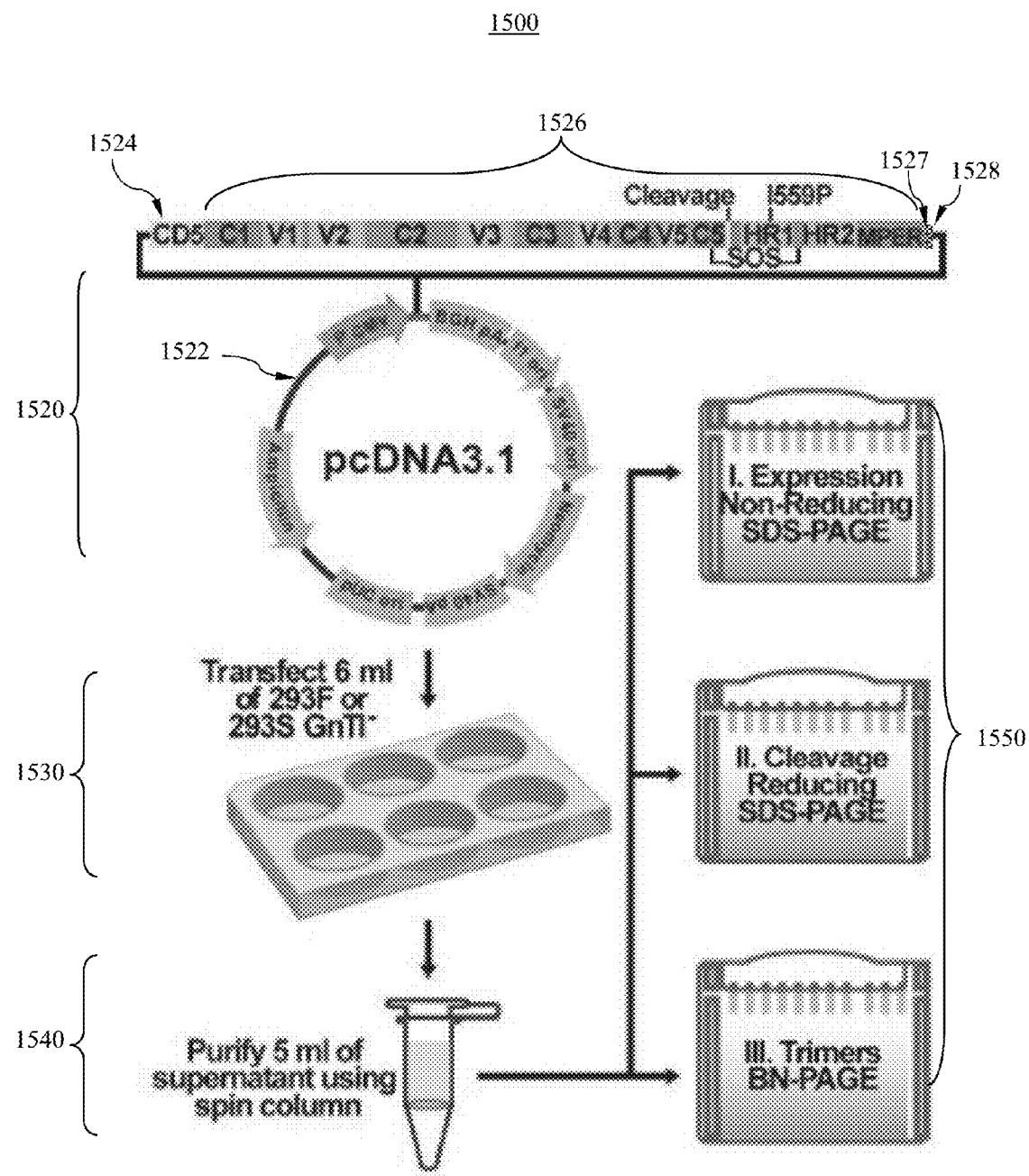
FIG. 15 is a schematic illustration of an example of screening strategy to optimize recombinant gp140 production according to one embodiment of the present invention according to one embodiment of the present invention.
Figures 18, 19:
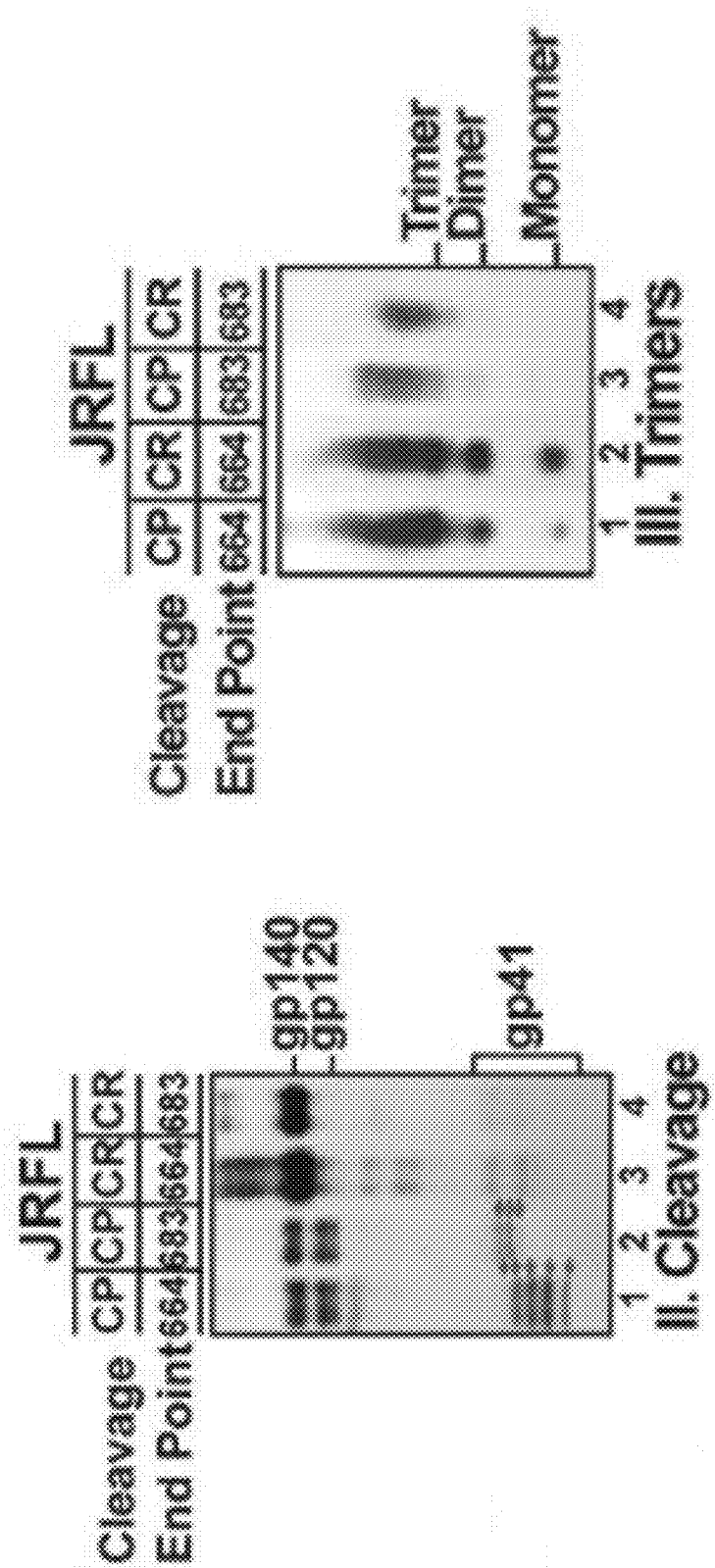
FIG. 18 is an image showing reducing SDS gel of uncleaved and cleaved gp140 proteins truncated at aa664 and aa683 according to one embodiment of the present invention.
FIG. 19 is an image showing BN gel of STREP-TACTIN® purified gp140 samples according to one embodiment of the present invention.

FIG. 15 shows an exemplary screening strategy 1500 to optimize recombinant various parameters for maximal trimer production, using any HIV-1 Env sequence. More than 40 different Strep-Tagged gp140 clones 1522 are constructed at step 1520. Each clone 1522 encompasses an expression cassette to express human CD5 secretion signal peptide 1524 fused Strep-Tagged gp140 protein 1526. Human CD5 secretion signal peptide 1524 is fused at N-terminus of Strep-Tagged gp140 protein 1526. Linker 1527 and STREP-TAG® II 1528 are located at C-terminus of Strep-Tagged gp140 protein 1526. Each clone is transfected into a small volume (6 ml) of cells at step 1530. At step 1550, the efficiency of gp140 expression (FIG. 16) and the efficiency of cleavage (FIG. 17) are analyzed by directly testing the culture medium. In addition, the secreted gp140 is captured by STREP-TACTIN® beads and further probed for cleavage and gp41 glycosylation (FIG. 18) and trimer formation (FIG. 19). Different parameters tested include: point of truncation, importance of SOSIP mutations and cleavage, production in 293F or GnTI⁻ cells (GnTI⁻ cells lack N-acetylglucosaminetransferase 1 and cannot introduce complex glycosylations), and clade B (JRFL) or A (BG505) gp140 (an N-glycosylation site is introduced in BG505 at aa332 to make it equivalent to JRFL gp140).[61] Results are shown in FIGS. 16, 17, 18 and 19.

Figure 17:
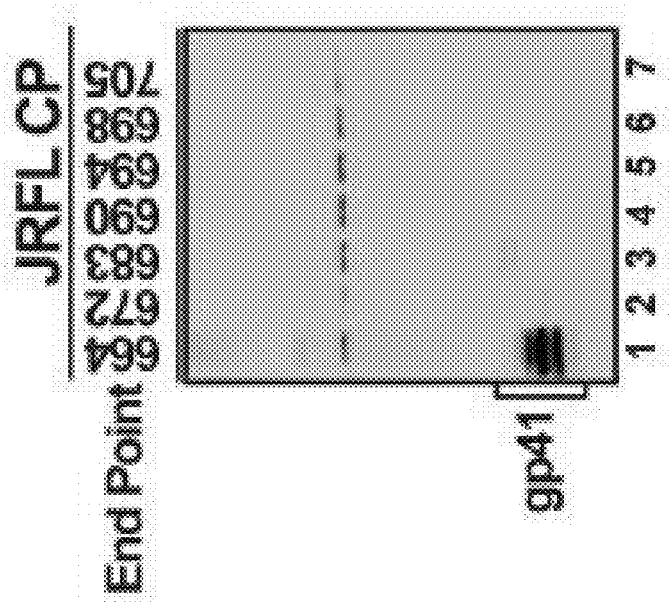
FIG. 17 is an image showing reducing SDS gel comparing the production of gp140 recombinants truncated at various amino acid positions at the C-terminus according to one embodiment of the present invention.
Figure 16:
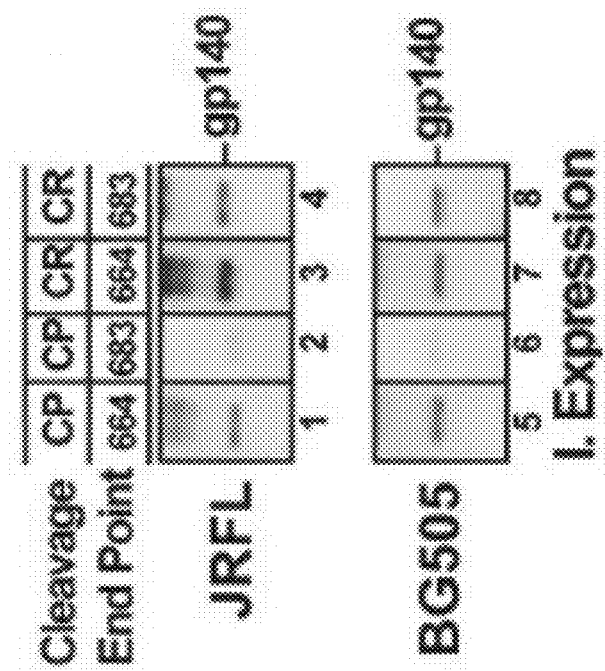
FIG. 16 is a set of images of non-reducing SDS gel comparing the production of uncleaved and cleaved gp140 in the culture medium for amino acid truncations at aa664 and aa683 according to one embodiment of the present invention.

FIGS. 16, 17, 8, and 19 illustrate that truncations beyond aa664 produce little or no gp140 trimers. FIG. 16 is an image of a non-reducing SDS gel comparing the production of uncleaved and cleaved gp140 in the culture medium for aa truncations at aa664 and aa683. FIG. 17 is an image showing reducing SDS gel comparing the production of gp140 recombinants truncated at various aa positions at the C-terminus. End point numbers correspond to the aa at the end of the C-terminus. The gp140 is captured by Strep-Tactin beads and further probed for cleavage and gp41 glycosylation (FIG. 18) and trimer formation (FIG. 19). Approximately the same amount of gp140 is loaded in each lane to compare the aa664 and aa683 proteins. FIG. 18 is an image showing reducing SDS gel of uncleaved and cleaved gp140 proteins truncated at aa664 and aa683. Arrows in darker shade and lighter shade correspond to differentially glycosylated gp41 ectodomain bands of gp140 proteins truncated at aa664 and aa683, respectively. FIG. 19 is an image showing BN gel of STREP-TACTIN® purified gp140 samples. FIGS. 16, 18, and 19 are Western blots using mouse anti-gp140 polyclonal antibody. FIG. 17 is a Western blot using STREP-TAG® II specific mAb. Data shown are for GnTI⁻ produced JRFL gp140.

Similar patterns are observed with both JRFL and BG505 gp140s expressed in 293F or GnTI⁻ cells. SOSIP mutations prove essential as without them most of the protein aggregate and cannot be captured by STREP-TACTIN®. Unexpectedly, however, cleaved gp140 truncated beyond aa664 produce lower amounts of gp140 in the culture medium (FIGS. 16 and 17). The aa672 and aa683 constructs produce 3-5 times lower amount whereas further truncation results in near complete loss of gp140 production. This result is not due to poor cleavage because 683-gp140 is efficiently cleaved producing, as expected, slightly larger gp41 ladder bands (FIG. 18, lane 2, compare with lane 1). In contrast, production of uncleaved 683-gp140 is not significantly affected. Unlike the cleaved 683-gp140 which is expressed at lower levels (FIG. 16, lanes 2 and 6; FIG. 10, compare lanes 9-12 with lanes 13-16), the expression of uncleaved 683-gp140 is nearly as high as 664 (FIG. 16, lanes 3 and 7 vs 4 and 8). Finally, the aa683 protein shows a tendency to aggregate, as shown by its appearance largely as a high molecular weight (MW) smear in the BN gel (FIG. 19, lane 3).

The above results suggest that cleavage triggers a conformational change in the MPER, which may lead to exposure of some of the hydrophobic residues leading to aggregation. This hypothesis is consistent with the previous reports by Klasse et al., and Ringe et al.,[26] which shows that the cleaved aa681 (from KNH1144) and aa683 (from BG505) gp140 proteins form micelles at the MPER, presumably through interaction of the exposed hydrophobic residues of MPER with the lipid components.

Example 6

Cleavage is Essential for Production of Authentic HIV-1 Trimers

This example illustrates that cleavage is essential for production of authentic HIV-1 trimers. FIGS. 20, 21, 22, 23, 24, 25, 26, 27, 28, 29, 30, 31, 32, 33, 34, 35, 36, 37, 38, 39, 40, 41 and 42 are images illustrating the purification of cleaved and uncleaved JRFL gp140 trimers.

Figures 20, 21:
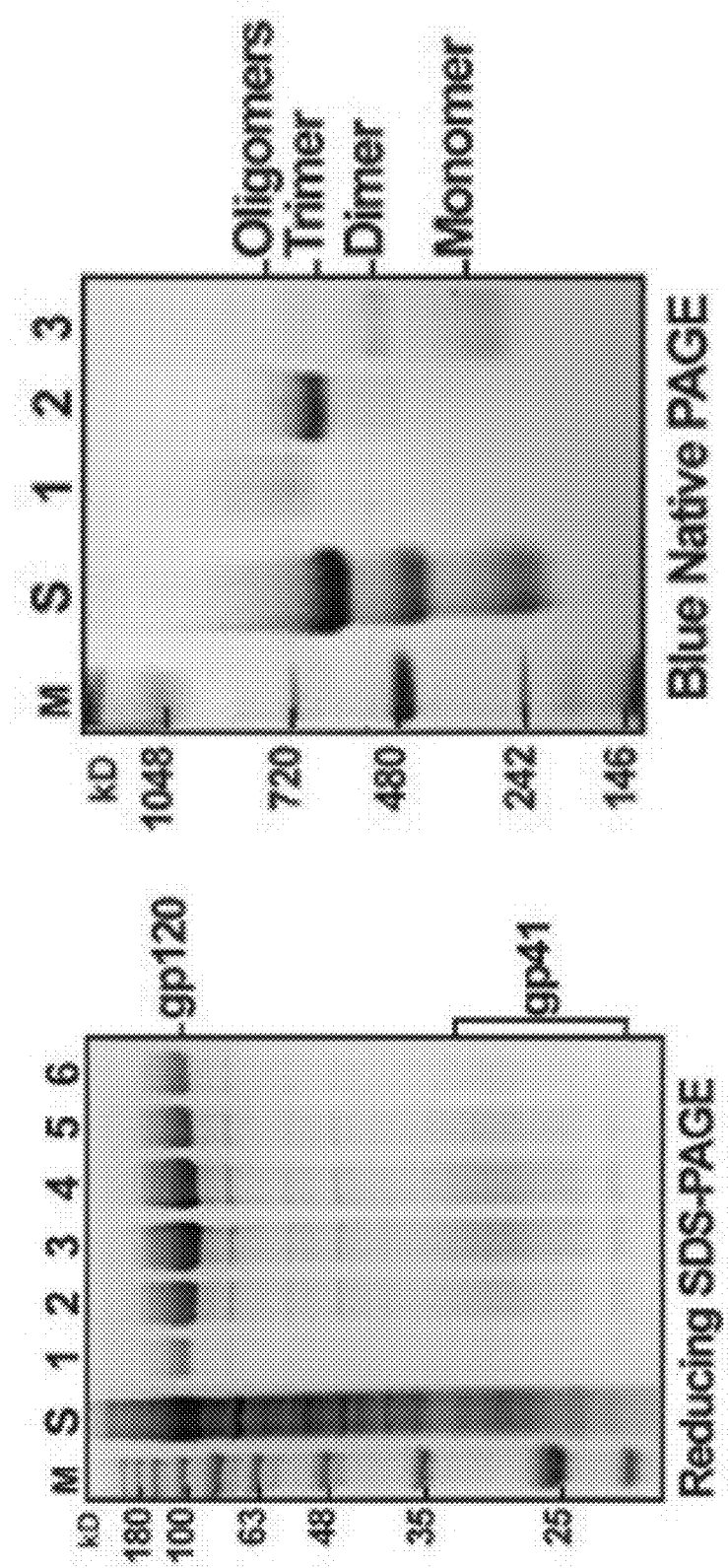
FIG. 20 is an image of reducing SDS gel of various gp140 samples showing single-step purification of Strep-Tagged gp140 from the culture supernatant by STREP-TACTIN® column according to one embodiment of the present invention according to one embodiment of the present invention.
FIG. 21 is an image showing BN gel of STREP-TACTIN® purified gp140 that is loaded on SEC (lane S) and three major fractions eluted from SEC (lanes 1-3 corresponding to the pooled peaks 1-3 shown in FIG. 21) according to one embodiment of the present invention.
Figure 22:
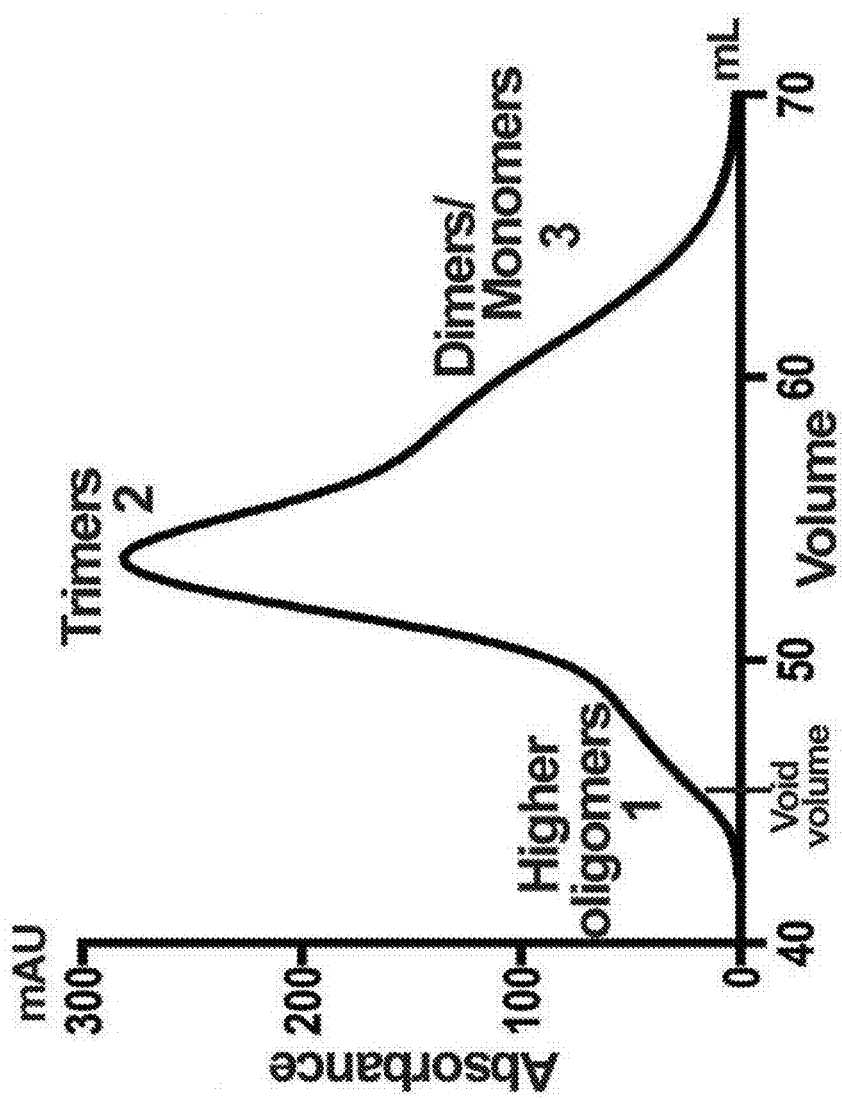
FIG. 22 is an image showing a typical elution profile of gp140 oligomers from Superdex 200 size exclusion column (SEC) according to one embodiment of the present invention according to one embodiment of the present invention.
Figure 23:
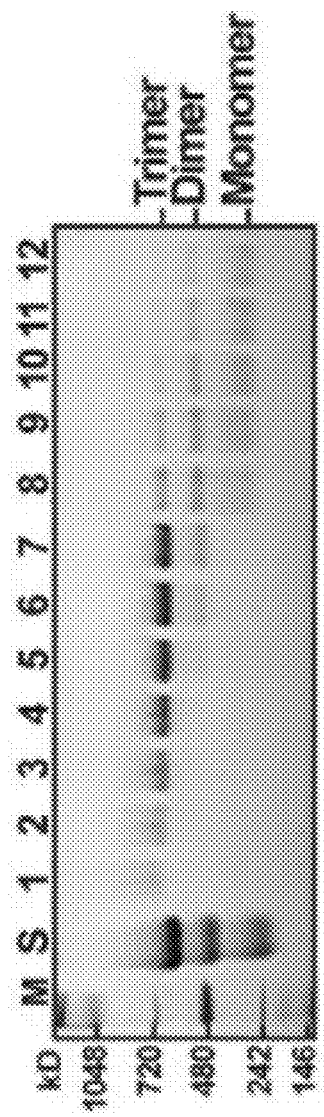
FIG. 23 is an image of BN gel showing purification of cleaved trimers expressed in 293F cells according to one embodiment of the present invention.
Figure 24:
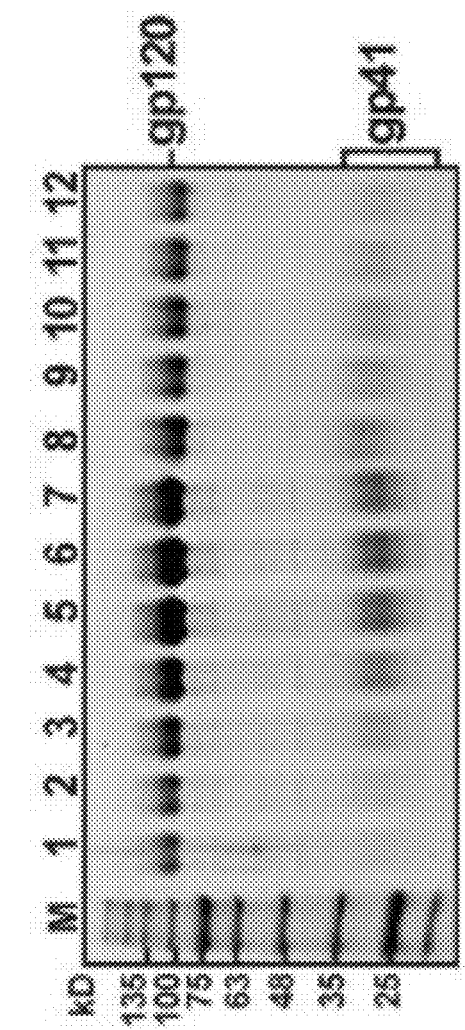
FIG. 24 is an image of reducing SDS gel of fractions showing purification of cleaved trimers expressed in 293F cells according to one embodiment of the present invention.

FIGS. 20, 21 and 22 are images showing single-step purification of Strep-Tagged gp140 from the culture supernatant by STREP-TACTIN® column. FIG. 20 is an image of reducing SDS gel of various gp140 samples: Lane S is culture supernatant; Lanes 1-6 are fractions eluted from STREP-TACTIN® column with 2.5 mM desthiobiotin. FIG. 21 is an image showing BN gel of STREP-TACTIN® purified gp140 that is loaded on SEC (lane S) and three major fractions eluted from SEC (lanes 1-3 corresponding to the pooled peaks 1-3 shown in FIG. 21). FIG. 22 is an image showing typical elution profile of gp140 oligomers from Superdex 200 size exclusion column (SEC).

As shown in FIG. 20, STREP-TACTIN® purified gp140 is ~95% pure, but it contains a mixture of trimers and protomers, as well as some high molecular weight (MW) species (FIG. 21, lane S). SEC separates these into three major fractions (FIG. 22): (i) high MW fraction that elutes immediately after the void volume and migrates as a diffused band on BN gel (FIG. 21, lane 1); (ii) trimers, which elutes as a relatively sharp peak and migrates as a compact band on BN gel (FIG. 21, lane 2); and (iii) two overlapping peaks of protomer dimers and monomers (FIG. 21, lane 3).

To determine which of the trimers are authentic; cleaved or uncleaved, 293F-produced (complex glycans) or GnTI⁻-produced (high mannose, no complex glycans), trimers are expressed on a large scale (1-4 liters) and purified by STREP-TACTIN® capture and SEC. The yields of gp140 are as follows: 293F CR-~20 mg/L; CP-~12 mg/L; GnTI⁻ CR-~3 mg/L; CP-~1 mg/L. Each SEC fraction is then analyzed by SDS-PAGE under reducing conditions to assess purity and cleavage, BN-PAGE to assess oligomeric state, negative EM to assess the shape of the trimer, and antigenicity to assess conformation (see below).

Figures 25, 26, 27:
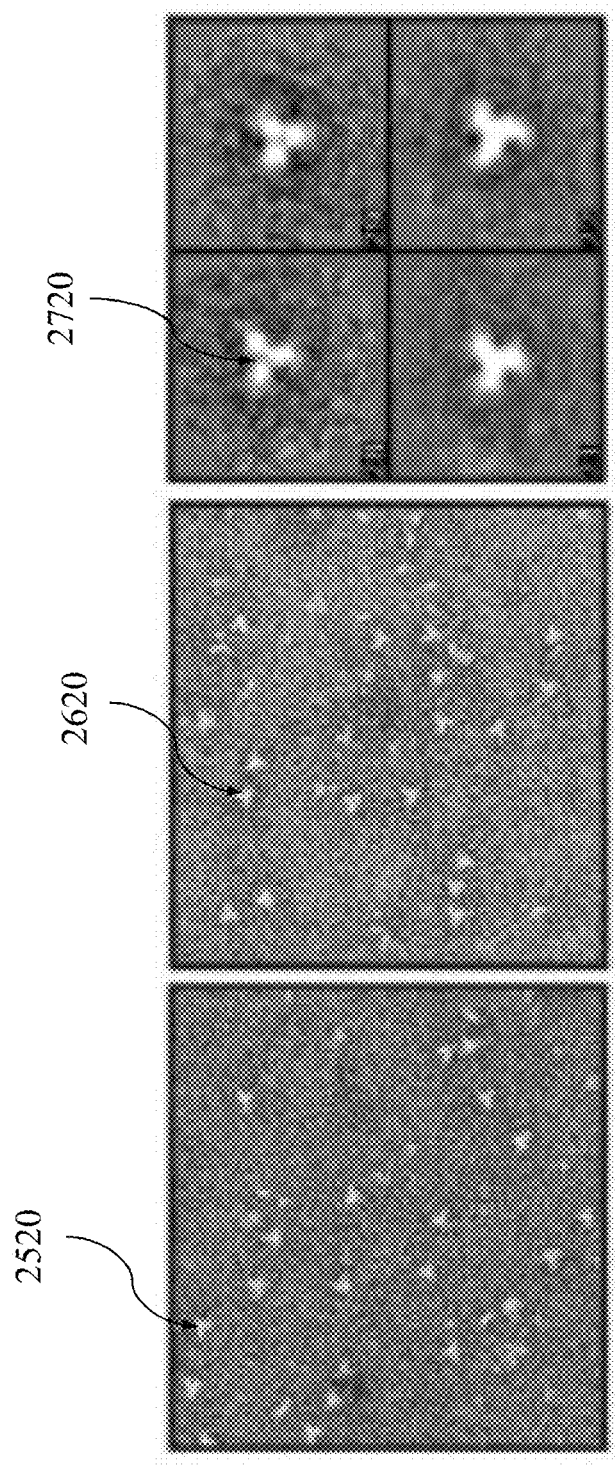
FIG. 25 is an image of negative-stain EM of the peak SEC fraction of purification of cleaved trimers expressed in 293F cells according to one embodiment of the present invention.
FIG. 26 is an image of negative-stain EM of the peak SEC fraction purification of cleaved trimers expressed in 293F cells according to one embodiment of the present invention.
FIG. 27 is an image of reference-free 2D class averages of cleaved trimers expressed in 293F cells according to one embodiment of the present invention.
Figure 28:
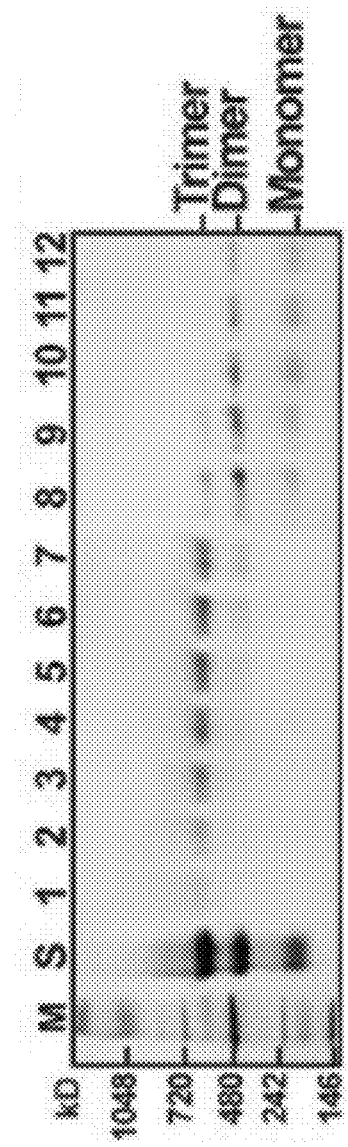
FIG. 28 is an image of BN gel showing purification of cleaved trimers expressed in GnTI⁻ cells according to one embodiment of the present invention.
Figure 29:
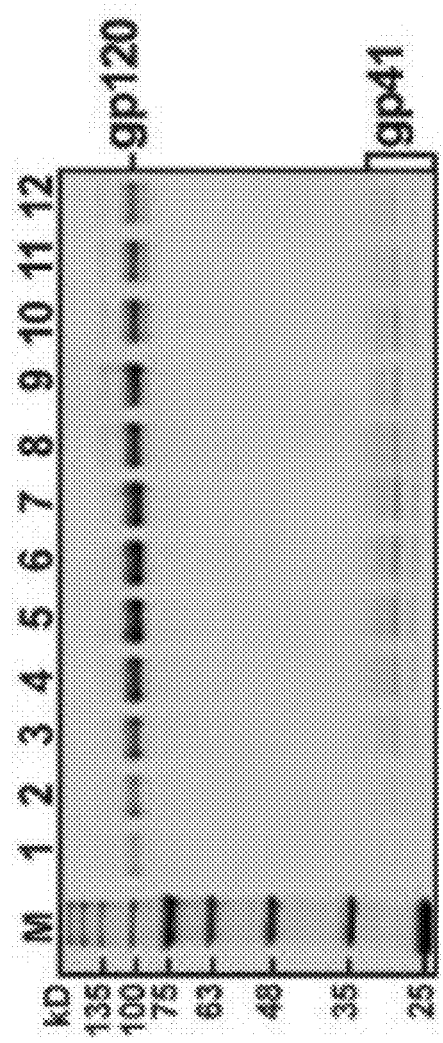
FIG. 29 is an image of reducing SDS gel of fractions showing purification of cleaved trimers expressed in GnTI⁻ cells according to one embodiment of the present invention.
Figures 30, 31, 32:
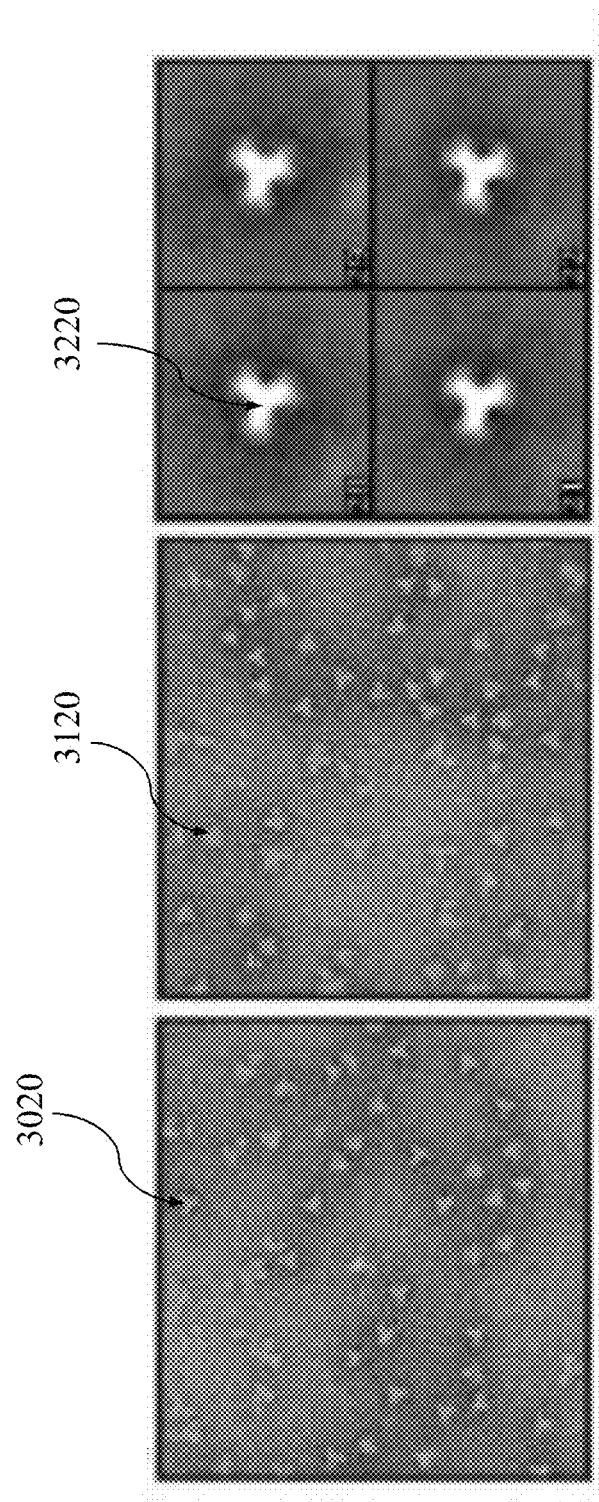
FIG. 30 is an image of negative-stain EM of the peak SEC fraction of purification of cleaved trimers expressed in GnTI⁻ cells according to one embodiment of the present invention.
FIG. 31 is an image of negative-stain EM of the peak SEC fraction of purification of cleaved trimers expressed in GnTI⁻ cells according to one embodiment of the present invention.
FIG. 32 is an image of reference-free 2D class averages of purified cleaved trimers expressed in GNTI⁻ cells according to one embodiment of the present invention.

FIGS. 23, 24, 25, 26 and 27 are images showing the purification of cleaved trimers expressed in 293F cells. FIGS. 28, 29, 30, 31 and 32 are images showing the purification of cleaved trimers expressed in GNTI⁻ cells. FIGS. 33, 34, 35, 36 and 37 are images showing the purification of uncleaved trimers expressed in 293F cells. FIGS. 38, 39, 40, 41 and 42 are images showing the purification of uncleaved trimers expressed in GNTI⁻ cells. FIGS. 23, 28, 33, and 38 are images of BN-PAGE gel of the SEC fractions. FIGS. 24, 29, 34, and 39 are images of reducing SDS gel of fractions corresponding to those showing in FIGS. 23, 28, 33, and 38. Each SEC fraction is analyzed by SDS-PAGE under reducing conditions to assess purity and cleavage in FIGS. 23, 28, 33, and 38. In FIGS. 23, 24, 28, 29, 33, 34, 38, and 39, the gels are stained with Coomassie blue; lanes S represent starting material (STREP-TACTIN®-purified gp140) loaded on SEC; lanes M show MW markers; the MWs in kDa of marker proteins are shown on the left. FIGS. 25, 26, 30, 31, 35, 36, 37, 40, 41, and 42 are images of negative-stain EM of the peak SEC fractions to assess the shape of the trimers. FIGS. 27 and 32 are images of reference-free 2D class averages of trimers. Example trimers 2520, 2620, 2720, 3020, 3120, 3220, 3520, 3620, 3720, 4020, 4120, and 4220 are respectively shown in FIGS. 25, 26, 27, 30, 31, 32, 35, 36, 37, 40, 41, and 42.

Figure 33:
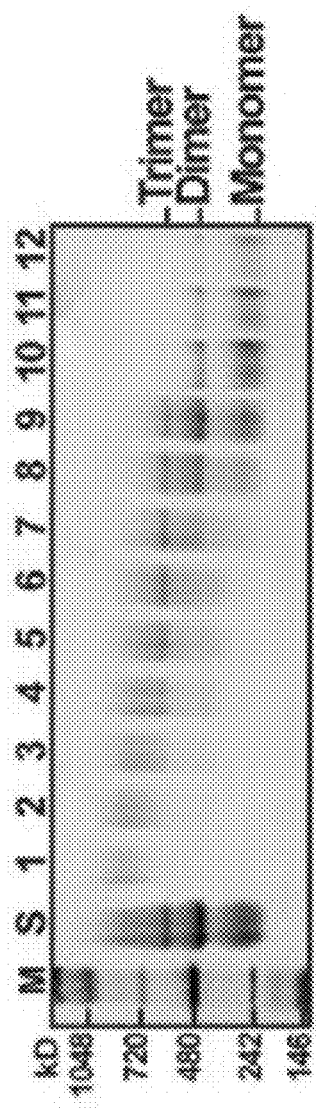
FIG. 33 is an image of BN gel showing purification of uncleaved trimers expressed in 293F cells according to one embodiment of the present invention.
Figure 34:
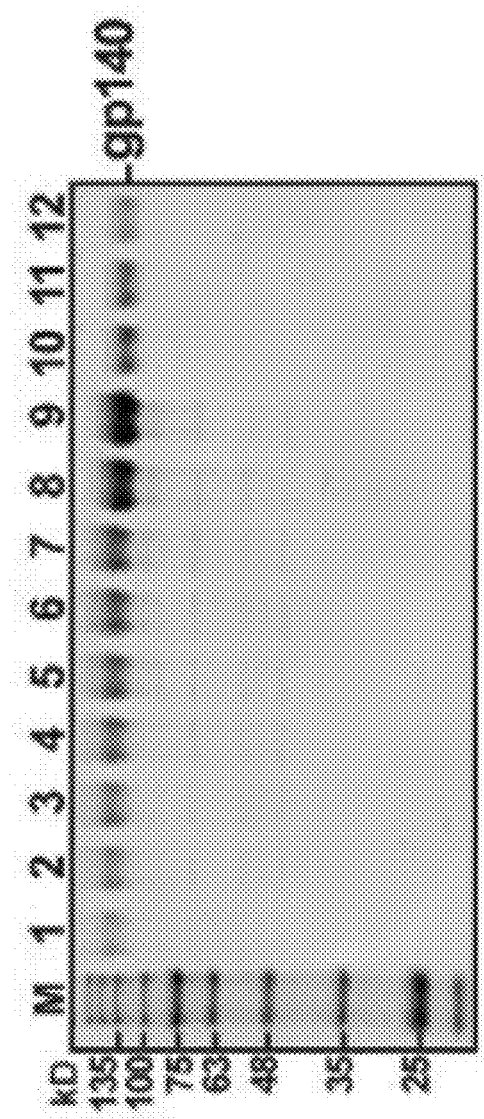
FIG. 34 is an image of reducing SDS gel of fractions showing purification of uncleaved trimers expressed in 293F cells according to one embodiment of the present invention.
Figure 38:
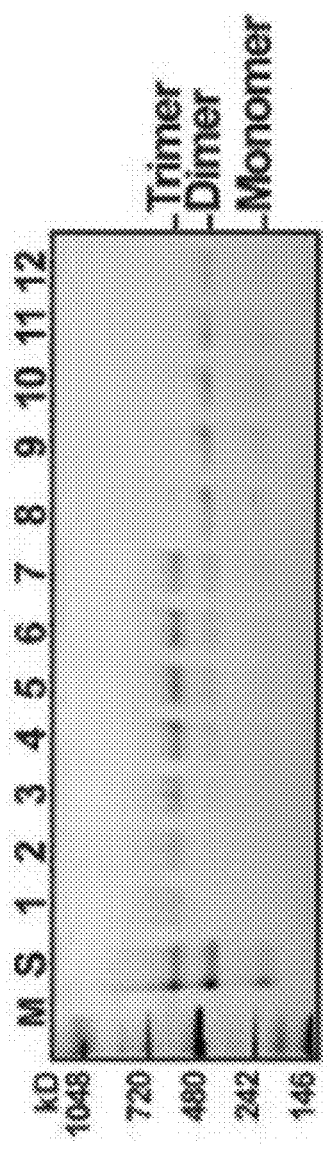
FIG. 38 is an image of BN gel showing purification of uncleaved trimers expressed in GnTI⁻ cells according to one embodiment of the present invention.
Figure 39:
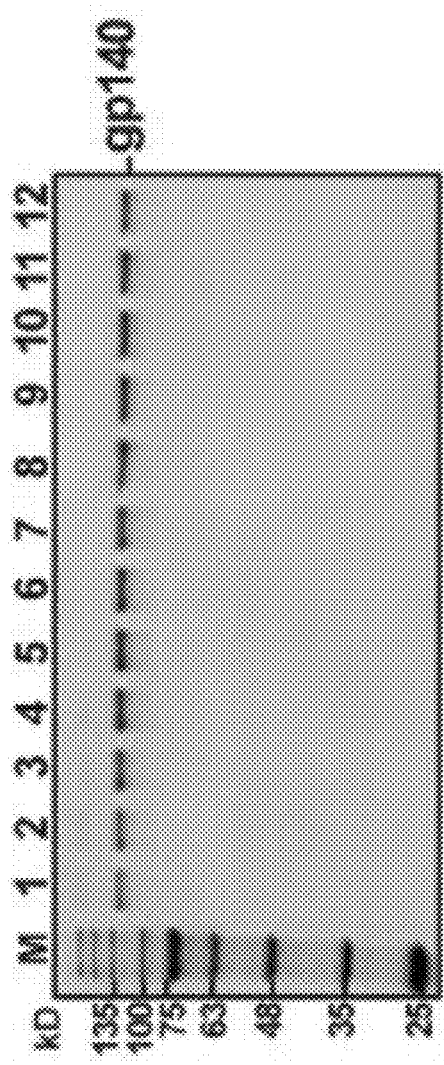
FIG. 39 is an image of reducing SDS gel of fractions showing purification of uncleaved trimers expressed in GnTI⁻ cells according to one embodiment of the present invention.

As shown in FIGS. 23, 24, 25, 26, 27, 28, 29, 30, 31, 32, 33, 34, 35, 36, 37, 38, 39, 40, 41 and 42, the trimers are purified to near homogeneity, up to 2-3 mg/L (CP trimers), as well as established the criteria for their authenticity. First, in the case of JRFL Env, the fraction of gp140 recovered as trimers is 3-5 fold greater with cleaved gp140 than with uncleaved gp140 (compare lanes S, 5-7 of FIG. 23 with FIG. 33). Second, the uncleaved trimers are of poor quality when compared to the cleaved trimers. Unlike the CP trimer fractions that show a sharp band on the BN gel (FIG. 23, lanes 3-7), the CR trimer fractions contain significant levels of diffused and high MW species (FIG. 33, lanes 3-7). The latter represents conformationally heterogeneous molecules, as is also evident from their poor reactivity with the conformation-specific BnAb PGT145 as shown in FIG. 43.

Figure 43:
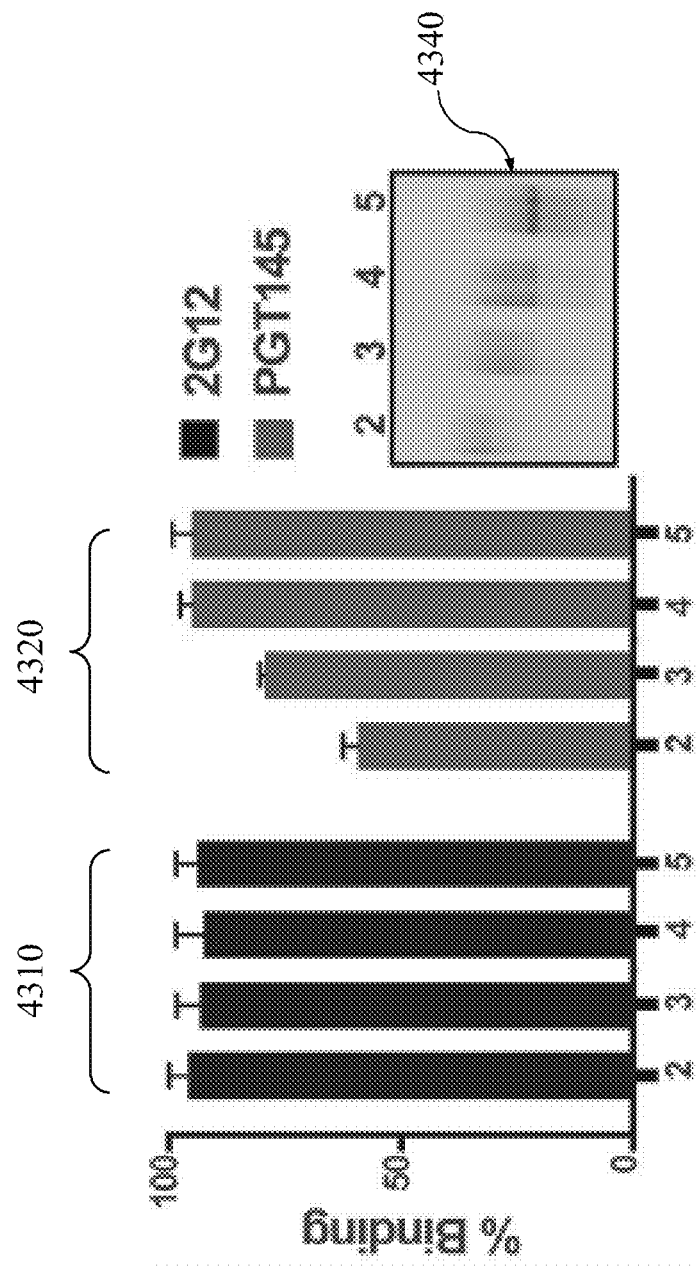
FIG. 43 is a graph illustrating conformational heterogeneity of uncleaved trimers produced in 293F cells according to one embodiment of the present invention.

FIG. 43 is an exemplary graph illustrating conformational heterogeneity of uncleaved trimers produced in 293F cells. SEC fractions 2-5 from FIG. 33 are coated on STREP-TACTIN® plates at a fixed protein concentration of 1 μg/ml and ELISAs are performed using the BnAbs 2G12 (darker shade bars 4310) or PGT145 (lighter shade bars 4320). Inset 4340 shows the Coomassie blue stained BN gel of fractions 2-5 depicting the presence of various amounts of smear in the fractions. The smear represents differential migration of conformationally heterogeneous trimers on the native gel. Note the poor reactivity of fraction 2 containing an extensive smear to the conformation-specific PGT145 BnAb when compared to fraction 5 with a lesser smear. On the other hand, the 2G12 BnAb which is not dependent on the conformation of the trimer reacted equivalently to both fractions 2 and 5. As shown in FIG. 43, the reactivity is the lowest with fractions containing the highest amount of these species.

Third, the protomers of the uncleaved trimers as well as the foldon-trimers (also uncleaved) are nonspecifically crosslinked through disulfide bonds whereas the cleaved trimers show much less crosslinking. See FIG. 44.

Figure 44:
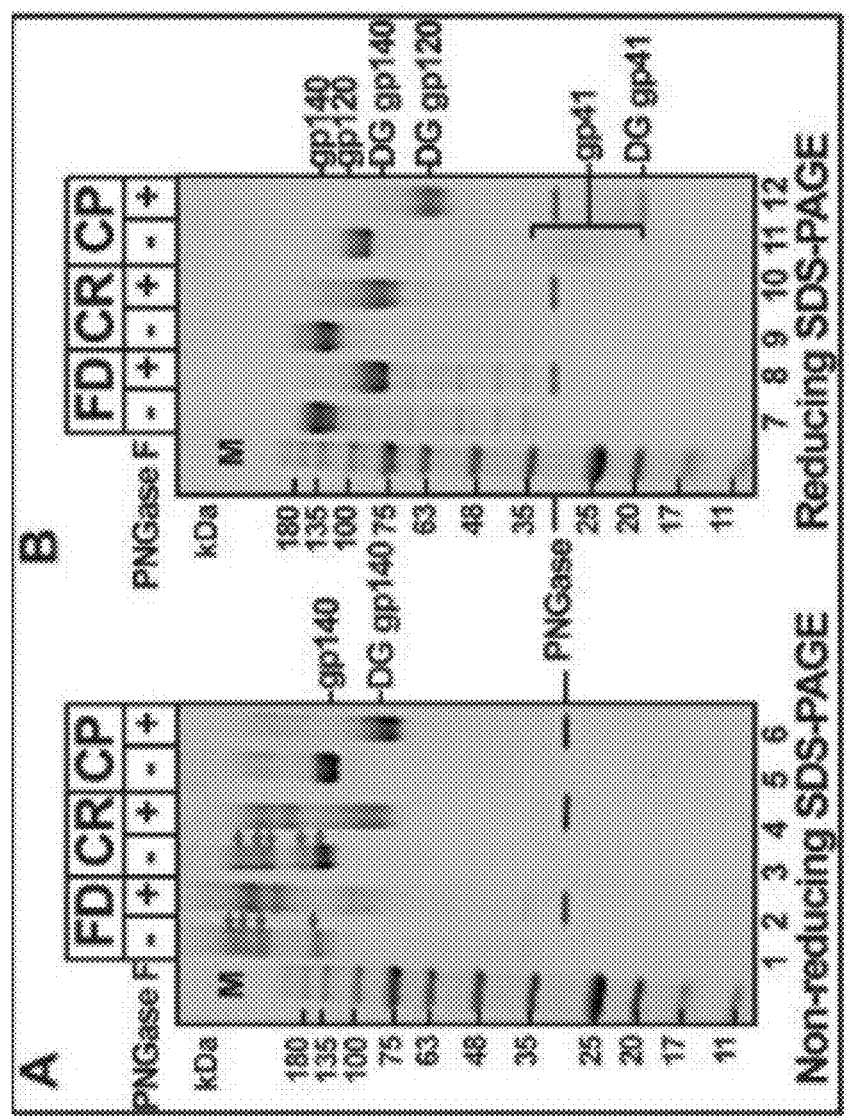
FIG. 44 is a set of gel images showing that protomers of uncleaved trimers are nonspecifically crosslinked with disulfide bonds according to one embodiment of the present invention.

FIG. 44 is a set of gel images showing that protomers of uncleaved trimers are nonspecifically crosslinked with disulfide bonds. The SEC-purified JRFL trimers; STREP-TAG® uncleaved (CR), foldon-uncleaved (FD), and STREP-TAG® cleaved trimers (CP) are electrophoresed under non-reducing (Panel A of FIG. 44) or reducing (Panel B of FIG. 44) conditions without PNGase F treatment (lanes 1, 3, 5, 7, 9, 11) or with PNGase F treatment (lanes 2, 4, 6, 8, 10, 12). A ladder of high MW bands are present in the FD uncleaved and STREP-TAG® uncleaved trimers (arrows in lanes 1 and 3), but not in the cleaved trimers (lane 5). As shown by electrophoresis under reducing conditions and treatment with PNGase F, these bands correspond to non-specific disulfide crosslinked protomers, but not to differences in glycosylation. All the high MW bands are converted to a single band under reducing conditions (lanes 7, 9), but the ladder remains after PNGase F treatment (lanes 2, 4), although the deglycosylated (DG) bands migrate faster due to the removal of glycans (when compared to lanes 1 and 3). The cleaved trimers do not show the high MW ladder bands under non-reducing conditions (lane 5) and convert to a faster-migrating DG band after PNGase F treatment (lane 6). Under reducing conditions, the cleaved trimers give rise to gp120 and a ladder of gp41 bands (lane 11), and faster-migrating DG gp120 and single DG gp41 band (lane 12) after PNGase F treatment.

Figure 45:
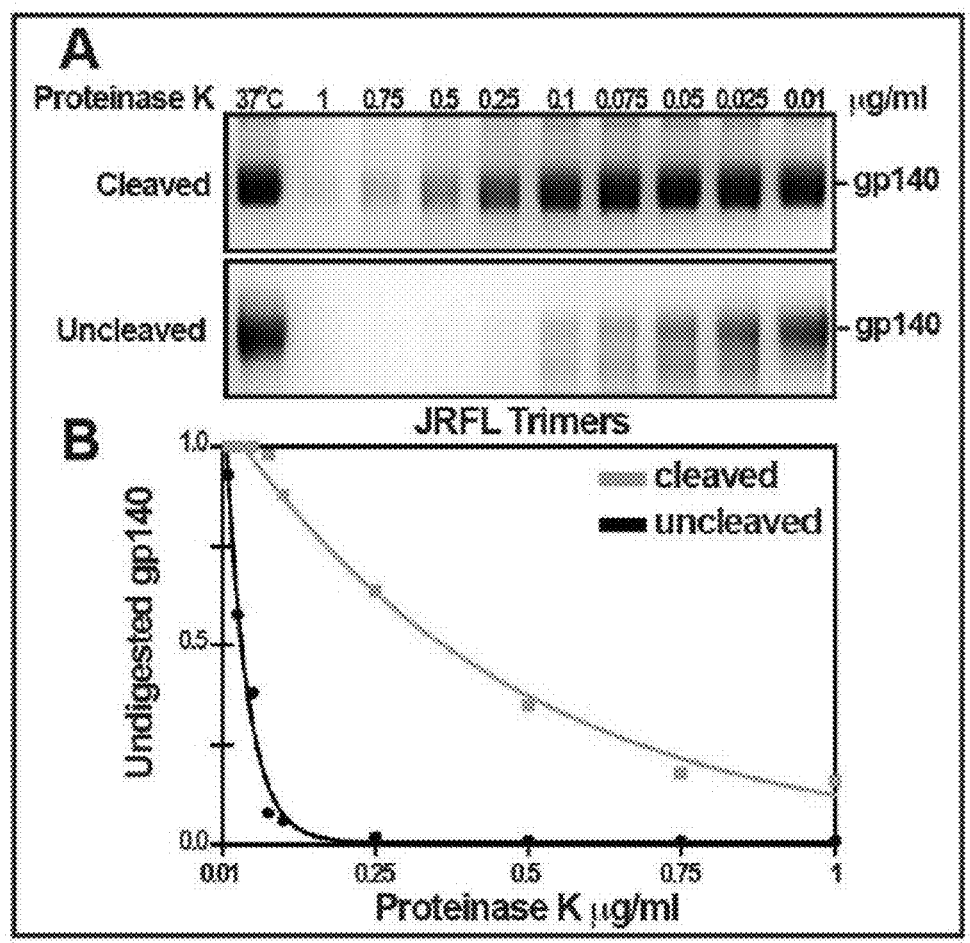
FIG. 45 is a set of gel image showing Proteinase K sensitivity of cleaved and uncleaved JRFL trimers according to one embodiment of the present invention.

Fourth, the uncleaved trimers are more susceptible to nonspecific proteolysis, as evidenced by greater proteolysis of the CR trimers by proteinase K than the CP trimers (FIG. 45). FIG. 45 is a set of image showing proteinase K sensitivity of cleaved and uncleaved JRFL trimers. Panel A of FIG. 45 shows SEC-purified trimers from 293F or GnTI– cells being treated with Proteinase K at the indicated concentrations for 1 hr at 37° C. and electrophoresed on a reducing SDS gel followed by Coomassie blue staining. The 37° C. lane corresponds to control sample incubated at 37° C. for 1 hr without Proteinase K. Note that the uncleaved trimers are more susceptible to proteolysis than the cleaved trimers, and also that the 293F trimers are more susceptible to proteolysis than the GnTI– trimers. Panel B of FIG. 45 illustrates Densitometric Quantification of the undigested gp140 bands from panel A of FIG. 45.

Finally, negative-stain EM shows that the cleaved trimers appear as three-blade propeller-shaped particles (FIGS. 25, 26, 30, and 31, reference-free 2D class averages are shown in FIGS. 27 and 32) whereas the CR fractions show fewer such particles and most are irregularly shaped (FIGS. 35, 36, 37, 40, 41, and 42).

Overall, the above results are consistent with the behavior of the uncleaved and cleaved trimers generated by the 2G12 approach (see Table 1).[26]

Example 7

Uncleaved Trimers are Hyper-Glycosylated

This example illustrates that GnTI– cells produce better quality trimers than the 293F cells although the yields are lower in GNTI– cells. (compare FIG. 23 with FIG. 28, FIG. 24 with FIG. 29, FIG. 25 with FIG. 30, FIG. 26 with FIG. 31, FIG. 27 with FIG. 32, FIG. 33 with FIG. 38, FIG. 34 with FIG. 39, FIG. 35 with FIG. 40, FIG. 36 with 41, and FIG. 37 with FIG. 42). For instance, the diffused high MW species described above are not seen in the CR trimers produced by GnTI– cells (compare FIG. 33 with FIG. 38, lanes 1-7). Negative-stain EM shows a higher number of propeller-shaped trimers in the GnTI–-produced CR trimers than in the 293-produced trimers (compare FIGS. 35, 36, and 37 with FIGS. 40, 41, and 42, respectively), which, in part, is due to heterogeneity in glycosylation. GnTI– cells predominantly add Man5GlcNAc2 which is further processed by complex glycosylation in 293F cells. Presence of STREP-TAG® II at the C-terminus of gp41 allows evaluation of glycosylation using Strep-Tag-specific mAbs.

Figure 47:
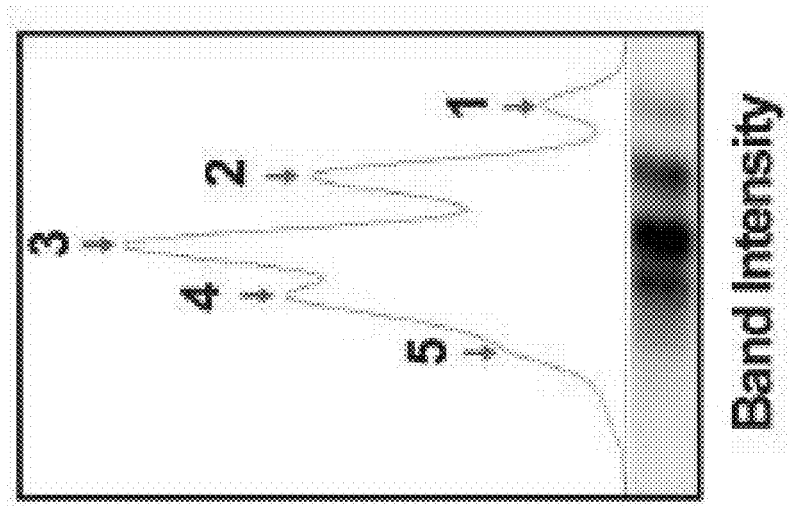
FIG. 47 is an image shows densitometric quantification of the intensity of the gp41 ladder bands shown in FIG. 46 according to one embodiment of the present invention.
Figure 46:
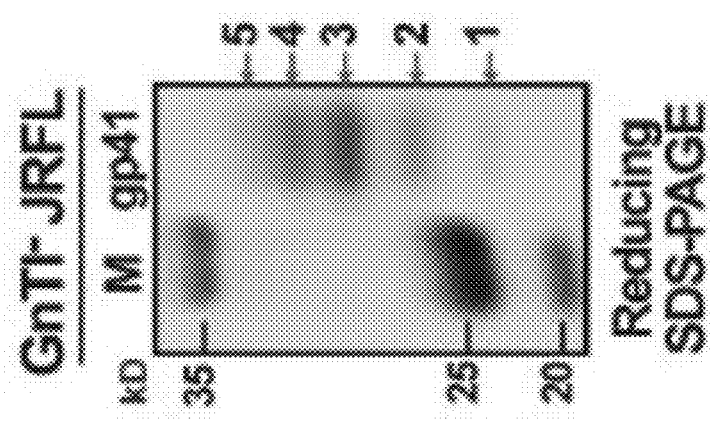
FIG. 46 is an image of reducing SDS gel showing the ladder of gp41 ectodomain bands according to one embodiment of the present invention.
Figure 48:
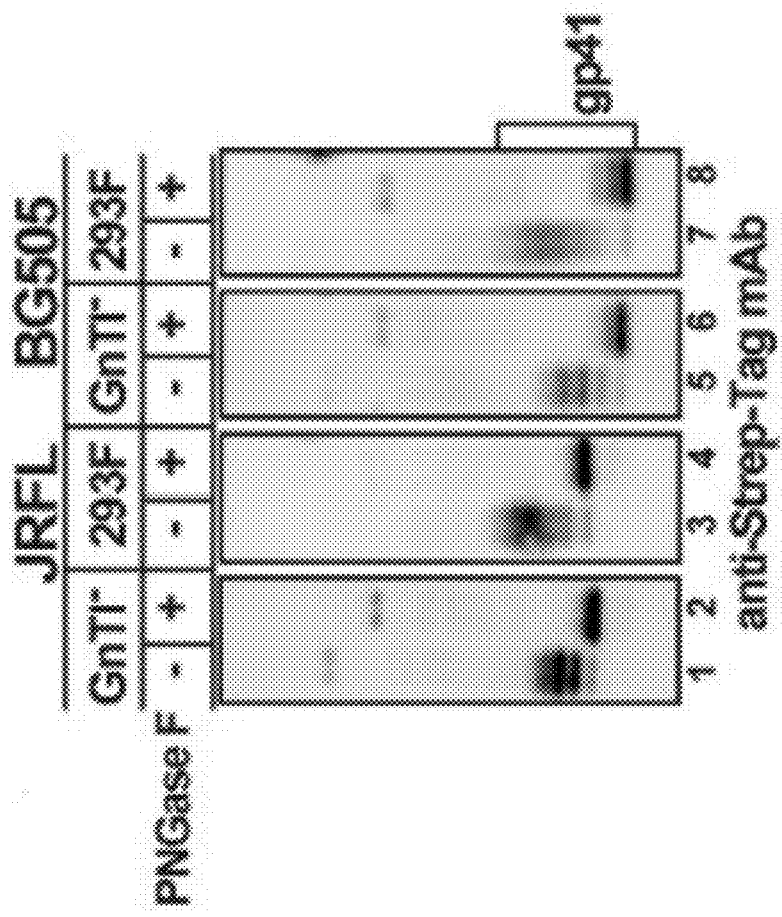
FIG. 48 is an image of a Western blot of reducing SDS gel using STREP-TAG® II specific mAb according to one embodiment of the present invention.

FIGS. 46, 47, and 48 are exemplary images showing that the uncleaved trimers produced in 293F cells are hyper-glycosylated. FIG. 46 is an image of western blot of reducing SDS gel using the STREP-TAG® mAb showing the ladder of gp41 ectodomain bands. Lanes "M" show MW markers. The MWs in kDa of marker proteins are shown on the left. The gel is stained with Coomassie blue. FIG. 47 shows densitometric quantification of the intensity of the gp41 ladder bands shown in FIG. 46. FIG. 48 is an image of a Western blot of reducing SDS gel using STREP-TAG® II specific mAb.

The presence of STREP-TAG® II at the C-terminus of gp41 allows evaluation of glycosylation status by using STREP-TAG® II specific mAbs. As shown in FIGS. 46 and 47, a ladder of five gp41 bands appears when CPgp140 trimers are electrophoresed under reducing conditions. Of these bands, band #3 shows maximum intensity (FIG. 46 and FIG. 47). Since the JRFL gp41 ectodomain contains a cluster of four predicted N-linked glycosylation sites near its C-terminus, these bands probably correspond to glycosylation of 0 to 4 sites. This is confirmed by deglycosylation with PNGase F, which converts the ladder to a single species that migrates at the same position as the lowest band in the ladder corresponding to the unglycosylated gp41 (FIG. 48, lanes 2,4,6,8). Although a similar pattern is observed in both 293F and GnTI– cells, the fully glycosylated 293F-gp41 bands are more diffused than the same from GNTI–-gp41 (FIG. 48, compare lanes 1 to 3 and 5 to 7), presumably due to complex-glycosylation. BG505 CP-gp140 shows similar banding patterns except that it appeared to undergo more extensive glycosylation. These results demonstrate "micro-heterogeneity" in gp41 glycosylation, albeit to a higher extent in 293F cells than in GnTI– cells. Heterogeneity of gp41 glycosylation was also inferred in previous reports.[62, 63]

Figure 50:
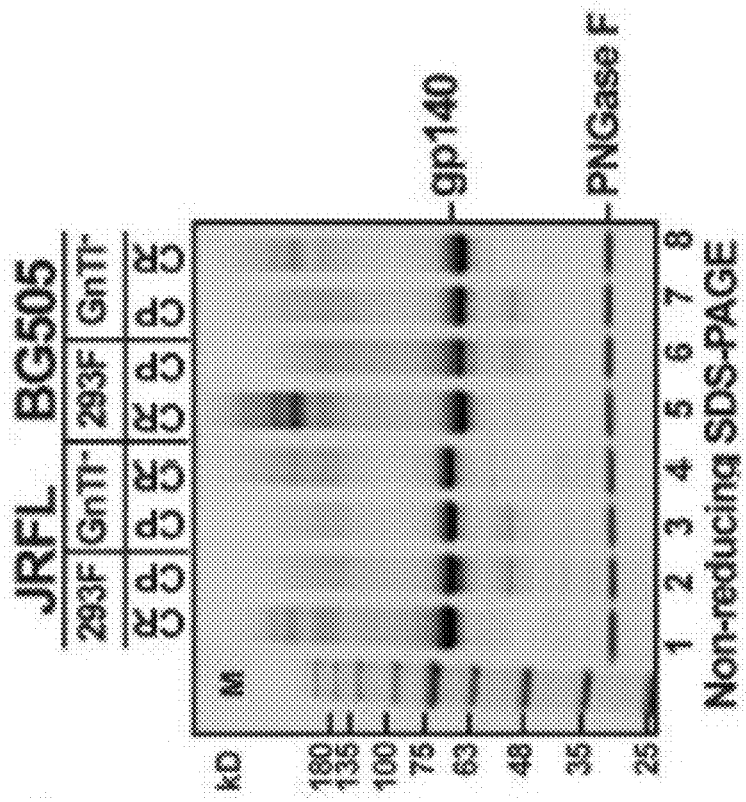
FIG. 50 is an image of Coomassie blue-stained non-reducing SDS gel of samples from FIG. 49 after treatment with PNGase F according to one embodiment of the present invention.
Figure 49:
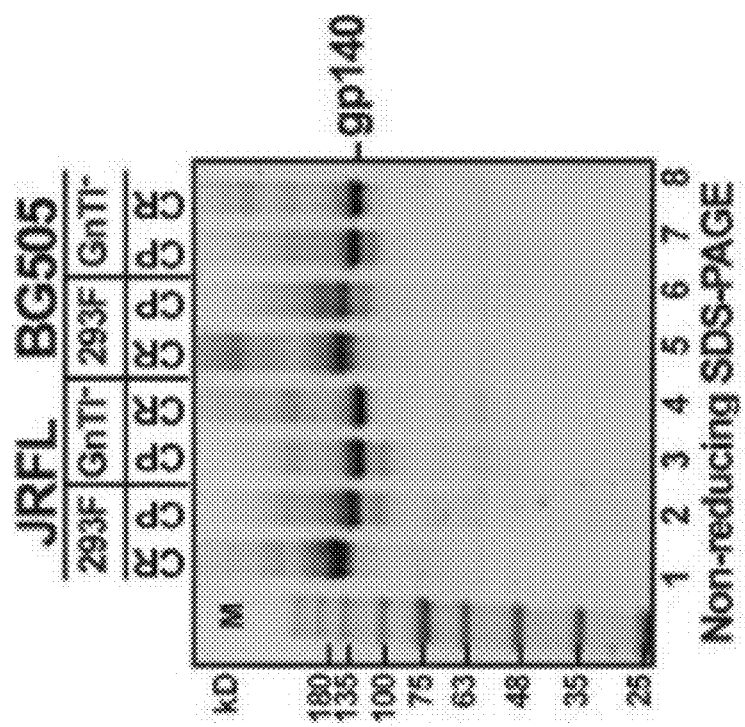
FIG. 49 is an image of Coomassie blue-stained non-reducing SDS gel of purified uncleaved (CR) and cleaved (CP) JRFL and BG505 gp140 trimers produced in 293F or GnTI⁻ cells according to one embodiment of the present invention.

The heterogeneity is even more severe with the uncleaved trimers. Indeed, the uncleaved trimers produced by 293F cells are "hyper-glycosylated". FIG. 49 is an image of Coomassie blue-stained non-reducing SDS gel of purified uncleaved (CR) and cleaved (CP) JRFL and BG505 gp140 trimers produced in 293F or GnTI– cells. FIG. 50 is an image of Coomassie blue-stained non-reducing SDS gel of samples from FIG. 49 after treatment with PNGase F. Lanes "M" show MW markers. The MWs in kDa of marker proteins are shown on the left. As shown in FIG. 49, under non-reducing conditions, both the CP gp140 and CR gp140 migrate at the same position when gp140 is produced by the GnTI– cells (FIG. 49, lanes 3 and 4). The 293F gp140 migrates slower than the GnTI– gp140 (compare lanes 1 and 3, FIG. 49), which is expected because gp140 undergoes complex glycosylations in 293F cells. Unexpectedly, however, the 293F-produced CR gp140 migrates slower than CP gp140 (FIG. 49, compare lanes 1 and 2). Upon deglycosylation with PNGase F, all gp140 bands, whether uncleaved or cleaved, produced in 293F or GnTI– cells, migrate at the same position (FIG. 50). The same pattern is also observed with the BG505 gp140 trimers tested in parallel (see BG505 lanes in FIGS. 48 and 49). These results demonstrate that the 293F uncleaved trimers are hyper-glycosylated when compared to their cleaved counterparts.

Example 8

Antigenic Signatures Discriminate Between Uncleaved and Cleaved Trimers

In this example, an ELISA platform that can differentiate the structural and conformational states of cleaved and uncleaved trimers is used.

Figure 51:
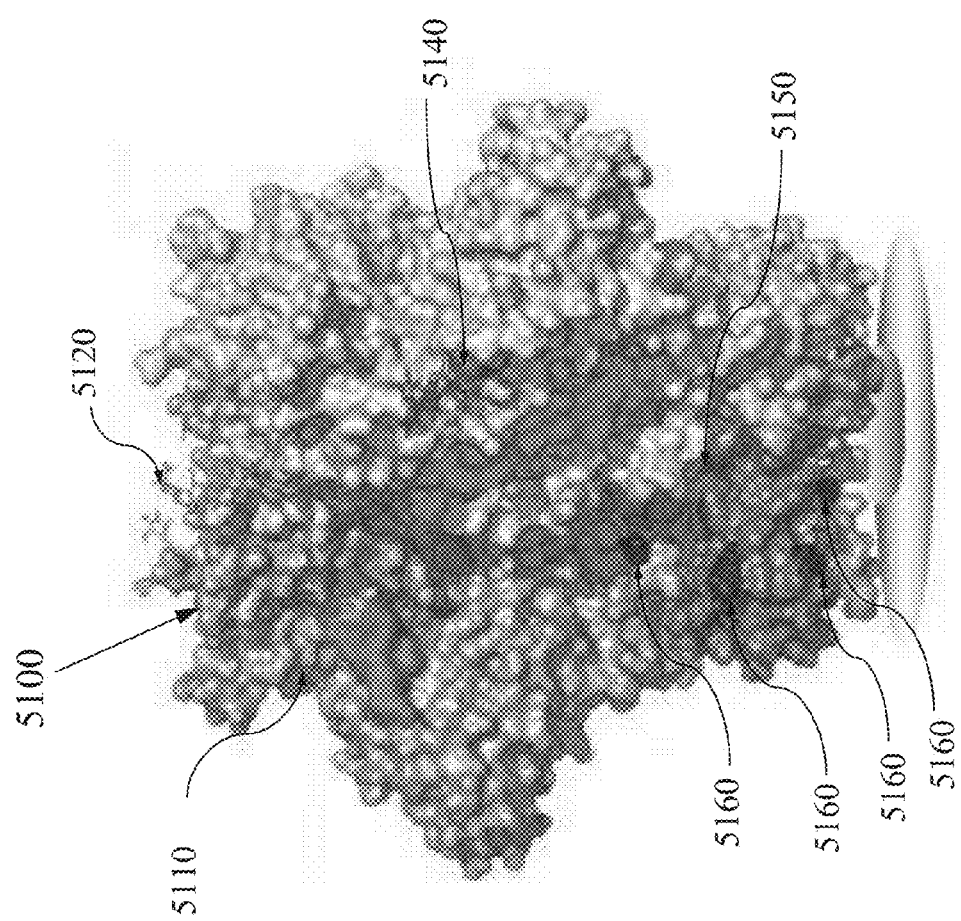
FIG. 51 is an image showing the epitope signatures recognized by various antibodies (Abs) in the 3D context of a gp140 trimer structure (PDB 4tvp).

FIG. 51 is an image showing the epitope signatures recognized by various antibodies (Abs) in the 3D context of a gp140 trimer structure 5100 (PDB 4tvp; the model is generated by PyMol. 69.[69] These epitope signatures are color coded and include amino acid residues as well as glycans. AS shown in FIG. 51, a gp140 trimer structure 5100 has several epitope signatures that are targeted by various antibodies. For example, antibodies VRC01, b6, F105, etc. can bind at epitope signature 5110; epitope signature 5120 can be bound by antibodies PG9, PG16, PGT145, etc.; epitope signature 5140 can be bound by 2G12, PGT121, etc.; epitope signature 5150 can be bound by antibody F240; epitope signature 5160 can be bound by antibody PGT151.

Figure 52:
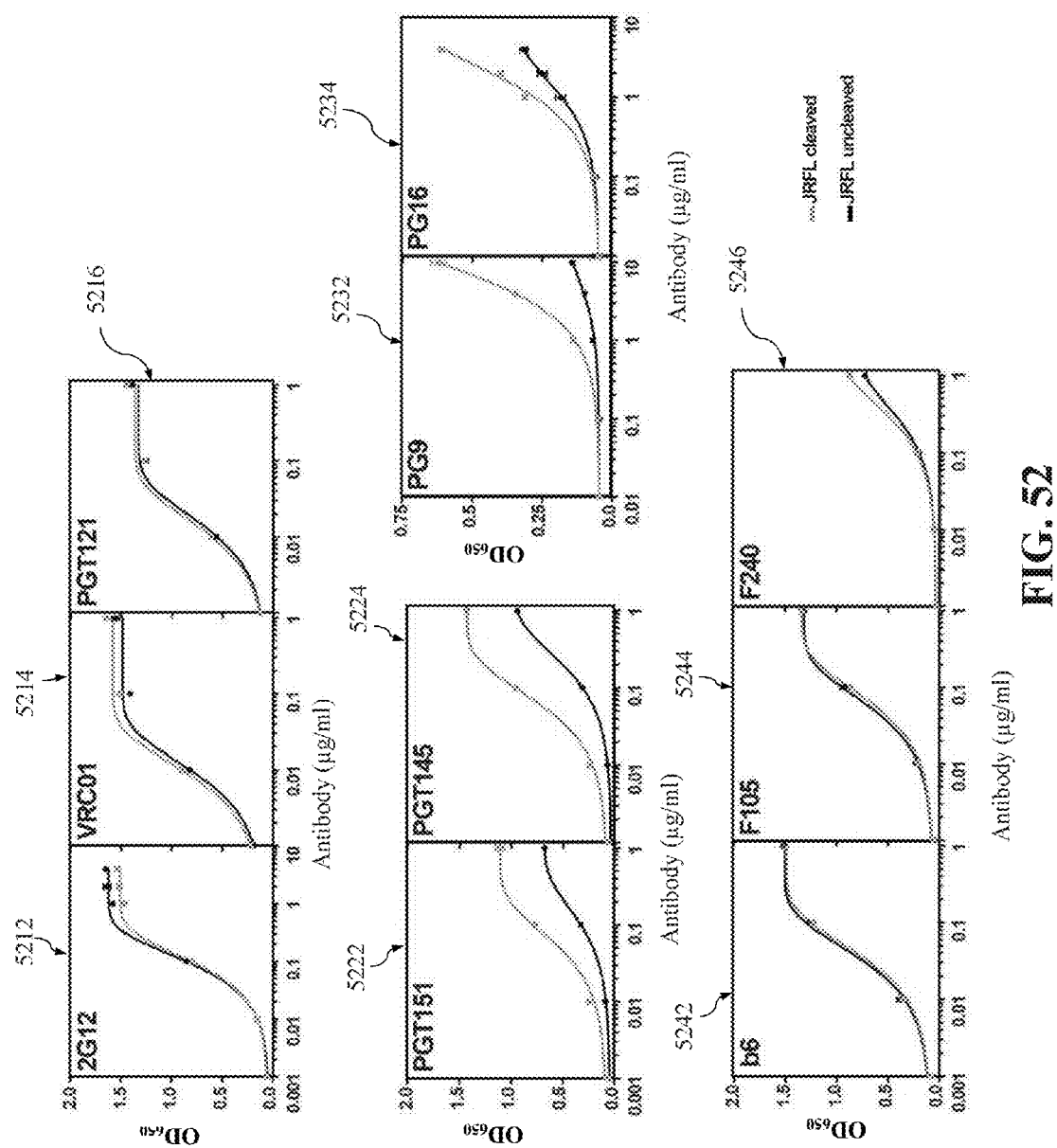
FIG. 52 is a set of graphs of results of ELISA performed with purified cleaved and uncleaved gp140 trimers with various mAbs.

FIG. 52 is a set of graphs of results of ELISA performed with purified cleaved and uncleaved gp140 trimers with various mAbs. Purified cleaved and uncleaved gp140 trimers are coated on STREP-TACTIN® plates through the C-terminal STREP-TAG® II and incubated with various antibodies (mAbs) that recognize different epitope signatures shown in FIG. 51. Various mAbs are shown in the top left corner of each graph in FIG. 52. ELISAs are performed. The protein concentration of the trimers per well is kept constant at 1 μg/ml. Each graph shows the binding curve from three replicates at the indicated concentrations of the mAb. Curves in lighter shade correspond to cleaved trimers; Curves in darker shade correspond to uncleaved trimers. The P value as determined by the unpaired two-tailed t test is <0.05 for PGT151, PGT145, PG9 and PG16 at 1 μg/ml of Ab. Repetition of ELISAs several times with independently purified trimers yield similar results. The results of the reactivity of the trimers tested to BnAbs 2G12, VRC01, and PGT121 are shown in FIG. 52 in graph 5212, graph 5214, and graph 5216, respectively. The results of the reactivity of the trimers tested to BnAbs PGT151 and PGT145 are shown in FIG. 52 in graph 5222 and graph 5224, respectively. The results of the reactivity of the trimers tested to BnAbs PG9 and PG16 are shown in FIG. 52 in graph 5232 and graph 5234, respectively. The results of the reactivity of the trimers tested to BnAbs b6, F105, and F240 are shown in FIG. 52 in graph 5242, graph 5244, and graph 5246, respectively.

Since coating is done at neutral pH (unlike at pH 9 in traditional ELISAs), it cause minimal, if any, structural perturbation. Moreover, the trimers are immobilized at a defined point; therefore, all immobilized molecules are exposed in a similar orientation, in some ways mimicking the Env spikes displayed on the HIV-1 virion. Finally, the 23aa flexible linker should make the trimer more accessible to Ab binding.

The reactivity of the trimers to BnAbs 2G12, VRC01, and PGT121 is first tested. 2G12 recognizes a discontinuous epitope consisting of 3 or 4 high mannose glycans in the gp120 domain.[64, 65] VRC01 is a potent BnAb that binds to the CD4bs and neutralizes >90% of the primary HIV-1 isolates.[17] PGT121 primarily recognizes the complex glycan attached to N332.[61] Consistent with the published data that the conformational epitopes recognized by these Abs are well-exposed in trimers as well as in gp120, both cleaved and uncleaved trimers react strongly, and equivalently, to these Abs (FIG. 51).[23, 26, 28, 66, 67]

The BnAb PGT151 recognizes a conformational epitope containing aa residues and glycans present at the interface of gp120 and gp41 that is better exposed in the cleaved trimers.[68, 68] The results show that the cleaved gp140 trimers exhibit stronger reactivity to PGT151 than the uncleaved trimers (see graph 5222 of FIG. 52), suggesting that cleaved trimers achieve native-like conformation.

The BnAbs PG16 and PG9 are quaternary Abs that neutralize 70-80% of the primary HIV-1 viruses. The quaternary specificity stems from its long hammerhead-shaped CDR which asymmetrically interacts with the V1,V2, and V3 loops of two protomers from the same trimer. The contact regions include, primarily, the V1V2 loop glycan N160 and N156/N173, and residue K168 of one protomer and glycans N160 and N197 (V3 loop) of the adjacent protomer.[29, 70, 71] PGT145 is also a quaternary BnAb, however less well characterized, and it, like PG9 and PG16, recognizes the N160 and N156/N173 glycans.[41,70] Consistent with the expectation that a compact trimer would react better with the quaternary Ab, the cleaved trimers react more strongly with PG9, PG16, and PGT145 BnAbs than the uncleaved trimers (FIG. 52).

Finally, the reactivity of the trimers with the non-neutralizing Abs (NnAbs) b6, F105, and F240 is tested. F105 and b6 recognize an epitope that includes CD4bs whereas F240 binds to the immunodominant loop of gp41 (aa592-604).[16,42,67,68,69] The CR and CP trimers as well as protomers reacted similarly with these NnAbs, although the reactivity with F240 is poor overall probably because its epitope is partially occluded. (FIG. 51, epitope signature 5150).

Collectively, these data demonstrate that the trimers display antigenic signatures that are consistent with their cleaved or uncleaved states. Differential reactivity with the quaternary epitopes provides the best benchmark to ascertain the antigenic signature of compact, native-like trimers.

Discussion

The trimeric envelope spike of HIV-1 virion makes the first contact with the host cell. It triggers fusion of viral and host membranes and delivers the nucleocapsid core into the cell. Trimer-specific Abs can disable Env function and block transmission of HIV. Development of a recombinant trimer immunogen, therefore, is one of the highest priorities in the hunt for an effective HIV vaccine.[26,31,75] However, a myriad of variations reported in the literature leads to confusion and controversy, and none can be broadly applied to diverse strains of HIV. For instance, a procedure that produces native-like trimers from A-clade BG505 by using 2G12 BnAb to capture gp140 is not as effective with the B-clade JRFL trimers.[26,31] Hence, another procedure is developed in which lectin capture and negative selection by F105 NnAb is used to purify trimers.[31] These Ab-based approaches have inherent limitations since the epitope signatures may vary from one HIV clade to another. In fact, it is necessary to mutate the wild-type BG505 gp140 in order to create the 2G12 binding epitope and allow for its purification by the 2G12 BnAb.[26,66] and moreover, the Abs are not readily available, prohibitively expensive, and not practical for vaccine production.

Here, a new approach is developed that allows production of HIV Env trimers from potentially any HIV-1 clade or strain. Systematic analyses are presented to optimize trimer production, and biochemical characterizations to define the signatures of trimers.

A key feature of the approach disclosed herein is to selectively capture gp140 Env directly from the culture supernatant under mild conditions that cause minimal, if any, perturbation to the structure or oligomeric state of the protein. Attempts to achieve this using an affinity tag have thus far failed because the tag is not accessible for interaction with its binding partner. In accordance with the recent X-ray structures, the C-terminal aa664 would not be accessible as it is the last residue of the long HR2 helices that encircle the base of the gp140 trimer.[29,69] It is further shielded by as many as 12 glycans emanating from these helices.[29,69] Therefore it is essential not only to incorporate an exquisitely specific STREP-TAG® II, but also to separate the tag from the base by a >20aa-long linker. These modifications avoid clashes with the trimer base and allow purification of near homogeneous protein in a single step. A variety of gp140 variants; cleaved, uncleaved, GnTI⁻ glycosylated, and 293F glycosylated from clades A, B, and A-E viruses can be purified by this approach.

The Strep-Tagged gp140 proteins behaved similar to the native gp140. For instance, the CP gp140 is nearly completely cleaved to gp120 and gp41 and the CR gp140 remained uncleaved. SOSIP mutations are essential; otherwise, most of the gp140 aggregate into a high MW fraction. Curiously, gp41 glycosylation is heterogeneous, showing five gp41 bands corresponding to glycosylation of zero to four sites of the four N-linked glycosylation sites clustered in or near the 34aa-long HR2 helix. This micro-heterogeneity, which is observed in both JRFL and BG505 gp140, may reflect a competition between the rate of glycosylation and the rate of folding of this transiently exposed structural element.

The results show that cleavage is not essential for trimerization per se, but it is essential for maturation into propeller-shaped particles. Uncleaved gp140 produced such native-like articles but in fewer and variable numbers. Maturation might involve two, probably sequential, events, conformational transition and complex glycosylation.[76] A cleavage-triggered conformational transition can be deduced from a number of experiments. Truncated CP gp140 constructs beyond aa664, e.g., aa683, produce 3-5 times lower amounts of gp140, whereas the same truncation in CR background is not significantly affected, and much of the aa683 protein aggregate. Thus, conformation of MPER where these residues are located must be different in the cleaved and uncleaved states. These results are consistent with the previous reports by Klasse et al., and Ringe et al.,[26] which showed that the cleaved aa681 and aa683 proteins formed micelles at the MPER. Perhaps some of the residues in the hydrophobic-rich MPER are better exposed in the cleaved state and associate with the membrane. Structural studies suggest that the MPER forms an L-shaped bent helix and the residues 675-683 contact the virion membrane.[77]

Secondly, cleaved trimers exhibited greater stability and are less susceptible to proteolysis than the uncleaved trimers suggesting that cleavage renders the trimers more compact and less accessible to protease. Finally, negative-stain EM shows compact, propeller-shaped trimers in the cleaved state and irregularly shaped "blobs" in the uncleaved state, as is also observed by Ringe et al with the 2G12 produced trimers (Table 1).[26]

Careful analysis of glycosylation patterns show that cleavage channels trimers into the correct glycosylation pathway. Without cleavage, trimers from both JRFL and BG505 enter an aberrant pathway resulting in hyper-glycosylation, which traps the trimers in a loosely associated state. Consequently, the uncleaved trimers including the foldon trimers produced by 293F cells are conformationally heterogeneous, nonspecifically disulfide crosslinked, more susceptible to proteolysis, and irregularly shaped. Presence of a diffuse smear in the native gel, poor reactivity with the conformation-specific PGT145 BnAbs, and heterogeneity in gp41 complex glycosylations, provide further evidence of this phenotype. Finally, the uncleaved trimers from GnTI⁻ cells which are unable to carry out hyper-glycosylations show a higher percentage of native-like trimers, further underscoring the negative effects of hyper-glycosylation.

The strong reactivity of the CR and CP trimers with the BnAbs 2G12, VRC01, and PGT121 confirms that the Strep-Tagged trimers have a correctly folded gp120 and gp41 ectodomain exposing the respective conformational epitopes. Preferential reactivity of the cleaved trimers with the PGT151 BnAb further confirms the integrity of the conformational epitope that emerges at the interface of gp120 and gp41 following cleavage. Strong reactivity with cleaved trimers, but not with uncleaved trimers, of the quaternary BnAbs PG9 and PG16 demonstrates that CP gp140 protomers assemble into correct quaternary structure.

Contrary to some reports that the CR trimers, but not the CP trimers, react with the NnAbs, both of CR and CP trimers react similarly with the NnAbs b6, F240, and F105.[66] Table 2 shows the reactivity of various cleaved and uncleaved trimers with non-neutralizing antibodies using different assay platforms. The table shows the reactivity of various cleaved (CP) and uncleaved (CR) trimer preparations with the non-neutralizing Abs b6, F105, and F240, using different assay platforms reported in the literature. Scores are assigned based on a comparison of the reactivity of different gp140 constructs reported in the same figure from each publication. Different publications are grouped into one line if the scores match. Reactivity scores: +++ high, ++ moderate, + weak, +/- above baseline, - negative. The reactivity is dependent on the assay platform (compare the reactivity of BG505.SOSIP.R6.664 in ELISA vs SPR vs BLI) and the presence of SOSIP mutation [compare the reactivity of BG505.SOSIP.SEKS.664 (line 4) vs BG505.WT.SEKS.664 by SPR (line 5)]. Also, the ELISA data of BG505.SOSIP.R6.664 is compared to BG505.WT.SEKS.664 but not to its counterpart BG505.SOSIP.SEKS.664.

TABLE 2

Reactivity of various cleaved and uncleaved trimers with non-neutralizing antibodies using different assay platforms:

| Construct | Composition | Cleavage | b6 | F105 | F240 | References |
|---|---|---|---|---|---|---|
| ELISA | | | | | | |
| 1. BG505.SOSIP.R6.664 | Trimer | CP | +++ | + | ++ | (26, 28) |
| 2. BG505.WT.SEKS.664 | Trimer | CR | +++ | +++ | +++ | (26) |
| SPR | | | | | | |
| 3. BG505.SOSIP.R6.664 | Trimer | CP | -/+ | NR | - | (26, 28, 66) |
| 4. BG505.SOSIP.SEKS.664 | Trimer | CR | + | NR | -/+ | (26, 66) |
| 5. BG505.WT.SEKS.664 | Trimer | CR | +++ | NR | +++ | (26, 66) |
| Bio-layer interferometry BLI | | | | | | |
| 6. BG505.SOSIP.R6.664 | Trimer | CP | ++ | - | NR | (69) |
| 7. JRFL.SOSIP.R6.663 | Trimer | CP | +++ | ++ | NR | (31)* |
| 8. 16055.SOSIP.R6.663 | Trimer | CP | +++ | ++ | NR | (31)* |

NR—not reported
*Before negative selection

Careful examination of the published reports, however, shows that the reactivity depended on the type of assay platform used, and the sequences of the CR and CP trimers compared are not identical. On the other hand, data illustrated in some examples are generated using identical CP and CR sequences (except for the cleavage site) and the STREP-TACTIN® based ELISA platform is not expected to introduce significant structural perturbations into the trimeric antigens. Furthermore, the HIV Env trimer is a dynamic structure and likely oscillates between "closed" and "open" states, allowing the NnAb to interact with the trimer when it opens transiently.[78,79] Thus, strong reactivity to the quaternary-specific BnAbs such as PG9 and PG16 is the most reliable benchmark to assess the authenticity of the native-like trimers.

In conclusion, a new system to produce, optimize, and characterize pure and native-like HIV-1 Env trimers is developed herein. Both cleavage and proper glycosylation are critical to generate compact, three-blade propeller shaped particles, whereas without cleavage, the trimers are heterogeneous in conformation, nonspecifically crosslinked, and hyper-glycosylated, properties consistent with their irregular shape. The GnTI⁻ cells produced better quality trimers than the 293F cells. However, the 293F trimers might better recapitulate the native structure because GnTI⁻ cells lack complex glycosylations. The caveat, however, is that the glycan structures introduced by the 293F cells are not know and if these glycan structures are the same as that present on the HIV-1 virion. Micro-heterogeneity of glycosylations might also be a concern. Three criteria, namely ≥95% cleavage, near 100% propeller-shaped particles, and strong reactivity to quaternary BnAbs, define authentic HIV-1 trimers. The approach disclosed herein provides several useful features (see TABLE 1) and is broadly applicable to generate trimers from potentially any HIV-1 virus for basic research as well as for human clinical trials and vaccine manufacture. The well-behaved JRFL trimers described here may serve as a good scaffold for further engineering to generate a trimeric immunogen that can elicit transmission-blocking Abs against diverse HIV-1 strains.

It is intended that the invention not be limited to the particular embodiment disclosed herein contemplated for carrying out this invention, but that the invention will include all embodiments falling within the scope of the claims. For example, although the HIV-1 clade B JRFL gp140 and clade A BG505 gp140 sequences are used as templates in constructing recombinant HIV-1 gp140 and in producing trimeric envelope spike that mimics native-like HIV-1 trimers, it will be appreciated that sequences from other HIV-1 clades can be used as templates for producing, purifying and testing trimers produced according to the approach disclosed herein. Antibodies against HIV-1 that can be used in capturing "native-like" trimers are not limited to BnAb 2G12. In addition, tags that fused to recombinant HIV-1 gp140 are not limited to octa-histidine and STREP-TAG® II.

REFERENCES

The following references are referred to above and are incorporated herein by reference:

1. Kwong, P. D., and Mascola, J. R. (2012) Human antibodies that neutralize HIV-1: identification, structures, and B cell ontogenies. *Immunity* 37, 412-425
2. Mascola, J. R., and Nabel, G. J. (2001) Vaccines for the prevention of HIV-1 disease. *Curr Opin Immunol* 13, 489-495
3. Wyatt, R., and Sodroski, J. (1998) The HIV-1 envelope glycoproteins: fusogens, antigens, and immunogens. *Science* 280, 1884-1888
4. Ward, A. B., and Wilson, I. A. (2015) Insights into the trimeric HIV-1 envelope glycoprotein structure. *Trends Biochem Sci*
5. Wilen, C. B., Tilton, J. C., and Doms, R. W. (2012) Molecular mechanisms of HIV entry. *Adv Exp Med Biol* 726, 223-242
6. Arthos, J., Cicala, C., Martinelli, E., Macleod, K., Van Ryk, D., Wei, D., Xiao, Z., Veenstra, T. D., Conrad, T. P., Lempicki, R. A., McLaughlin, S., Pascuccio, M., Gopaul, R., McNally, J., Cruz, C. C., Censoplano, N., Chung, E., Reitano, K. N., Kottilil, S., Goode, D. J., and Fauci, A. S. (2008) HIV-1 envelope protein binds to and signals through integrin alpha4beta7, the gut mucosal homing receptor for peripheral T cells. *Nat Immunol* 9, 301-309
7. Cicala, C., Arthos, J., and Fauci, A. S. (2011) HIV-1 envelope, integrins and co-receptor use in mucosal transmission of HIV. *J Transl Med* 9 Suppl 1, S2
8. Dalgleish, A. G., Beverley, P. C., Clapham, P. R., Crawford, D. H., Greaves, M. F., and Weiss, R. A. (1984) The CD4 (T4) antigen is an essential component of the receptor for the AIDS retrovirus. *Nature* 312, 763-767
9. McDougal, J. S., Nicholson, J. K., Cross, G. D., Cort, S. P., Kennedy, M. S., and Mawle, A. C. (1986) Binding of the human retrovirus HTLV-III/LAV/ARV/HIV to the CD4 (T4) molecule: conformation dependence, epitope mapping, antibody inhibition, and potential for idiotypic mimicry. *J Immunol* 137, 2937-2944
10. Klatzmann, D., Champagne, E., Chamaret, S., Gruest, J., Guetard, D., Hercend, T., Gluckman, J. C., and Montagnier, L. (1984) T-lymphocyte T4 molecule behaves as the receptor for human retrovirus LAV. *Nature* 312, 767-768
11. Alkhatib, G., Combadiere, C., Broder, C. C., Feng, Y., Kennedy, P. E., Murphy, P. M., and Berger, E. A. (1996) CC CKR5: a RANTES, MIP-1alpha, MIP-1beta receptor as a fusion cofactor for macrophage-tropic HIV-1. *Science* 272, 1955-1958
12. Feng, Y., Broder, C. C., Kennedy, P. E., and Berger, E. A. (1996) HIV-1 entry cofactor: functional cDNA cloning of a seven-transmembrane, G protein-coupled receptor. *Science* 272, 872-877
13. Lederman, M. M., Penn-Nicholson, A., Cho, M., and Mosier, D. (2006) Biology of CCR5 and its role in HIV infection and treatment. *JAMA* 296, 815-826
14. Furuta, R. A., Wild, C. T., Weng, Y., and Weiss, C. D. (1998) Capture of an early fusion-active conformation of HIV-1 gp41. *Nat Struct Biol* 5, 276-279
15. Gallo, S. A., Finnegan, C. M., Viard, M., Raviv, Y., Dimitrov, A., Rawat, S. S., Puri, A., Durell, S., and Blumenthal, R. (2003) The HIV Env-mediated fusion reaction. *Biochim Biophys Acta* 1614, 36-50
16. Roben, P., Moore, J. P., Thali, M., Sodroski, J., Barbas, C. F., 3rd, and Burton, D. R. (1994) Recognition properties of a panel of human recombinant Fab fragments to the CD4 binding site of gp120 that show differing abilities to neutralize human immunodeficiency virus type 1. *J Virol* 68, 4821-4828
17. Wu, X., Yang, Z. Y., Li, Y., Hogerkorp, C. M., Schief, W. R., Seaman, M. S., Zhou, T., Schmidt, S. D., Wu, L., Xu, L., Longo, N. S., McKee, K., O'Dell, S., Louder, M. K., Wycuff, D. L., Feng, Y., Nason, M., Doria-Rose, N., Connors, M., Kwong, P. D., Roederer, M., Wyatt, R. T., Nabel, G. J., and Mascola, J. R. (2010) Rational design of envelope identifies broadly neutralizing human monoclonal antibodies to HIV-1. *Science* 329, 856-861
18. Zwick, M. B., Jensen, R., Church, S., Wang, M., Stiegler, G., Kunert, R., Katinger, H., and Burton, D. R. (2005) Anti-human immunodeficiency virus type 1 (HIV-1) antibodies 2F5 and 4E10 require surprisingly few crucial residues in the membrane-proximal external region of glycoprotein gp41 to neutralize HIV-1. *J Virol* 79, 1252-1261

19. Walker, L. M., Phogat, S. K., Chan-Hui, P. Y., Wagner, D., Phung, P., Goss, J. L., Wrin, T., Simek, M. D., Fling, S., Mitcham, J. L., Lehrman, J. K., Priddy, F. H., Olsen, O. A., Frey, S. M., Hammond, P. W., Protocol, G. P. I., Kaminsky, S., Zamb, T., Moyle, M., Koff, W. C., Poignard, P., and Burton, D. R. (2009) Broad and potent neutralizing antibodies from an African donor reveal a new HIV-1 vaccine target. *Science* 326, 285-289

20. Benjelloun, F., Lawrence, P., Verrier, B., Genin, C., and Paul, S. (2012) Role of human immunodeficiency virus type 1 envelope structure in the induction of broadly neutralizing antibodies. *J Virol* 86, 13152-13163

21. Yu, L., and Guan, Y. (2014) Immunologic Basis for Long HCDR3s in Broadly Neutralizing Antibodies Against HIV-1. *Front Immunol* 5, 250

22. Esparza, J. (2013) A brief history of the global effort to develop a preventive HIV vaccine. *Vaccine* 31, 3502-3518

23. Chakrabarti, B. K., Feng, Y., Sharma, S. K., McKee, K., Karlsson Hedestam, G. B., Labranche, C. C., Montefiori, D. C., Mascola, J. R., and Wyatt, R. T. (2013) Robust neutralizing antibodies elicited by HIV-1 JRFL envelope glycoprotein trimers in nonhuman primates. *J Virol* 87, 13239-13251

24. Kovacs, J. M., Nkolola, J. P., Peng, H., Cheung, A., Perry, J., Miller, C. A., Seaman, M. S., Barouch, D. H., and Chen, B. (2012) HIV-1 envelope trimer elicits more potent neutralizing antibody responses than monomeric gp120. *Proc Natl Acad Sci USA* 109, 12111-12116

25. Nkolola, J. P., Cheung, A., Perry, J. R., Carter, D., Reed, S., Schuitemaker, H., Pau, M. G., Seaman, M. S., Chen, B., and Barouch, D. H. (2014) Comparison of multiple adjuvants on the stability and immunogenicity of a clade C HIV-1 gp140 trimer. *Vaccine* 32, 2109-2116

26. Ringe, R. P., Sanders, R. W., Yasmeen, A., Kim, H. J., Lee, J. H., Cupo, A., Korzun, J., Derking, R., van Montfort, T., Julien, J. P., Wilson, I. A., Klasse, P. J., Ward, A. B., and Moore, J. P. (2013) Cleavage strongly influences whether soluble HIV-1 envelope glycoprotein trimers adopt a native-like conformation. *Proc Natl Acad Sci USA* 110, 18256-18261

27. Liao, H. X., Lynch, R., Zhou, T., Gao, F., Alam, S. M., Boyd, S. D., Fire, A. Z., Roskin, K. M., Schramm, C. A., Zhang, Z., Zhu, J., Shapiro, L., Program, N. C. S., Mullikin, J. C., Gnanakaran, S., Hraber, P., Wiehe, K., Kelsoe, G., Yang, G., Xia, S. M., Montefiori, D. C., Parks, R., Lloyd, K. E., Scearce, R. M., Soderberg, K. A., Cohen, M., Kamanga, G., Louder, M. K., Tran, L. M., Chen, Y., Cai, F., Chen, S., Moquin, S., Du, X., Joyce, M. G., Srivatsan, S., Zhang, B., Zheng, A., Shaw, G. M., Hahn, B. H., Kepler, T. B., Korber, B. T., Kwong, P. D., Mascola, J. R., and Haynes, B. F. (2013) Co-evolution of a broadly neutralizing HIV-1 antibody and founder virus. *Nature* 496, 469-476

28. Sanders, R. W., Derking, R., Cupo, A., Julien, J. P., Yasmeen, A., de Val, N., Kim, H. J., Blattner, C., de la Pena, A. T., Korzun, J., Golabek, M., de Los Reyes, K., Ketas, T. J., van Gils, M. J., King, C. R., Wilson, I. A., Ward, A. B., Klasse, P. J., and Moore, J. P. (2013) A nextgeneration cleaved, soluble HIV-1 Env Trimer, BG505 SOSIP.664 gp140, expresses multiple epitopes for broadly neutralizing but not non-neutralizing antibodies. *PLoS Pathog* 9, e1003618

29. Julien, J. P., Cupo, A., Sok, D., Stanfield, R. L., Lyumkis, D., Deller, M. C., Klasse, P. J., Burton, D. R., Sanders, R. W., Moore, J. P., Ward, A. B., and Wilson, I. A. (2013) Crystal structure of a soluble cleaved HIV-1 envelope trimer. *Science* 342, 1477-1483

30. Lyumkis, D., Julien, J. P., de Val, N., Cupo, A., Potter, C. S., Klasse, P. J., Burton, D. R., Sanders, R. W., Moore, J. P., Carragher, B., Wilson, I. A., and Ward, A. B. (2013) Cryo-EM structure of a fully glycosylated soluble cleaved HIV-1 envelope trimer. *Science* 342, 1484-1490

31. Guenaga, J., de Val, N., Tran, K., Feng, Y., Satchwell, K., Ward, A. B., and Wyatt, R. T. (2015) Well-Ordered Trimeric HIV-1 Subtype B and C Soluble Spike Mimetics Generated by Negative Selection Display Native-like Properties. *PLoS Pathog* 11, e1004570

32. Gao, G., Wieczorek, L., Peachman, K. K., Polonis, V. R., Alving, C. R., Rao, M., and Rao, V. B. (2013) Designing a soluble near full-length HIV-1 gp41 trimer. *J Biol Chem* 288, 234-246

33. Tao, P., Mahalingam, M., Marasa, B. S., Zhang, Z., Chopra, A. K., and Rao, V. B. (2013) In vitro and in vivo delivery of genes and proteins using the bacteriophage T4 DNA packaging machine. *Proc Natl Acad Sci USA* 110, 5846-5851

34. Sathaliyawala, T., Rao, M., Maclean, D. M., Birx, D. L., Alving, C. R., and Rao, V. B. (2006) Assembly of human immunodeficiency virus (HIV) antigens on bacteriophage T4: a novel in vitro approach to construct multicomponent HIV vaccines. *J Virol* 80, 7688-7698

35. Liu, J., Bartesaghi, A., Borgnia, M. J., Sapiro, G., and Subramaniam, S. (2008) Molecular architecture of native HIV-1 gp120 trimers. *Nature* 455, 109-113

36. Buchacher, A., Predl, R., Strutzenberger, K., Steinfellner, W., Trkola, A., Purtscher, M., Gruber, G., Tauer, C., Steindl, F., Jungbauer, A., and et al. (1994) Generation of human monoclonal antibodies against HIV-1 proteins; electrofusion and Epstein-Barr virus transformation for peripheral blood lymphocyte immortalization. *AIDS Res Hum Retroviruses* 10, 359-369

37. Trkola, A., Purtscher, M., Muster, T., Ballaun, C., Buchacher, A., Sullivan, N., Srinivasan, K., Sodroski, J., Moore, J. P., and Katinger, H. (1996) Human monoclonal antibody 2G12 defines a distinctive neutralization epitope on the gp120 glycoprotein of human immunodeficiency virus type 1. *J Virol* 70, 1100-1108

38. Mascola, J. R., Lewis, M. G., Stiegler, G., Harris, D., VanCott, T. C., Hayes, D., Louder, M. K., Brown, C. R., Sapan, C. V., Frankel, S. S., Lu, Y., Robb, M. L., Katinger, H., and Birx, D. L. (1999) Protection of Macaques against pathogenic simian/human immunodeficiency virus 89.6PD by passive transfer of neutralizing antibodies. *J Virol* 73, 4009-4018

39. Etemad-Moghadam, B., Sun, Y., Nicholson, E. K., Karlsson, G. B., Schenten, D., and Sodroski, J. (1999) Determinants of neutralization resistance in the envelope glycoproteins of a simianhuman immunodeficiency virus passaged in vivo. *J Virol* 73, 8873-8879

40. Crawford, J. M., Earl, P. L., Moss, B., Reimann, K. A., Wyand, M. S., Manson, K. H., Bilska, M., Zhou, J. T., Pauza, C. D., Parren, P. W., Burton, D. R., Sodroski, J. G., Letvin, N. L., and Montefiori, D. C. (1999) Characterization of primary isolate-like variants of simian-human immunodeficiency virus. *J Virol* 73, 10199-10207

41. Walker, L. M., Huber, M., Doores, K. J., Falkowska, E., Pejchal, R., Julien, J. P., Wang, S. K., Ramos, A., Chan-Hui, P. Y., Moyle, M., Mitcham, J. L., Hammond, P. W., Olsen, O. A., Phung, P., Fling, S., Wong, C. H., Phogat, S., Wrin, T., Simek, M. D., Protocol, G. P. I., Koff, W. C., Wilson, I. A., Burton, D. R., and Poignard, P. (2011) Broad neutralization coverage of HIV by multiple highly potent antibodies. *Nature* 477, 466-470

42. Cavacini, L. A., Emes, C. L., Wisnewski, A. V., Power, J., Lewis, G., Montefiori, D., and Posner, M. R. (1998)

Functional and molecular characterization of human monoclonal antibody reactive with the immunodominant region of HIV type 1 glycoprotein 41. *AIDS Res Hum Retroviruses* 14, 1271-1280

43. Posner, M. R., Elboim, H., and Santos, D. (1987) The construction and use of a human-mouse myeloma analogue suitable for the routine production of hybridomas secreting human monoclonal antibodies. *Hybridoma* 6, 611-625

44. Posner, M. R., Hideshima, T., Cannon, T., Mukherjee, M., Mayer, K. H., and Byrn, R. A. (1991) An IgG human monoclonal antibody that reacts with HIV-1/GP120, inhibits virus binding to cells, and neutralizes infection. *J Immunol* 146, 4325-4332

45. Posner, M. R., Cavacini, L. A., Emes, C. L., Power, J., and Byrn, R. (1993) Neutralization of HIV-1 by F105, a human monoclonal antibody to the CD4 binding site of gp120. *J Acquir Immune Defic Syndr* 6, 7-14

46. Cavacini, L. A., Emes, C. L., Power, J., Underdahl, J., Goldstein, R., Mayer, K., and Posner, M. R. (1993) Loss of serum antibodies to a conformational epitope of HIV-1/gp120 identified by a human monoclonal antibody is associated with disease progression. *J Acquir Immune Defic Syndr* 6, 1093-1102

47. Falkowska, E., Le, K. M., Ramos, A., Doores, K. J., Lee, J. H., Blattner, C., Ramirez, A., Derking, R., van Gils, M. J., Liang, C. H., McBride, R., von Bredow, B., Shivatare, S. S., Wu, C. Y., Chan-Hui, P. Y., Liu, Y., Feizi, T., Zwick, M. B., Koff, W. C., Seaman, M. S., Swiderek, K., Moore, J. P., Evans, D., Paulson, J. C., Wong, C. H., Ward, A. B., Wilson, I. A., Sanders, R. W., Poignard, P., and Burton, D. R. (2014) Broadly neutralizing HIV antibodies define a glycandependent epitope on the prefusion conformation of gp41 on cleaved envelope trimers. *Immunity* 40, 657-668

48. Yang, X., Lee, J., Mahony, E. M., Kwong, P. D., Wyatt, R., and Sodroski, J. (2002) Highly stable trimers formed by human immunodeficiency virus type 1 envelope glycoproteins fused with the trimeric motif of T4 bacteriophage fibritin. *J Virol* 76, 4634-4642

49. Binley, J. M., Sanders, R. W., Clas, B., Schuelke, N., Master, A., Guo, Y., Kajumo, F., Anselma, D. J., Maddon, P. J., Olson, W. C., and Moore, J. P. (2000) A recombinant human immunodeficiency virus type 1 envelope glycoprotein complex stabilized by an intermolecular disulfide bond between the gp120 and gp41 subunits is an antigenic mimic of the trimeric virionassociated structure. *J Virol* 74, 627-643

50. Sanders, R. W., Vesanen, M., Schuelke, N., Master, A., Schiffner, L., Kalyanaraman, R., Paluch, M., Berkhout, B., Maddon, P. J., Olson, W. C., Lu, M., and Moore, J. P. (2002) Stabilization of the soluble, cleaved, trimeric form of the envelope glycoprotein complex of human immunodeficiency virus type 1. *J Virol* 76, 8875-8889

51. Dey, A. K., David, K. B., Klasse, P. J., and Moore, J. P. (2007) Specific amino acids in the Nterminus of the gp41 ectodomain contribute to the stabilization of a soluble, cleaved gp140 envelope glycoprotein from human immunodeficiency virus type 1. *Virology* 360, 199-208

52. Binley, J. M., Sanders, R. W., Master, A., Cayanan, C. S., Wiley, C. L., Schiffner, L., Travis, B., Kuhmann, S., Burton, D. R., Hu, S. L., Olson, W. C., and Moore, J. P. (2002) Enhancing the proteolytic maturation of human immunodeficiency virus type 1 envelope glycoproteins. *J Virol* 76, 2606-2616

53. Hoffenberg, S., Powell, R., Carpov, A., Wagner, D., Wilson, A., Kosakovsky Pond, S., Lindsay, R., Arendt, H., Destefano, J., Phogat, S., Poignard, P., Fling, S. P., Simek, M., Labranche, C., Montefiori, D., Wrin, T., Phung, P., Burton, D., Koff, W., King, C. R., Parks, C. L., and Caulfield, M. J. (2013) Identification of an HIV-1 clade A envelope that exhibits broad antigenicity and neutralization sensitivity and elicits antibodies targeting three distinct epitopes. *J Virol* 87, 5372-5383

54. Kong, L., Lee, J. H., Doores, K. J., Murin, C. D., Julien, J. P., McBride, R., Liu, Y., Marozsan, A., Cupo, A., Klasse, P. J., Hoffenberg, S., Caulfield, M., King, C. R., Hua, Y., Le, K. M., Khayat, R., Deller, M. C., Clayton, T., Tien, H., Feizi, T., Sanders, R. W., Paulson, J. C., Moore, J. P., Stanfield, R. L., Burton, D. R., Ward, A. B., and Wilson, I. A. (2013) Supersite of immune vulnerability on the glycosylated face of HIV-1 envelope glycoprotein gp120. *Nat Struct Mol Biol* 20, 796-803

55. Higuchi, R., Krummel, B., and Saiki, R. K. (1988) A general method of in vitro preparation and specific mutagenesis of DNA fragments: study of protein and DNA interactions. *Nucleic Acids Res* 16, 7351-7367

56. Stemmer, W. P., Crameri, A., Ha, K. D., Brennan, T. M., and Heyneker, H. L. (1995) Single-step assembly of a gene and entire plasmid from large numbers of oligodeoxyribonucleotides. *Gene* 164, 49-53

57. Reeves, P. J., Kim, J. M., and Khorana, H. G. (2002) Structure and function in rhodopsin: a tetracycline-inducible system in stable mammalian cell lines for high-level expression of opsin mutants. *Proc Natl Acad Sci USA* 99, 13413-13418

58. Tang, G., Peng, L., Baldwin, P. R., Mann, D. S., Jiang, W., Rees, I., and Ludtke, S. J. (2007) EMAN2: an extensible image processing suite for electron microscopy. *J Struct Biol* 157, 38-46

59. Tran, K., Poulsen, C., Guenaga, J., de Val, N., Wilson, R., Sundling, C., Li, Y., Stanfield, R. L., Wilson, I. A., Ward, A. B., Karlsson Hedestam, G. B., and Wyatt, R. T. (2014) Vaccine-elicited primate antibodies use a distinct approach to the HIV-1 primary receptor binding site informing vaccine redesign. *Proc Natl Acad Sci USA* 111, E738-747

60. Georgiev, I. S., Joyce, M. G., Yang, Y., Sastry, M., Zhang, B., Baxa, U., Chen, R. E., Druz, A., Lees, C. R., Narpala, S., Schon, A., Van Galen, J., Chuang, G. Y., Gorman, J., Harned, A., Pancera, M., Stewart-Jones, G. B., Cheng, C., Freire, E., McDermott, A. B., Mascola, J. R., and Kwong, P. D. (2015) Single-chain soluble BG505.SOSIP gp140 trimers as structural and antigenic mimics of mature closed HIV-1 Env. *J Virol*

61. Julien, J. P., Sok, D., Khayat, R., Lee, J. H., Doores, K. J., Walker, L. M., Ramos, A., Diwanji, D. C., Pejchal, R., Cupo, A., Katpally, U., Depetris, R. S., Stanfield, R. L., McBride, R., Marozsan, A. J., Paulson, J. C., Sanders, R. W., Moore, J. P., Burton, D. R., Poignard, P., Ward, A. B., and Wilson, I. A. (2013) Broadly neutralizing antibody PGT121 allosterically modulates CD4 binding via recognition of the HIV-1 gp120 V3 base and multiple surrounding glycans. *PLoS Pathog* 9, e1003342

62. Depetris, R. S., Julien, J. P., Khayat, R., Lee, J. H., Pejchal, R., Katpally, U., Cocco, N., Kachare, M., Massi, E., David, K. B., Cupo, A., Marozsan, A. J., Olson, W. C., Ward, A. B., Wilson, I. A., Sanders, R. W., and Moore, J. P. (2012) Partial enzymatic deglycosylation preserves the structure of cleaved recombinant HIV-1 envelope glycoprotein trimers. *J Biol Chem* 287, 24239-24254

63. Guttman, M., Garcia, N. K., Cupo, A., Matsui, T., Julien, J. P., Sanders, R. W., Wilson, I. A., Moore, J. P., and Lee, K. K. (2014) CD4-induced activation in a soluble HIV-1 Env trimer. *Structure* 22, 974-984

64. Sanders, R. W., Venturi, M., Schiffner, L., Kalyanaraman, R., Katinger, H., Lloyd, K. O., Kwong, P. D., and Moore, J. P. (2002) The mannose-dependent epitope for neutralizing antibody 2G12 on human immunodeficiency virus type 1 glycoprotein gp120. *J Virol* 76, 7293-7305

65. Murin, C. D., Julien, J. P., Sok, D., Stanfield, R. L., Khayat, R., Cupo, A., Moore, J. P., Burton, D. R., Wilson, I. A., and Ward, A. B. (2014) Structure of 2G12 Fab2 in complex with soluble and fully glycosylated HIV-1 Env by negative-stain single-particle electron microscopy. *J Virol* 88, 10177-10188

66. Yasmeen, A., Ringe, R., Derking, R., Cupo, A., Julien, J. P., Burton, D. R., Ward, A. B., Wilson, I. A., Sanders, R. W., Moore, J. P., and Klasse, P. J. (2014) Differential binding of neutralizing and non-neutralizing antibodies to native-like soluble HIV-1 Env trimers, uncleaved Env proteins, and monomeric subunits. *Retrovirology* 11, 41

67. Pancera, M., and Wyatt, R. (2005) Selective recognition of oligomeric HIV-1 primary isolate envelope glycoproteins by potently neutralizing ligands requires efficient precursor cleavage. *Virology* 332, 145-156

68. Blattner, C., Lee, J. H., Sliepen, K., Derking, R., Falkowska, E., de la Pena, A. T., Cupo, A., Julien, J. P., van Gils, M., Lee, P. S., Peng, W., Paulson, J. C., Poignard, P., Burton, D. R., Moore, J. P., Sanders, R. W., Wilson, I. A., and Ward, A. B. (2014) Structural delineation of a quaternary, cleavage-dependent epitope at the gp41-gp120 interface on intact HIV-1 Env trimers. *Immunity* 40, 669-680

69. Pancera, M., Zhou, T., Druz, A., Georgiev, I. S., Soto, C., Gorman, J., Huang, J., Acharya, P., Chuang, G. Y., Ofek, G., Stewart-Jones, G. B., Stuckey, J., Bailer, R. T., Joyce, M. G., Louder, M. K., Tumba, N., Yang, Y., Zhang, B., Cohen, M. S., Haynes, B. F., Mascola, J. R., Morris, L., Munro, J. B., Blanchard, S. C., Mothes, W., Connors, M., and Kwong, P. D. (2014) Structure and immune recognition of trimeric pre-fusion HIV-1 Env. *Nature* 514, 455-461

70. McLellan, J. S., Pancera, M., Carrico, C., Gorman, J., Julien, J. P., Khayat, R., Louder, R., Pejchal, R., Sastry, M., Dai, K., O'Dell, S., Patel, N., Shahzad-ul-Hussan, S., Yang, Y., Zhang, B., Zhou, T., Zhu, J., Boyington, J. C., Chuang, G. Y., Diwanji, D., Georgiev, I., Kwon, Y. D., Lee, D., Louder, M. K., Moquin, S., Schmidt, S. D., Yang, Z. Y., Bonsignori, M., Crump, J. A., Kapiga, S. H., Sam, N. E., Haynes, B. F., Burton, D. R., Koff, W. C., Walker, L. M., Phogat, S., Wyatt, R., Orwenyo, J., Wang, L. X., Arthos, J., Bewley, C. A., Mascola, J. R., Nabel, G. J., Schief, W. R., Ward, A. B., Wilson, I. A., and Kwong, P. D. (2011) Structure of HIV-1 gp120 V1/V2 domain with broadly neutralizing antibody PG9. *Nature* 480, 336-343

71. Julien, J. P., Lee, J. H., Cupo, A., Murin, C. D., Derking, R., Hoffenberg, S., Caulfield, M. J., King, C. R., Marozsan, A. J., Klasse, P. J., Sanders, R. W., Moore, J. P., Wilson, I. A., and Ward, A. B. (2013) Asymmetric recognition of the HIV-1 trimer by broadly neutralizing antibody PG9. *Proc Natl Acad Sci USA* 110, 4351-4356

72. Thali, M., Furman, C., Ho, D. D., Robinson, J., Tilley, S., Pinter, A., and Sodroski, J. (1992) Discontinuous, conserved neutralization epitopes overlapping the CD4-binding region of human immunodeficiency virus type 1 gp120 envelope glycoprotein. *J Virol* 66, 5635-5641

73. Chen, L., Kwon, Y. D., Zhou, T., Wu, X., O'Dell, S., Cavacini, L., Hessell, A. J., Pancera, M., Tang, M., Xu, L., Yang, Z. Y., Zhang, M. Y., Arthos, J., Burton, D. R., Dimitrov, D. S., Nabel, G. J., Posner, M. R., Sodroski, J., Wyatt, R., Mascola, J. R., and Kwong, P. D. (2009) Structural basis of immune evasion at the site of CD4 attachment on HIV-1 gp120. *Science* 326, 1123-1127

74. Cavacini, L. A., Duval, M., Robinson, J., and Posner, M. R. (2002) Interactions of human antibodies, epitope exposure, antibody binding and neutralization of primary isolate HIV-1 virions. *AIDS* 16, 2409-2417

75. Pugach, P., Ozorowski, G., Cupo, A., Ringe, R., Yasmeen, A., de Val, N., Derking, R., Kim, H. J., Korzun, J., Golabek, M., de Los Reyes, K., Ketas, T. J., Julien, J. P., Burton, D. R., Wilson, I. A., Sanders, R. W., Klasse, P. J., Ward, A. B., and Moore, J. P. (2015) A native-like SOSIP.664 trimer based on a HIV-1 subtype B env gene. *J Virol*

76. Checkley, M. A., Luttge, B. G., and Freed, E. O. (2011) HIV-1 envelope glycoprotein biosynthesis, trafficking, and incorporation. *J Mol Biol* 410, 582-608

77. Sun, Z. Y., Oh, K. J., Kim, M., Yu, J., Brusic, V., Song, L., Qiao, Z., Wang, J. H., Wagner, G., and Reinherz, E. L. (2008) HIV-1 broadly neutralizing antibody extracts its epitope from a kinked gp41 ectodomain region on the viral membrane. *Immunity* 28, 52-63

78. Bartesaghi, A., Merk, A., Borgnia, M. J., Milne, J. L., and Subramaniam, S. (2013) Prefusion structure of trimeric HIV-1 envelope glycoprotein determined by cryo-electron microscopy. *Nat Struct Mol Biol* 20, 1352-1357

79. Harris, A., Borgnia, M. J., Shi, D., Bartesaghi, A., He, H., Pejchal, R., Kang, Y. K., Depetris, R., Marozsan, A. J., Sanders, R. W., Klasse, P. J., Milne, J. L., Wilson, I. A., Olson, W. C., Moore, J. P., and Subramaniam, S. (2011) Trimeric HIV-1 glycoprotein gp140 immunogens and native HIV-1 envelope glycoproteins display the same closed and open quaternary molecular architectures. *Proc Natl Acad Sci USA* 108, 11440-11445

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising:
constructing a recombinant DNA encoding a recombinant protein by attaching a first nucleic acid sequence encoding a tag through a second nucleic acid sequence encoding a peptide linker at 3' end of a third nucleic acid sequence encoding a recombinant HIV-1 gp140; and
expressing the recombinant protein in cells growing in a culture medium;
wherein the recombinant protein comprises the recombinant HIV-1 gp140 fused to the tag through the peptide linker at C-terminus of the recombinant HIV-1 gp140;
wherein the recombinant protein expressed in cells assembles into recombinant trimers in the culture medium;
wherein each of the recombinant trimers comprises a trimer base formed by the recombinant HIV-1 gp140 not including the peptide linker and the tag;
wherein the peptide linker has a sufficient length to separate the tag from the trimer base so that the tag is accessible for binding by a binding molecule immobilized on a solid matrix used in protein purification, thereby allowing purification of the recombinant trimers from the culture medium;
wherein the recombinant trimers mimic native HIV-1 Env trimers,
wherein the peptide linker comprises at least 20 amino acids; and
wherein the peptide linker does not bind to the binding molecule during purification.

2. The method of claim 1, wherein the peptide linker comprises at least 23 amino acids.

3. The method of claim 1, wherein the peptide linker comprises SEQ ID NO: 1.

4. The method of claim 1, wherein the peptide linker comprises SEQ ID NO: 5.

5. The method of claim 1, wherein the peptide linker comprises SEQ ID NO: 6.

6. The method of claim 1, wherein the peptide linker comprises SEQ ID NO: 7.

7. The method of claim 1, wherein the peptide linker comprises a flexible linker.

8. The method of claim 7, wherein the flexible linker comprises SEQ ID NO: 8.

9. The method of claim 1, wherein the peptide linker comprises a rigid linker.

10. The method of claim 9, wherein the rigid linker comprises SEQ ID NO: 9.

11. The method of claim 1, wherein the tag comprises SEQ ID NO: 2.

12. The method of claim 1, wherein the tag comprises SEQ ID NO: 3.

13. The method of claim 1, wherein the recombinant HIV-1 gp140 encoded by the third nucleic acid sequence comprises a gp120 and a gp41 ectodomain, and wherein the gp120 and the gp41 ectodomain are joined by a junction sequence comprising a furin cleavage site REKR.

14. The method of claim 13, wherein the gp41 ectodomain is truncated at aa664 based on HXB2 numbering.

15. The method of claim 13, wherein the furin cleavage site REKR is mutated to SEKS, and wherein the recombinant HIV-1 gp140 is furin cleavage resistant.

16. The method of claim 13, wherein the furin cleavage site REKR is mutated to an amino acid sequence comprising SEQ ID NO: 13, and wherein the recombinant HIV-1 gp140 is furin cleavage proficient.

17. The method of claim 1, wherein the recombinant HIV-1 gp140 comprises "SOSIP" mutations that comprise A501C, T605C, and I559P, and wherein the recombinant HIV-1 gp140 comprises five "stabilizing" mutations comprising I535M, Q543L, S553N, K567Q, and R588G.

18. The method of claim 1, wherein the recombinant DNA encoding a recombinant protein comprising SEQ ID NO: 10.

19. The method of claim 1, wherein the recombinant DNA encoding a recombinant protein comprising SEQ ID NO: 11.

20. The method of claim 1, wherein the recombinant DNA encoding a recombinant protein comprising SEQ ID NO: 12.

21. A method comprising:
inserting a first nucleic acid sequence encoding a recombinant HIV-1 gp140 into a first vector, thereby constructing a second vector for expression of a recombinant protein comprising the recombinant HIV-1 gp140 fused to a tag through a peptide linker at C-terminus of the recombinant HIV-1 gp140; and
expressing the recombinant protein in cells growing in a culture medium;
wherein the first vector comprises an expression cassette comprising:
a regulatory region operably linked to a second nucleic acid sequence encoding a secretion signal peptide,
a third nucleic acid sequence encoding the peptide linker and the tag to be fused to C-terminus of the recombinant HIV-1 gp140, and
an insertion region comprising two or more restriction sites,
wherein the second nucleic acid sequence is adjacent to 5' end of the insertion region and the third nucleic acid sequence is adjacent to 3' end of the insertion region,
wherein the first nucleic acid sequence is inserted into the first vector at the insertion region,
wherein the regulatory region regulates expression of the recombinant protein in a cell carrying the second vector,
wherein the recombinant protein expressed in cells assembles into recombinant trimers in the culture medium;

wherein each of the recombinant trimers comprises a trimer base formed by the recombinant HIV-1 gp140 not including the peptide linker and the tag, wherein the peptide linker has a sufficient length to separate the tag from the trimer base so that the tag is accessible for binding by a binding molecule immobilized on a solid matrix used in protein purification, thereby allowing purification of the recombinant trimers from the culture medium;

wherein the recombinant trimers mimic native HIV-1 Env trimers, wherein the peptide linker comprises at least 20 amino acids; and wherein the peptide linker does not bind to the binding molecule during purification.

22. The method of claim 21, wherein the peptide linker comprises at least 23 amino acids.

23. The method of claim 21, wherein the peptide linker comprises SEQ ID NO: 1.

24. The method of claim 21, wherein the peptide linker comprises SEQ ID NO: 5.

25. The method of claim 21, wherein the peptide linker comprises SEQ ID NO: 6.

26. The method of claim 21, wherein the peptide linker comprises SEQ ID NO: 7.

27. The method of claim 21, wherein the peptide linker comprises a flexible linker.

28. The method of claim 27, wherein the flexible linker comprises SEQ ID NO: 8.

29. The method of claim 21, wherein the peptide linker comprises a rigid linker.

30. The method of claim 29, wherein the rigid linker comprises SEQ ID NO: 9.

31. The method of claim 21, wherein the tag comprises SEQ ID NO: 2.

32. The method of claim 21, wherein the tag comprises SEQ ID NO: 3.

33. The method of claim 21, wherein the insertion region comprises restriction sites NheI and NotI.

34. The method of claim 21, wherein the regulatory region comprises a human cytomegalovirus (CMV) promoter.

35. The method of claim 21, wherein the secretion signal peptide comprises a human CD5 signal peptide.

36. The method of claim 21, wherein the first vector is a plasmid vector.

37. The method of claim 21, wherein the recombinant HIV-1 gp140 encoded by the first nucleic acid sequence comprising a gp120 and a gp41 ectodomain, and wherein the gp120 and the gp41 ectodomain are joined by a junction sequence comprising a furin cleavage site REKR.

38. The method of claim 37, wherein the gp41 ectodomain is truncated at aa664 based on HXB2 numbering.

39. The method of claim 37, wherein the furin cleavage site REKR is mutated to SEKS, and wherein the recombinant HIV-1 gp140 is furin cleavage resistant.

40. The method of claim 37, wherein the furin cleavage site REKR is mutated to an amino acid sequence comprising SEQ ID NO: 13, and wherein the recombinant HIV-1 gp140 is furin cleavage proficient.

41. The method of claim 37, wherein the recombinant HIV-1 gp140 comprises "SOSIP" mutations that comprise A501C, T605C, and I559P, and wherein the recombinant HIV-1 gp140 comprises five "stabilizing" mutations comprising I535M, Q543L, S553N, K567Q, and R588G.

42. The method of claim 21, wherein the recombinant protein comprises SEQ ID NO: 10.

43. The method of claim 21, wherein the recombinant protein comprises SEQ ID NO: 11.

44. The method of claim 21, wherein the recombinant protein comprises SEQ ID NO: 12.

45. The method of claim 1 comprising purifying the recombinant trimers from the culture medium by affinity chromatography using the binding molecule immobilized on the solid matrix, wherein the binding molecule immobilized on the solid matrix is able to bind to the tag.

46. The method of claim 21 comprising purifying the recombinant trimers from the culture medium by affinity chromatography using the binding molecule immobilized on the solid matrix, wherein the binding molecule immobilized on the solid matrix is able to bind to the tag.

* * * * *

UNITED STATES PATENT AND TRADEMARK OFFICE
CERTIFICATE OF CORRECTION

PATENT NO. : 9,975,924 B2
APPLICATION NO. : 14/806742
DATED : May 22, 2018
INVENTOR(S) : Venigalla B. Rao et al.

Page 1 of 1

It is certified that error appears in the above-identified patent and that said Letters Patent is hereby corrected as shown below:

In the Specification

Column 1, Lines 28-32, replace the existing paragraph with the following:
--This invention was made with government support under Grant No. A1102725 awarded by the National Institutes of Health. The government has certain rights in the invention.--

Signed and Sealed this
Eighteenth Day of June, 2019

Andrei Iancu
*Director of the United States Patent and Trademark Office*